United States Patent
Lalicki et al.

(10) Patent No.: US 12,251,487 B2
(45) Date of Patent: Mar. 18, 2025

(54) ELECTRIC LIGHT RADIANT ENERGY CONTROL SYSTEMS

(71) Applicant: Vyv, Inc., Latham, NY (US)

(72) Inventors: Jorel Lalicki, Troy, NY (US); Robert Barron, Boulder, CO (US); Cori Joslyn Winslow, Port Washington, NY (US); Yichuan Wang, Troy, NY (US)

(73) Assignee: Vyv, Inc., Latham, NY (US)

( * ) Notice: Subject to any disclaimer, the term of this patent is extended or adjusted under 35 U.S.C. 154(b) by 0 days.

(21) Appl. No.: 18/242,332

(22) Filed: Sep. 5, 2023

(65) Prior Publication Data

US 2023/0405171 A1 Dec. 21, 2023

Related U.S. Application Data

(63) Continuation of application No. 16/577,871, filed on Sep. 20, 2019, now abandoned, which is a
(Continued)

(51) Int. Cl.
*A61L 2/00* (2006.01)
*A61L 2/08* (2006.01)
(Continued)

(52) U.S. Cl.
CPC ............... *A61L 2/24* (2013.01); *A61L 2/084* (2013.01); *A61L 2/10* (2013.01); *A61L 2/28* (2013.01);
(Continued)

(58) Field of Classification Search
CPC ... A61L 2/24; A61L 2/084; A61L 2/10; A61L 2/28; A61L 2/0047; A61L 2/0052;
(Continued)

(56) References Cited

U.S. PATENT DOCUMENTS

| | | | |
|---|---|---|---|
| 1,493,820 A | 5/1924 | Miller et al. | |
| 2,622,409 A | 12/1952 | Stimkorb | |

(Continued)

FOREIGN PATENT DOCUMENTS

| | | |
|---|---|---|
| CN | 1932370 A | 3/2007 |
| CN | 201396611 Y | 2/2010 |

(Continued)

OTHER PUBLICATIONS

Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 5 pages.

(Continued)

*Primary Examiner* — Monzer R Chorbaji
(74) *Attorney, Agent, or Firm* — Banner & Witcoff, Ltd.

(57) ABSTRACT

Radiant energy control systems, methods, and apparatuses are provided. An example light emitting device may comprise a sensor operable to detect whether a space is occupied, and a controller in communication with the sensor and operable to cause output, via a first light emitter white light comprising a wavelength range of 380 to 420 nm, and cause output, via a second light emitter a non-white light comprising a wavelength range of 380 to 420 nm.

20 Claims, 15 Drawing Sheets

Related U.S. Application Data continuation of application No. 15/857,128, filed on Dec. 28, 2017, now abandoned, which is a continuation-in-part of application No. 15/856,971, filed on Dec. 28, 2017, now abandoned.

(60) Provisional application No. 62/440,208, filed on Dec. 29, 2016.

(51) Int. Cl.
| | |
|---|---|
| A61L 2/10 | (2006.01) |
| A61L 2/24 | (2006.01) |
| A61L 2/28 | (2006.01) |
| A61L 9/20 | (2006.01) |
| A61N 5/00 | (2006.01) |
| G01N 21/00 | (2006.01) |
| G01N 23/00 | (2006.01) |
| A61L 12/06 | (2006.01) |
| G01N 31/22 | (2006.01) |

(52) U.S. Cl.
CPC .............. *A61L 9/20* (2013.01); *A61L 2/0047* (2013.01); *A61L 2/0052* (2013.01); *A61L 12/063* (2013.01); *A61L 2202/11* (2013.01); *A61L 2202/14* (2013.01); *A61L 2202/25* (2013.01); *A61L 2209/111* (2013.01); *G01N 31/226* (2013.01)

(58) Field of Classification Search
CPC .... A61L 9/20; A61L 2202/11; A61L 2202/14; A61L 2202/25; A61L 12/063; A61L 2209/111; G01N 31/226
USPC .............. 422/24; 250/492.1, 453.11, 454.11, 250/455.11
See application file for complete search history.

(56) References Cited

U.S. PATENT DOCUMENTS

| | | |
|---|---|---|
| 2,773,715 A | 12/1956 | Lindner |
| 3,314,746 A | 4/1967 | Millar |
| 3,670,193 A | 6/1972 | Thorington et al. |
| 3,791,864 A | 2/1974 | Steingroever |
| 3,926,556 A | 12/1975 | Boucher |
| 3,992,646 A | 11/1976 | Corth |
| 4,121,107 A | 10/1978 | Bachmann |
| 4,461,977 A | 7/1984 | Pierpoint et al. |
| 4,576,436 A | 3/1986 | Daniel |
| 4,867,052 A | 9/1989 | Cipelletti |
| 4,892,712 A | 1/1990 | Robertson et al. |
| 4,910,942 A | 3/1990 | Dunn et al. |
| 5,231,472 A | 7/1993 | Marcus et al. |
| 5,489,827 A | 2/1996 | Xia |
| 5,530,322 A | 6/1996 | Ference et al. |
| 5,559,681 A | 9/1996 | Duarte |
| 5,668,446 A | 9/1997 | Baker |
| 5,721,471 A | 2/1998 | Begemann et al. |
| 5,725,148 A | 3/1998 | Hartman |
| 5,800,479 A | 9/1998 | Thiberg |
| 5,901,564 A | 5/1999 | Comeau, II |
| 5,915,279 A | 6/1999 | Cantrall et al. |
| 5,962,989 A | 10/1999 | Baker |
| 5,968,766 A | 10/1999 | Powers |
| 6,031,958 A | 2/2000 | McGaffigan |
| 6,166,496 A | 12/2000 | Lys et al. |
| 6,183,500 B1 | 2/2001 | Kohler |
| 6,242,752 B1 | 6/2001 | Soma et al. |
| 6,246,169 B1 | 6/2001 | Pruvot |
| 6,251,127 B1 | 6/2001 | Biel |
| 6,379,022 B1 | 4/2002 | Amerson et al. |
| 6,477,853 B1 | 11/2002 | Khorram |
| 6,524,529 B1 | 2/2003 | Horton, III |
| 6,551,346 B2 | 4/2003 | Crossley |
| 6,554,439 B1 | 4/2003 | Teicher et al. |
| 6,627,730 B1 | 9/2003 | Burnie |
| 6,676,655 B2 | 1/2004 | McDaniel |
| 6,791,259 B1 | 9/2004 | Stokes et al. |
| 6,902,807 B1 | 6/2005 | Argoitia et al. |
| 7,015,636 B2 | 3/2006 | Bolta |
| 7,175,807 B1 | 2/2007 | Jones |
| 7,190,126 B1 | 3/2007 | Paton |
| 7,198,634 B2 | 4/2007 | Harth et al. |
| 7,201,767 B2 | 4/2007 | Bhullar |
| 7,213,941 B2 | 5/2007 | Sloan et al. |
| 7,438,719 B2 | 10/2008 | Chung et al. |
| 7,476,885 B2 | 1/2009 | Garcia et al. |
| 7,503,675 B2 | 3/2009 | Demarest et al. |
| 7,516,572 B2 | 4/2009 | Yang et al. |
| 7,521,875 B2 | 4/2009 | Maxik |
| 7,611,156 B2 | 11/2009 | Dunser |
| 7,612,492 B2 | 11/2009 | Lestician |
| 7,658,891 B1 | 2/2010 | Barnes |
| 7,955,695 B2 | 6/2011 | Argoitia |
| 8,035,320 B2 | 10/2011 | Sibert |
| 8,214,084 B2 | 7/2012 | Ivey et al. |
| 8,232,745 B2 | 7/2012 | Chemel et al. |
| 8,357,914 B1 | 1/2013 | Caldwell |
| 8,398,264 B2 | 3/2013 | Anderson et al. |
| 8,467,052 B1 | 6/2013 | Chao et al. |
| 8,476,844 B2 | 7/2013 | Hancock et al. |
| 8,481,970 B2 | 7/2013 | Cooper et al. |
| 8,506,612 B2 | 8/2013 | Ashdown |
| 8,508,204 B2 | 8/2013 | Deurenberg et al. |
| 8,761,565 B1 | 6/2014 | Coleman et al. |
| 8,886,361 B1 | 11/2014 | Harmon et al. |
| 8,895,940 B2 | 11/2014 | Moskowitz et al. |
| 8,999,237 B2 | 4/2015 | Tumanov |
| 9,024,276 B2 | 5/2015 | Pugh et al. |
| 9,027,479 B2 | 5/2015 | Raksha et al. |
| 9,028,084 B2 | 5/2015 | Maeng et al. |
| 9,039,966 B2 | 5/2015 | Anderson et al. |
| 9,046,227 B2 | 6/2015 | David et al. |
| 9,078,306 B2 | 7/2015 | Mans et al. |
| 9,119,240 B2 | 8/2015 | Nagazoe |
| 9,173,276 B2 | 10/2015 | Van Der Veen et al. |
| 9,257,059 B2 | 2/2016 | Raksha et al. |
| 9,283,292 B2 | 3/2016 | Kretschmann |
| 9,313,860 B2 | 4/2016 | Wingren |
| 9,323,894 B2 | 4/2016 | Kiani |
| 9,333,274 B2 | 5/2016 | Peterson et al. |
| 9,368,695 B2 | 6/2016 | David et al. |
| 9,410,664 B2 | 8/2016 | Krames et al. |
| 9,420,671 B1 | 8/2016 | Sugimoto et al. |
| 9,433,051 B2 | 8/2016 | Snijder et al. |
| 9,439,271 B2 | 9/2016 | Ku et al. |
| 9,439,989 B2 | 9/2016 | Lalicki et al. |
| 9,492,576 B1 | 11/2016 | Cudak et al. |
| 9,581,310 B2 | 2/2017 | Wu et al. |
| 9,623,138 B2 | 4/2017 | Pagan et al. |
| 9,625,137 B2 | 4/2017 | Li et al. |
| 9,681,510 B2 | 6/2017 | van de Ven |
| 10,806,812 B2 | 10/2020 | Barron et al. |
| 2002/0074559 A1 | 6/2002 | Dowling et al. |
| 2002/0122743 A1 | 9/2002 | Huang |
| 2003/0009158 A1 | 1/2003 | Perricone |
| 2003/0019222 A1 | 1/2003 | Takahashi et al. |
| 2003/0023284 A1 | 1/2003 | Gartstein et al. |
| 2003/0124023 A1 | 7/2003 | Burgess et al. |
| 2003/0178632 A1 | 9/2003 | Hohn et al. |
| 2003/0207644 A1 | 11/2003 | Green et al. |
| 2003/0222578 A1 | 12/2003 | Cok |
| 2003/0231485 A1 | 12/2003 | Chien |
| 2004/0008523 A1 | 1/2004 | Butler |
| 2004/0010299 A1 | 1/2004 | Tolkoff et al. |
| 2004/0024431 A1 | 2/2004 | Carlet |
| 2004/0039242 A1 | 2/2004 | Tolkoff et al. |
| 2004/0047142 A1 | 3/2004 | Goslee |
| 2004/0147984 A1 | 7/2004 | Altshuler et al. |
| 2004/0147986 A1 | 7/2004 | Baumgardner et al. |
| 2004/0158541 A1 | 8/2004 | Notarianni et al. |
| 2004/0159039 A1 | 8/2004 | Yates et al. |
| 2004/0162596 A1 | 8/2004 | Altshuler et al. |

(56) References Cited

U.S. PATENT DOCUMENTS

| | | |
|---|---|---|
| 2004/0230259 A1 | 11/2004 | Di Matteo |
| 2004/0262595 A1 | 12/2004 | Mears et al. |
| 2004/0266546 A1 | 12/2004 | Huang |
| 2005/0055070 A1 | 3/2005 | Jones et al. |
| 2005/0104059 A1 | 5/2005 | Friedman et al. |
| 2005/0107849 A1 | 5/2005 | Altshuler et al. |
| 2005/0107853 A1 | 5/2005 | Krespi et al. |
| 2005/0159795 A1 | 7/2005 | Savage et al. |
| 2005/0207159 A1 | 9/2005 | Maxik |
| 2005/0212397 A1 | 9/2005 | Murazaki et al. |
| 2005/0253533 A1 | 11/2005 | Lys et al. |
| 2005/0267233 A1 | 12/2005 | Joshi |
| 2006/0006678 A1 | 1/2006 | Herron |
| 2006/0009822 A1 | 1/2006 | Savage et al. |
| 2006/0022582 A1 | 2/2006 | Radkov |
| 2006/0071589 A1 | 4/2006 | Radkov |
| 2006/0085052 A1 | 4/2006 | Feuerstein et al. |
| 2006/0138435 A1 | 6/2006 | Tarsa et al. |
| 2006/0186377 A1 | 8/2006 | Takahashi et al. |
| 2006/0230576 A1 | 10/2006 | Meine |
| 2006/0247741 A1 | 11/2006 | Hsu et al. |
| 2006/0262545 A1 | 11/2006 | Piepgras et al. |
| 2007/0023710 A1 | 2/2007 | Tom et al. |
| 2007/0061050 A1 | 3/2007 | Hoffknecht |
| 2007/0115665 A1 | 5/2007 | Mueller et al. |
| 2007/0164232 A1 | 7/2007 | Rolleri et al. |
| 2007/0208395 A1 | 9/2007 | Leclerc et al. |
| 2007/0258851 A1 | 11/2007 | Fogg et al. |
| 2008/0008620 A1 | 1/2008 | Alexiadis |
| 2008/0015560 A1 | 1/2008 | Gowda et al. |
| 2008/0091250 A1 | 4/2008 | Powell |
| 2008/0151533 A1 | 6/2008 | Genova |
| 2008/0278927 A1 | 11/2008 | Li et al. |
| 2008/0305004 A1 | 12/2008 | Anderson et al. |
| 2008/0307818 A1 | 12/2008 | Min et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0262515 A1 | 10/2009 | Lee et al. |
| 2009/0285727 A1 | 11/2009 | Levy |
| 2009/0314308 A1 | 12/2009 | Kim et al. |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0102252 A1 | 4/2010 | Harmon et al. |
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0014538 A1 | 1/2012 | Bozkurt et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0181246 A1 | 7/2013 | Wu |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2013/0323375 A1 | 12/2013 | Takahashi et al. |
| 2014/0043810 A1 | 2/2014 | Jo et al. |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0265868 A1 | 9/2014 | Morrisseau |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0049459 A1 | 2/2015 | Peeters et al. |
| 2015/0062892 A1 | 3/2015 | Krames et al. |
| 2015/0068292 A1 | 3/2015 | Su et al. |
| 2015/0086420 A1* | 3/2015 | Trapani .................. A61L 9/20 |
| | | 422/24 |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0000953 A1 | 1/2016 | Bettles et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0091172 A1 | 3/2016 | Wu et al. |
| 2016/0114067 A1 | 4/2016 | Dobrinsky et al. |
| 2016/0114186 A1 | 4/2016 | Dobrinsky et al. |
| 2016/0137528 A1 | 5/2016 | Wipprich |
| 2016/0168384 A1 | 6/2016 | Guidolin et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0349179 A1 | 12/2016 | Rochette et al. |
| 2016/0354502 A1 | 12/2016 | Simmons et al. |
| 2016/0366745 A1 | 12/2016 | Hikmet et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0246331 A1 | 8/2017 | Lloyd |
| 2017/0281812 A1 | 10/2017 | Dobrinsky et al. |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0117194 A1 | 5/2018 | Dobrinsky et al. |
| 2018/0124883 A1 | 5/2018 | Bailey |
| 2018/0139817 A1 | 5/2018 | Yamakawa et al. |
| 2018/0180226 A1 | 6/2018 | Van Bommel et al. |
| 2018/0185533 A1 | 7/2018 | Lalicki et al. |
| 2018/0190625 A1 | 7/2018 | Steckel et al. |
| 2018/0280723 A1 | 10/2018 | Enwemeka et al. |
| 2018/0311386 A1 | 11/2018 | Hawkins et al. |
| 2018/0320872 A1 | 11/2018 | Weeks, Jr. et al. |
| 2019/0070323 A1 | 3/2019 | Atreya et al. |
| 2019/0368936 A1 | 12/2019 | Xu et al. |
| 2019/0371978 A1 | 12/2019 | Iwasa et al. |

FOREIGN PATENT DOCUMENTS

| | | |
|---|---|---|
| CN | 201423033 Y | 3/2010 |
| CN | 102213382 A | 10/2011 |

(56) References Cited

FOREIGN PATENT DOCUMENTS

| | | |
|---|---|---|
| CN | 103227255 A | 7/2013 |
| CN | 105304801 A | 2/2016 |
| CN | 105339094 A | 2/2016 |
| CN | 105449081 A | 3/2016 |
| CN | 205360038 U | 7/2016 |
| CN | 106937461 A | 7/2017 |
| CN | 107575849 A | 1/2018 |
| DE | 102011001097 A1 | 9/2012 |
| DE | 102015207999 A1 | 11/2016 |
| DE | 102016009175 A1 | 2/2017 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2008-004948 A | 1/2008 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| JP | 2015174026 A | 10/2015 |
| KR | 20130096965 A | 9/2013 |
| KR | 101526261 B1 | 6/2015 |
| KR | 20160021100 A | 2/2016 |
| KR | 101648216 B1 | 8/2016 |
| KR | 20160127469 A | 11/2016 |
| KR | 101799538 B1 | 11/2017 |
| TW | M268106 U | 6/2005 |
| TW | 201412240 A | 4/2014 |
| TW | 201604490 A | 2/2016 |
| TW | 201611849 A | 4/2016 |
| TW | M530654 U | 10/2016 |
| TW | 201711707 A | 4/2017 |
| TW | 201831977 A | 9/2018 |
| TW | 201936226 A | 9/2019 |
| WO | 0114012 A1 | 3/2001 |
| WO | 03037504 A1 | 5/2003 |
| WO | 2003035118 A2 | 5/2003 |
| WO | 03063902 A2 | 8/2003 |
| WO | 03084601 A2 | 10/2003 |
| WO | 03089063 A1 | 10/2003 |
| WO | 2004033028 A2 | 4/2004 |
| WO | 2005048811 A2 | 6/2005 |
| WO | 2005049138 A1 | 6/2005 |
| WO | 2006023100 A1 | 3/2006 |
| WO | 2006100303 A2 | 9/2006 |
| WO | 2006126482 A1 | 11/2006 |
| WO | 2007012875 A1 | 2/2007 |
| WO | 2007035907 A2 | 3/2007 |
| WO | 2008071206 A1 | 6/2008 |
| WO | 2009056838 A1 | 5/2009 |
| WO | 2010110652 A1 | 9/2010 |
| WO | 2015066099 A2 | 5/2015 |
| WO | 2015189112 A1 | 12/2015 |
| WO | 2016019029 A1 | 2/2016 |
| WO | 2016068285 A1 | 5/2016 |
| WO | 2016209632 A1 | 12/2016 |
| WO | 2017009534 A1 | 1/2017 |
| WO | 2017205578 A1 | 11/2017 |
| WO | 2019108432 A1 | 6/2019 |

OTHER PUBLICATIONS

Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio, 6 pages.
Dai et al., "Blue light for infectious diseases: Propionibacterium acnes, Helicobacter pylori, and beyond?," Drug Resist Update, 15(4): 223-236 {Aug. 2012), 18 pages.
Halstead et al., "The antibacterial activity of blue light against nosocomial wound pathogens growing planktonically and as mature biofilms," Appl. Environ, Microbial., vol. 82, No. 13, Jul. 2016, pp. 4006-4016, 11 pages, retrieved from: https://aem.asm.org/content/aem/82/13/4006.full.pdf.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214., 12 pages.
Tomb et al., "Inactivation of Streptomyces phage C31 by 405 nm light," Bacteriophage, 4:3, Jul. 2014, retrieved from: http://dx.doi.org/10.4161/bact.32129, 7 pages.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://www.researchgate.net/publication/304628914., 10 pages.
Dec. 8, 2016—(WO) ISR & WO—App PCT/US2016/036704 (Kenall Manufacturing Company).
LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html, Published Jun. 14, 2007, 2 pages.
EDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.
LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.
LEDs Magazine, "ANSI continues advancements on SSL chromaticity standard," retrieved from the Internet on Apr. 20, 2017 at: http://www.ledsmagazine.com/articles/print/volume-12/issue-11/features/standards/ansi-continues-advancements-on-ssl-chromaticity-standard.html, Published Dec. 8, 2015, 6 pages.
Soraa, "PAR30L," retrieved from the Internet on Apr. 20, 2017 at: http://www_soraa.com/products/22-PAR30L, 6 pages.
Soraa, "PAR30L 18.5W," retrieved from the Internet on Apr. 20, 2017 at: http://wwwv.soraa.com/products, 5 pages.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76, 8 pages.
Oct. 20, 2016—(WO) ISR & WO—App PCT/US2016/44634.
Color Phenomena, "CIE-1931 Chromaticity Diagram," last updated Aug. 22, 2013, retrieved from www.color-theory-phenomena.nl/10.02.htm on Jan. 20, 2016, 3 pages.
Nov. 2, 2015—(WO) WO & ISR—App PCT/US2015/042678.
Jun. 6, 2017—(US) Third Party Submission—U.S. Appl. No. 15/223,134.
Yu, J. et al., "Efficient Visible-Light-Induced Photocatalytic Disinfection on Sulfur-Doped Nanocrystalline Titania," Environ. Sic. Technol., 39, 2005, pp. 1175-1179, 5 pages.
Demidova, T. et al., "Photodynamic Therapy Targeted to Pathogens," International Journal of Immunopathology and Pharmacology, 17(3), pp. 245-254, 10 pages.
Ashkenazi, H. et al., "Eradication of Propionibacterium acnes by its endogenic porphyrins after illumination with high Intensity blue light," FEMS Immunology and Medical Microbiology, 35, pp. 17-24, 8 pages.
Elman, M. et al., "The Effective Treatment of Acne Vulgaris by a High-intensity, Narrow Band 405-420 nm Light Source," Cosmetic & Laser Ther, 5, pp. 111-116, 6 pages.
Sikora, A. et al., "Lethality of visable light for *Escherichia coli*hemH 1 mutants influence of defects in DNA repair," DNA Repair 2, pp. 61-71, 11 pages.

(56) References Cited

OTHER PUBLICATIONS

Huffman, D. et al., "Inactivation of Bacteria, Virus and Cryptospordium by a Point-of-use Device Using Pulsed Broad Spectrum White Light," Wat. Res. 34(9), pp. 2491-2498, 8 pages.
Papageorgiou, P. et al., "Phototherapy with Blue (415 nm) and Red (660 nm) Light in the Treatment of Acne Vulgaris," British Journal of Dermatology, 2000, pp. 973-978, 6 pages.
Burchard, R. et al., "Action Spectrum for Carotenogenesis in Myxococcus xanthus," Journal of Bateriology, 97(3), 1969, pp. 1165-1168, 4 pages.
Wainwright, "Photobacterial activity of phenothiazinium dyes against methicillin-resistant strains of Staphylococcus aureus," Oxford University Press Journals, retrieved from: http://dx.doi.org/10.1111/j.1574-6968.1998.tb12908.x on Jul. 23, 2015, 8 pages.
Yoshimura et al., "Antimicrobial effects of phototherapy and photochemotherapy in vivo and in vitro," British Journal of Dermatology, 1996, 135: 528-532, 6 pages.
Wilson et al., "Killing of methicillin-resistant Staphylococcus aureus by low-power laser light," J. Med, Microbial., vol. 42 (1995), pp. 62-66, 5 pages.
Kawada et al., "Acne Phototherapy with a high-intensity, enhanced, narrow-band, blue light source: an open study and in vitro investigation," Journal of Dermatological Science 30 (2002) pp. 129-135, 7 pages.
Maclean et al., "High-intensity narrow-spectrum light inactivation and wavelength sensitivity of Staphylococcus auresu," FEMS Microbial. Lett., vol. 285 (2008) pp. 227-232, 6 pages.
Reed, "The History of Ultraviolet Germicidal Irradiation for Air Disinfection," Public Health Reports, Jan.-Feb. 2010, vol. 125, 13 pages.
Ward, "Experiments on the Action of Light on Bacillus anthracis," Received Dec. 15, 1892, 10 pages.
Hamblin et al., "Helicobacter pylori Accumulates Photoactive Porphyrins and Is Killed by Visable Light," Antimicrobial Agents and Chemotherapy, Jul. 2005, pp. 2822-2827, 6 pages.
Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3}, pp. 1238-1245, 8 pages.
Holzman, "405-nm Light Proves Potent at Decontaminating Bacterial Pathogens," retrieved from: http://forms.asm.org/microbe/index.asp?bid=64254 on Aug. 6, 2015, 34 pages.
Guffey et al., "In Vitro Bactericidal Effects of 405-nm and 470-nm Blue Light," Photomedicine and Laser Surgery, vol. 24, No. 6, retrieved from: https://www.liebertpub.com/doi/abs/10.1089/pho.2006.24.684 on Mar. 23, 2018, abstract only provided, 2 pages.
Kristoff et al., "Loss of photoreversibility for UV mutation in E. coli using 405 nm or near—US challenge," Mutat Res., May 1983, 109{2}: 143-153, 2 pages, abstract only provided.
Turner et al., "Comparative Mutagenesis and Interaction Between Near-Ultraviolet {313- to 405-nm) and Far-Ultraviolet 254-nm) Radiation in Escherichia coli Strains with Differeing Repair Capabilities," Journal of Bacteriology, vol. 147, No. 2, Aug. 1981, pp. 410-417, 8 pages.
Knowles et al., "Near-Ultraviolet Mutagenesis in Superoxide Dismutase-deficient Strains of Escherichia coli," Environmental Health Perspectives, vol. 102{1), Jan. 1994, pp. 88-94, 7 pages.
Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.
Chukuka et al., Visible 405 nm SLD light photo-destroys metchicillin-resistant Staphylococcus aureus {MRSA) in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.
Bek-Thomsen, M., "Acne is Not Associated with Yet-Uncultured Bacteria," J. Clinical Microbial., 2008, 46{10), 9 pages.
Harrison, A.P., "Survival of Bacteria," Annu. Rev. Microbial, 1967, p. 143, vol. 21, 1 page.
Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only, 4 pages.
Pochi, P.E., "Acne: Androgens and microbiology," Drug Dev, Res., 1988, val. 13, 4 pages, abstract only provided.
Burkhart, C. G. et al., "Acne: a review of immunologic and microbiologic factors," Postgraduate Medical Journal, 1999, vol. 75, pp. 328-331, 5 pages.
Jappe, U., "Pathological mechanisms of acne with special emphasis on Propionibacterium acnes and related therapy," Acta Dermato-Venereologica, 2003, vol. 83, pp. 241-248, 8 pages.
Burkhart, C. N. et al., "Assessment of etiologic agents in acne pathogenesis," Skinmed, 2003, vol. 2, No. 4, pp. 222-228, 7 pages.
May 12, 2020—(JP) Final Office Action—JP 2018-525520.
Jun. 18, 2020—(WO) IPRP & WO—App PCT/US2018/061859.
Mar. 18, 2020—(WO) ISR & WO—App PCT/US2019/068799.
Jul. 6, 2020—(WO) ISR & WO—App PCT/US2019/068799.
Jul. 23, 2020—(TW) Office Action w/TR—TW 108148627.
Jul. 28, 2020—(TW) Office Action 3 w/TR—TW 107143577.
Nov. 6, 2020—(TW) Office Action w/Tr.—TW 108146777.
Dec. 2, 2020—(TW) Rejection Decision—App 108111242 (Eng Trans).
Sep. 29, 2020—(WO) ISR & WO—App PCT/US2020/046504.
Nov. 23, 2020—(WO) ISR & WO—App PCT/US2020/051254.
Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.
Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.
Jul. 21, 2021—(TW) Office Action—TW 108148627.
Aug. 31, 2021—(CN) Office Action—CN 201980033309.1.
Sep. 21, 2021—(JP) Office Action—2020-154129.
Oct. 21, 2021—(TW) Office Action—TW 109132488 w/Trn.
Nov. 15, 2021—(CA) Office Action—CA 3095579.
Tong, Y., et al. "Population study of atmospheric bacteria at the Fengtai district of Beijing on two representative days," Aerobiologica, 1993, vol. 9, 1 page, Abstract only provided.
Tong, Y. et al., "Solar radiation is shown to select for pigmented bacteria in the ambient outdoor atmosphere," Photochemistry and Photobiology, 1997, val. 65, No. 1, pp. 103-106, 4 pages.
Marshall, J. H., et al., "Pigments of Staphylococcus aureus, a series of triterpenoid carotenoids," J. Bacteriology, 1981, vol. 147, No. 3, pp. 900-913, 14 pages.
Pelz, A. et al., "Structure and Biosythesis of Staphyloxanthin from Staphylococcus aureus," Journal of Biological Chemistry, Sep. 16, 2005, 9 pages.
Sakai, K., et al., "Search Method for inhibitors of staphyloxanthin production by methicillin-resistant Staphylococcus aureus," Biol. Pharm. Bull., 2012, vol. 35, No. 1, pp. 48-53, 6 pages.
Clauditz, A. et al., "Staphyloxanthin plays a role in the fitness of Staphylococcus aureus and its ability to cope with oxidative stress," Infection and Immunity, 2006, vol. 74, No. 8, 7 pages.
Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, pp. 2806-2810, http://www.jmest.org/wp-content/uploads/JMESTN42351112.pdf, 5 pages.
Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/, 11 pages.
Jun. 29, 2018—(DE) Office Action—App 112016003453.9.
Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012, 6 pages.

(56) References Cited

OTHER PUBLICATIONS

Mar. 6, 2018—(WO) ISR & WO—App PCT/US2017/068749.
Apr. 16, 2018—(WO) ISR & WO—App PCT/US2017/068755.
Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE, 4 pages.
Berezow Alex, How to Kill Insects With Visible Light, Real Clear Science, Jan. 11, 2015, pp. 1-4<https://www.realclearscience.com/journal_club/2015/01/12/how_to_kill_insects_with_visible_light_109021.html>, 4 pages.
Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan<https://www.semanticscholar.org/paper/Lethal-effects-of-short-wavelength-visible-light-o-Hori-Shibuya/2c11cb3f70a059a051d8ed02fff0e8a9b7a4c4d4>, 6 pages.
Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>, 5 pages.
Dornob, "Healthy Handle: Self-Sanitizing UV Door Knob Kills Germs", Dornob.com, Dec. 5, 2018, pp. 1-6, https://dornob.com/healthy-handle-self-sanitizing-uv-door-knob-kills-germs/, 6 pages.
Kickstarter, "Orb, The World's First Germ-Killing Blue/UV Light Ball", Dec. 10, 2018, pp. 1-10, <https://www.kickstarter.com/projects/572050089078660/orbtm-the-worlds-first-germ-killing-uv-light-ball>, 10 pages.
NuTone, "QTNLEDB LunAura Collection 110 CFM Fan, Light, LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809, 1 page.
NuTone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90, 2 pages.
NuTone, "Ultra Pro™ Series Single-Speed Fans and Fan/Lights", Dec. 11, 2018, p. 1, http://www.hutone.com/products/filter/ultra-pro-series-fanlights-eb590f89-dca2-40e7-af39-06e4cccb96ca, 1 page.
Nov. 27, 2018—(JP) Office Action—JP 2018-525520.
Jan. 4, 2019—(TW) Office Action—App 104124977.
Feb. 11, 2019—(WO) ISR—App PCT/US2018/061859.
Feb. 28, 2019—(WO) ISR—App PCT/US2018/061843.
Feb. 28, 2019—(WO) ISR & WO—App PCT/US2018/061856.
Apr. 15, 2019—(CA) Examiner's Report—App 2,993,825.
Absorption and Fluorescence Spectroscopy of Tetraphenylporphyrins and Metallo-Tetraphenylporphyrin, article, 2005, 11 pp., Atomic, Molecular and Supramolecular Studies.
Dayer, et al., Band Assignment in Hemoglobin Porphyrin Ring Spectrum: Using Four-Orbital Model of Gouterman, article, Sep. 8, 2009, Protein & Peptide Letters, 2010, vol. 17, No. 4, Department of Biology, Faculty of Sciences, Shahid Chamran University of Ahvaz, Tehran, Iran, 7 pages.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2 , 2017, J Fac Med Baghdad.
Nussbaum, et al., Effects of 630-, 660-, 810-, and 905-nm Laser Irradiation, Delivering Radiant Exposure of 1-50 J/cm2 on Three Species of Bacteria in Vitro, journal, 2002, vol. 20, No. 6, 2002, Journal of Clinical LaserMedicine & Surgery, Canada, 9 pages.
Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea, 9 pages.
Rita Giovannetti, The Use of Spectrophotometry UV-Vis for the Study of Porphyrins, article, 2012, 23 pp., InTech Europe, Croatia.
Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University of Hull, Kingston-Upon-Hull, HU6 7RX, U.K., 51 pages.
Jul. 8, 2019—(WO) ISR & WO—App PCT/US2019/024593.
Nov. 5, 2019—(JP) Final Office Action—JP 2018-525520.
Oct. 9, 2019—(CN) Office Action—CN 201680048598.9.
Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Oct. 31, 2008—(WO) ISR & WO—App PCT/GB2008/003679 (Univ Strathclyde).
May 4, 2010—(WO) IPRP—App PCT/GB2008/003679 (Univ Strathclyde).
Apr. 3, 2020—(WO) ISR & WO—App PCT/US2019/67444.
Jun. 1, 2020—(GB) Examiner's Report—App GB1802648.4.
Apr. 14, 2020—(TW) 2nd Office Action—App 107143577.

\* cited by examiner

ELECTRIC LIGHT RADIANT ENERGY CONTROL SYSTEMS

CROSS-REFERENCE TO RELATED APPLICATIONS

This patent is a continuation of U.S. application Ser. No. 16/577,871, filed Sep. 20, 2019, which is a continuation of U.S. application Ser. No. 15/857,128, filed Dec. 28, 2017, which is a continuation-in-part of U.S. application Ser. No. 15/856,971, filed Dec. 28, 2017, and claims the benefit of U.S. Provisional Application No. 62/440,208, filed Dec. 29, 2016. U.S. application Ser. No. 15/857,128, U.S. application Ser. No. 15/856,971, and U.S. Provisional Application No. 62/440,208 are hereby incorporated by reference herein.

TECHNICAL FIELD

Aspects of the present disclosure generally relate to electric light systems, methods, and apparatus for using, generating, controlling or detecting radiant energy. Aspects of the present disclosure relate to controlling electric light sources that emit radiation in at least the near-ultraviolet portion of the light spectrum.

BACKGROUND OF THE INVENTION

The disclosure relates generally to illumination, and more particularly, to control systems for a disinfecting light emitting diode (LED) lighting system and methods of regulating operations of the disinfecting LED lighting systems.

Light-emitting devices are a primary requirement in most indoor occupied environments to provide illumination of the area, of tasks being completed in the area, and of the area's occupants and objects. Alternative light sources have been created with additional performance factors in mind that utilize emitted light in different manners. Lighting fixtures and devices for horticulture, health, warmth, and disinfection have been demonstrated. In addition to being tuned for luminous efficacy of radiation, these lighting fixtures and devices are tuned to provide increased outputs of certain regions of radiation to accomplish the additional performance factor. In these lighting fixtures and devices that emit light for multiple functions, the light emissions can be balanced to achieve an acceptable level of each function. One of the functions can be general illumination (e.g., when the multiple-function lighting fixtures and devices are used in spaces occupied by humans), in which case, achieving a relatively high luminous efficacy of the emitted light is balanced not only against achieving desirable color characteristics of the emitted light, but also of achieving the one or more other functions to an acceptable or desired level. New laws and regulations around energy efficiency in residential and commercial spaces means that these multiple function light sources must also have control systems to balance energy efficiency in addition to their desired effects.

One new function of lighting is disinfecting, e.g. using blue light in combination with other light to emit what is perceived as white light. Unlike ultraviolet light (UV), white disinfecting light can be used on 24 hour/7 days without harming the occupants of a room. UV systems require extensive safety measures to prevent accidental exposure or unknown occupants and have emergency shut off switches in situations of accidental occupancy. UV systems include remote controlled robots and lockable rooms, which can only be used when a room is not occupied, which is not always feasible. Disinfecting white light does not require such safety features.

BRIEF DESCRIPTION OF THE INVENTION

A first aspect of the disclosure provides a control system for a disinfecting light system including a disinfecting light fixture, the control system including: a controller operably coupled to the disinfecting light fixture, the disinfecting light fixture illuminating a space, where the controller regulates an operation of the disinfecting light fixture by performing processes including at least one of: adjusting an amount of disinfecting energy provided to the space by the disinfecting light fixture in response to at least one of: determining an amount of disinfecting energy provided to the space by the disinfecting light fixture does not meet a disinfecting energy threshold, determining a sensed bacterial load of the space does not meet a bacterial load threshold, or determining the amount of disinfecting energy provided to the space by the disinfecting light fixture does not meet a preferred amount of disinfecting energy associated with a detected, environmental characteristic of the space; or adjusting an amount of illuminating light provided to the space by the disinfecting light fixture in response to determining the amount of illuminating light provided to the space by the disinfecting light fixture does not meet a preferred amount of illuminating light.

A second aspect of the disclosure provides a method of regulating operations of a disinfecting light fixture of a disinfecting light system, the method including: obtaining data relating to a space illuminated by the disinfecting light fixture, the data including at least one of: an amount of disinfecting energy provided to the space by the disinfecting light fixture, a bacterial load of the space illuminated by the disinfecting light fixture, or an environmental characteristic of the space; and adjusting at least one of: the amount of disinfecting energy provided to the space by the disinfecting light fixture in response to at least one of: determining the amount of disinfecting energy provided to the space by the disinfecting light fixture does not meet a disinfecting energy threshold, determining the bacterial load of the space does not meet a bacterial load threshold, or determining the amount of disinfecting energy provided to the space by the disinfecting light fixture does not meet a preferred amount of disinfecting energy associated with the environmental characteristic of the space; or an amount of illuminating light provided to the space by the disinfecting light fixture in response to determining the amount of illuminating light provided to the space by the disinfecting light fixture does not meet a preferred amount of illuminating light.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As an initial matter, in order to clearly describe the current disclosure it will become necessary to select certain terminology when referring to and describing relevant components within the disclosure. When doing this, if possible, common industry terminology will be used and employed in a manner consistent with its accepted meaning. Unless otherwise stated, such terminology should be given a broad interpretation consistent with the context of the present application and the scope of the appended claims. Those of ordinary skill in the art will appreciate that often a particular component may be referred to using several different or overlapping terms. What may be described herein as being a single part may include and be referenced in another context as consisting of multiple components. Alternatively, what may be described herein as including multiple components may be referred to elsewhere as a single part.

As indicated above, the disclosure relates generally to illumination, and more particularly, to control systems for a disinfecting light emitting diode (LED) lighting system and methods of regulating operations of the disinfecting LED lighting systems.

These and other embodiments are discussed below with reference to FIGS. 1-15. However, those skilled in the art will readily appreciate that the detailed description given herein with respect to these Figures is for explanatory purposes only and should not be construed as limiting.

Figure 1:
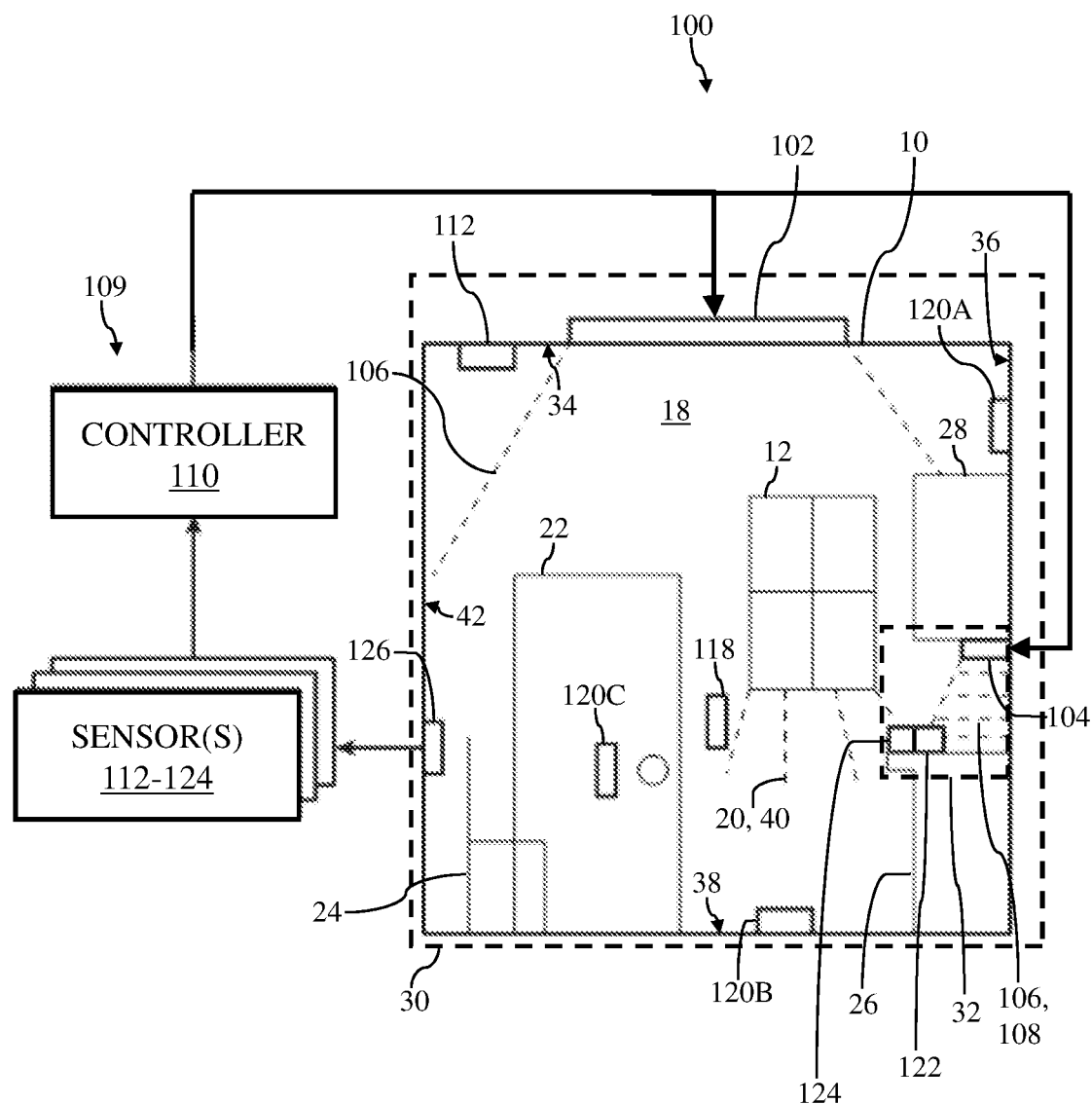
FIG. 1 shows a schematic view of an illustrative environment including a disinfecting light system and a control system, according to embodiments of the disclosure.

FIG. 1 shows a schematic view of an illustrative environment including a disinfecting light system and a control system. Specifically, FIG. 1 shows environment 10 and a disinfecting light system 100 that may be at least partially positioned within and/or may interact with environment 10. In the non-limiting example shown in FIG. 1, environment 10 may be a room within a building. As discussed herein, disinfecting light system 100 may illuminate environment 10, as well as provide disinfecting energy within environment 10 in order to disinfect environment 10. It is understood that the term "environment" and "room" may be used interchangeably when discussing the non-limiting examples herein. Additionally, although shown as only a single room, it is understood that environment 10 may include a plurality of rooms and/or distinct areas that include disinfecting light system 100.

As shown in the non-limiting example of FIG. 1, environment 10 may include at least one of the items and/or objects included therein. Specifically, and at least partially dependent on the type of environment 10 (e.g., room), environment 10 may include a plurality of items and/or objects positioned within environment 10. For example, environment 10 formed as a room may include a window 12 formed in one of a plurality of walls 18 of environment. As such in FIG. 1, the window may provide an opening to environment 10 which may allow sunlight or natural light 20 to enter and/or be emitted into environment 10. Additionally, in non-limiting examples, environment 10 may also include a door 22 to allow user(s) (FIGS. 12 and 13) to access environment 10 and/or the items or objects positioned therein. Additionally, environment 10 may also include a chair 24, desk or workstation 26 (hereafter, "workstation 26"), and cabinets 28. In a non-limiting example, workstation 26 may be a "clean" or "sterile" workstation or area that may be used for specific, sterile procedures and/or processing (e.g., sterile table for microchip inspection). As discussed herein, the items and/or objects (e.g., window 12, chair 24, workstation 26, and so on) may be accounted for when regulating the operations of disinfecting light system 100, and more specifically, regulating the disinfecting energy and/or illuminating light provided to environment 10 by disinfecting light system 100. Additionally, characteristics and/or properties of environment 10 may also be accounted for and/or may affect the regulation of operations of disinfecting light system 100, and more specifically the regulation of the disinfecting energy and/or illuminating light provided to environment 10, as discussed herein. For example, and as discussed in detail herein, the color of paint on walls 18/door 22, the amount of sun exposure for environment 10 based on window 12, the size of environment 10, and so on, may be accounted for and/or may affect the regulation of the disinfecting energy and/or illuminating light provided to environment 10 by disinfecting light system 100.

Environment 10 may include one or more spaces defined therein. For example, environment 10 may include and/or be "divided" into a plurality of distinct spaces 30, 32. Specifically, and as shown in the non-limiting example of FIG. 1, environment 10 (e.g., room) may include a first space 30 and a second space 32. In this non-limiting example, second space 32 may be included within first space 30. However, and as discussed herein, second space 32 may be defined as distinct and/or unique from first space 30 by disinfecting light system 100. That is, the spaces 30, 32 of environment 10 may be based on and/or may be defined by, at least in part, disinfecting light system 100 of environment 10 and its various components (e.g., light fixtures), as discussed herein. Additionally, or alternatively, the plurality of spaces 30, 32 of environment 10 may be based on and/or may be defined by, at least in part, items and/or objects of environment 10 (e.g., sterile workstation 26), and/or characteristics and/or properties of environment 10, as discussed herein (see, FIGS. 14 and 15).

The number of spaces 30, 32 shown in FIG. 1 and included within environment 10 are merely illustrative. As such, although two spaces 30, 32 are shown and discussed herein, it is understood that environment 10 may include more or less spaces. In other non-limiting examples where environment 10 includes a plurality of rooms, spaces of environment 10 may be defined as each individual room making up environment 10 (see, FIG. 15). Additionally, or alternatively in the non-limiting examples, each of the plurality of rooms of environment may include one or more spaces similar to those discussed herein with respect to FIG. 1 (see, FIG. 14).

Disinfecting light system 100 included and/or operating within environment 10 may include at least one disinfecting light fixture 102, 104. Disinfecting light fixture(s) 102, 104 may be positioned within, exposed to, illuminate and/or may provide (light) energy to environment That is, and as discussed herein, disinfecting light fixture(s) 102, 104 may be positioned within and/or exposed to environment 10 to provide illuminating light and/or disinfecting energy to environment 10. As shown in the non-limiting example of FIG. 1, a first disinfecting light fixture 102 may be positioned within environment 10 and may be coupled to a ceiling 34 of environment 10. Additionally, a second disinfecting light fixture 104 may be positioned within environment 10 and may be coupled to cabinets 28, adjacent workstation 26. As discussed herein, the plurality of disinfecting light fixture(s) 102, 104 within environment 10 may define, at least in part, space(s) 30, 32 of environment 10. Specifically, the position of each of disinfecting light fixture(s) 102, 104 within environment 10 and/or the area of environment in which the plurality of disinfecting light fixtures(s) 102, 104 may illuminate and/or provide disinfecting energy may, at least in part, define space(s) 30, 32 of environment 10. First disinfecting light fixture 102 coupled to ceiling 34 of environment 10 may illuminate and/or provide disinfecting energy to substantially all of environment 10 (e.g., room). Therefore, the light emitted by first disinfecting light fixture 102 may define, at least in part, first space 30. Additionally, second disinfecting light fixture 104 coupled to cabinet 28 of environment 10 may illuminate and/or provide disinfecting energy to workstation 26. As such, the light emitted by second disinfecting light fixture 104 may define, at least in part, second space 32.

The plurality of disinfecting light fixture(s) 102, 104 of disinfecting light system 100 may be any suitable light fixture, component, or assembly that is capable of providing a spectral range of light energy, illumination, and/or illuminating light, as well as, disinfecting energy to environment 10. Additionally, the plurality of disinfecting light fixture(s) 102, 104 may be any suitable light fixture, component, or assembly that is capable of providing only illuminating light (e.g., disinfecting light fixture output=100% illuminating light), only disinfecting energy (e.g., disinfecting light fixture output=100% disinfecting energy), or both illuminating light and disinfecting energy simultaneously (e.g., disinfecting light fixture output=approximately 70-90% illuminating light, approximately 10-30% disinfecting energy). Additionally, the plurality of disinfecting light fixture(s) 102, 104 may be any suitable light fixture, component, or assembly that is capable of switching between providing only illuminating light, only disinfecting energy, or both illuminating light and disinfecting energy simultaneously. For example, the plurality of disinfecting light fixture(s) 102, 104 of disinfecting light system 100 may include light fixtures similar to those described in U.S. Pat. Nos. 9,333,274, 9,439,989, and U.S. Pat. Pub. No. 2017/0030555 the entirety of which is hereby incorporated herein by reference. Additionally, or alternatively in another non-limiting example discussed herein, the plurality of disinfecting light fixture(s) 102, 104 of disinfecting light system 100 may also be any suitable light fixture, component, or assembly that is capable of adjusting and/or varying the brightness or lumen output of the illuminating light and/or the operational function, output, dosage, and/or intensity (hereafter, "operational intensity") of the disinfecting energy during operation of disinfecting light fixture(s) 102, 104. That is, and as discussed herein, the plurality of disinfecting light fixture(s) 102, 104 may be configured to and/or capable of adjusting the lumen output of the illuminating light and/or the operational intensity of the disinfecting energy provided to environment 10.

In the non-limiting example shown in FIG. 1, first disinfecting light fixture 102 may emit only light energy and/or illuminating light 106 (hereafter, "illuminating light 106") to first space of environment 10. Additionally in the non-limiting example shown in FIG. 1, second disinfecting light fixture 104 may emit both illuminating light 106, as well as, disinfecting energy 108 to second space 32 of environment 10. As discussed herein, the output (e.g., illuminating light 106, disinfecting energy 108) of each of the plurality of disinfecting light fixture(s) 102, 104 may be based on sensed or measured characteristics of space(s) 30, 32 of environment 10, characteristics and/or properties of space(s) 30, 32 of environment 10, and/or predetermined information (e.g., scheduled outputs) for environment 10.

The number of disinfecting light fixture(s) 102, 104 included within environment 10, as shown in the non-limiting example of FIG. 1, is understood to be illustrative. As such, although disinfecting light system 100 is shown to include two disinfecting light fixture(s) 102, 104, it is understood that disinfecting light system 100 may include more or less disinfecting light fixture(s). Additionally, the position of disinfecting light fixture(s) 102, 104 included within environment 10, as shown in the non-limiting example of FIG. 1, is understood to be illustrative. Disinfecting light fixture(s) 102, 104 of disinfecting light system 100 may be positioned anywhere within, adjacent to, and/or exposed to environment 10 to provide illuminating light 106 and/or disinfecting energy 108 to a defined space within environment as discussed herein.

Furthermore, and as discussed in detail in U.S. Pat. Nos. 9,333,274, 9,439,989, and U.S. Pat. Pub. No. 2017/0030555 incorporated herein by reference, illuminating light 106 may generate visible light energy within the spectral range of approximately 380 nanometers (nm) to approximately 750 nm, and disinfecting energy 108 may be a disinfecting energy within the spectral range of approximately 380 nm to approximately 420 nm (e.g., 405 nm). That is, illuminating light 106 may include visible light energy within a spectral range that may illuminate and/or provide light to space(s) 30, 32 of environment 10. Additionally, disinfecting energy 108 generated by disinfecting light fixture(s) 102, 104 (see, second disinfecting light fixture 104) may include disinfecting energy within the spectral range that may alter, adjust, and/or control the bacterial load, bioburden, and/or microbial load (e.g., disinfect, or sterilize) within space(s) 30, 32 receiving disinfecting energy 108 (e.g., violet light). In another non-limiting example, disinfecting energy 108 may include ultraviolent (UV) light having disinfecting properties and including a spectral range of approximately 100 nm to approximately 400 nm.

In a non-limiting example, and as discussed herein, during operation of the plurality of disinfecting light fixture(s) 102, 104 illuminating light 106 and/or disinfecting energy 108 may be varied and/or adjusted. Specifically, the plurality of disinfecting light fixture(s) 102, 104 may be capable of varying and/or adjusting the lumen output of illuminating light 106 and/or the operational intensity of disinfecting light 108 during operation of disinfecting light fixture(s) 102, 104 of disinfecting light system 100. For example, during operation of disinfecting light fixture(s) 102, 104, the lumen output of illuminating light 106 may be adjusted to increase or decrease the brightness of illuminating light 106, and the operational intensity of disinfecting energy 108 may be adjusted to increase or decrease the amount of disinfecting energy 108 provided to space(s) 30, 32. The lumen output of illuminating light 106 may be varied between approximately 0% of the total lumen output, brightness, and/or illuminating capabilities of illuminating light 106 (e.g., 0%=no illuminating light 106), and approximately 100% of the total lumen output, brightness, and/or illuminating capabilities of illuminating light 106 (e.g., 100%=illuminating light 106 at maximum brightness or lumen output). Additionally, the operational intensity of disinfecting energy 108 may be varied between approximately 0% of the total operational intensity of disinfecting energy, and/or disinfecting capabilities of disinfecting energy 108 (e.g., 0%=no disinfecting energy), and approximately 100% of the total operational intensity of disinfecting energy, and/or disinfecting capabilities of disinfecting energy 108 (e.g., 100%=disinfecting energy 108 at maximum operational intensity or output). Regardless of the variation or change in lumen output and/or operational intensity, illuminating light 106 may be emitted within the spectral range of approximately 380 nm to approximately 750 nm, and disinfecting energy 108 may be emitted within the spectral range of approximately 380 nm to approximately 420 nm, or alternatively approximately 100 nm to approximately 420 nm. Additionally in a non-limiting example, the illuminating light 106 and/or disinfecting energy 108 may be adjusted and/or varied independent of the function and/or operation of one another. For example, disinfecting light fixture(s) 102, 104 may adjust the lumen output of the emitted illuminating light 106 when disinfecting light fixture(s) 102, 104 is not emitting disinfecting energy 108, or alternatively, without adjusting or varying the operational intensity of the emitted disinfecting energy 108 when disinfecting light fixture(s) 102, 104 is emitting disinfecting energy 108 along with illuminating light 106. Additionally, disinfecting light fixture(s) 102, 104 may adjust the operational intensity of the emitted disinfecting energy 108 when disinfecting light fixture(s) 102, 104 is not emitting illuminating light 106, or alternatively, without adjusting or varying the lumen output of the emitted illuminating light when disinfecting light fixture(s) 102, 104 is emitting illuminating light 106 along with disinfecting energy 108. Furthermore in the non-limiting example where both illuminating light 106 and disinfecting energy 108 are both being emitted by disinfecting light fixture(s) 102, 104, the lumen output of illuminating light 106 and the operational intensity of disinfecting energy 108 may be adjusted and/or varied simultaneously. In this non-limiting example, the lumen output of illuminating light 106 and the operational intensity of disinfecting energy 108 may be adjusted and/or varied independent of one another (e.g., increase in the lumen output of illuminating light 106, decrease in the operational intensity of disinfecting energy 108). The lumen output of illuminating light 106 and the operational intensity of disinfecting energy 108 may be adjusted and/or varied based on sensed or measured characteristics of space(s) 30, 32 of environment characteristics and/or properties of space(s) 30, 32 of environment 10, and/or predetermined information (e.g., scheduled outputs) for environment 10.

Furthermore, and as a result of adjusting the lumen output of illuminating light 106 and/or the operational intensity of disinfecting energy 108, a quality of visible light generated by and/or provided to space(s) 30, 32 by disinfecting light fixtures 102, 104 may be affected. For example, when disinfecting light fixtures 102, 104 is providing both illuminating light 106 and disinfecting energy 108 an output ratio may be between approximately 70-90% of illuminating light 106 and approximately 10-30% disinfecting energy 108. In these non-limiting examples, a user of space(s) 30, 32 may not detect any change in quality (e.g., color rendering) in illuminating light 106 based on the inclusion or emission of disinfecting energy 108 (e.g., violet light). However, when disinfecting energy 108 is adjusted (e.g., increased beyond 30%, increased operational intensity) the quality of light provided to space(s) 30, 32 by illuminating light 106 may be affected. For example, where disinfecting energy 108 is increased, the violet light may become more apparent and/or visible to a user of space(s) 30, 32, and/or certain colors forming illuminating light 106 may be come over or under saturated by violet light of disinfecting energy 108. As discussed herein, certain circumstances and/or situations for space(s) 30, 32 (e.g., task(s) being performed in first space 30) may require more or less illuminating light 106 and/or disinfecting energy 108, and may be performed or carried out within space(s) 30, 32 with less disinfecting energy 108 and high light quality, or alternatively, may be performed with more disinfecting energy 108 and low light quality.

As shown in FIG. 1, disinfecting energy system 100 can include a control system 109 including at least one controller 110 configured to control operation of disinfecting light fixture(s) 102, 104. That is, controller 110 of control system 109 may be configured to regulate illuminating light 106 and disinfecting energy 108 (e.g., vary/adjust lumen output/operational intensity) provided to space(s) 30, 32 of environment 10 via disinfecting light fixture(s) 102, 104. Controller 110 can be hard-wired and/or wirelessly connected to, operably coupled to, and/or in communication with disinfecting light fixture(s) 102, 104 via any suitable electronic and/or mechanical communication component or technique. Controller 110, and its various components discussed herein (see, FIG. 7), may be a single stand-alone system that functions separate from another system (e.g., computing device) (not shown) that may control and/or adjust operations or functions of other portions of environment (e.g., HVAC system). Alternatively, controller 110 may be integrally formed within, in communication with and/or formed as a part of a larger control system (e.g., computing device) (not shown) that may control and/or adjust operations or functions of environment 10. For example, controller 110 of control system 109 may be configured or formed as a microcontroller or similarly embedded system on a chip (SOC) component running a real-time operating system (RTOS).

Additionally, in the non-limiting example shown in FIG. 1, control system 109 for disinfecting light system 100 may also include one or more sensors 112, 118, 120A, 120B, 120C, 122, 124 operably coupled to and/or in communication with controller 110 for aiding controller 110 in controlling the operation of disinfecting light fixture(s) 102, 104. As discussed herein, controller 110 may utilize data, real-time information, and/or environment characteristics of space(s) 30, 32 of environment 10, as determined by sensor(s) 112, 118, 120A, 120B, 120C, 122, 124, to control the operation of disinfecting light fixture(s) 102, 104 to ultimately regulate illuminating light 106 and disinfecting energy 108 provided to space(s) 30, 32 of environment 10.

As shown in FIG. 1, controller 110 of control system 109 may be operably coupled to, in electrical and/or mechanical communication with sensor(s) 112, 118, 120A, 120B, 120C, 122, 124 positioned throughout environment 10 (e.g., one shown). Additionally, and as shown in the non-limiting example of FIG. 1, controller 110 may be wirelessly connected to, and/or in communication with sensor(s) 112, 118, 120A, 120B, 120C, 122, 124. Sensor(s) 112, 118, 120A, 120B, 120C, 122, 124 may be positioned in various locations and/or throughout environment 10, and more specifically space(s) 30, 32. The position and/or location of sensor(s) 112, 118, 120A, 120B, 120C, 122, 124 within space(s) 30, 32 of environment 10 may be dependent, at least in part, on the type of sensor, and/or the data, information, and/or characteristic of space(s) 30, 32 the sensor is measuring, detecting, and/or sensing. Sensor(s) 112, 118, 120A, 120B, 120C, 122, 124 in communication with controller 110 of control system 109 may be any suitable sensor or device configured to detect and/or determine data, information, and/or characteristics relating to environment 10. For example, and as discussed in detail herein, sensor(s) 112, 118, 120A, 120B, 120C, 122, 124 positioned within space(s) 32 may be any suitable sensor configured to detect, measure, sense, and/or determine an amount of disinfecting energy 108 provided to space(s) 30, 32 by disinfecting light fixture(s) 102, 104, a bacterial load for space(s) 30, 32, and/or environmental characteristics (e.g., occupancy, daylight) for space(s) 30, 32.

In the non-limiting example shown in FIG. 1, environment 10 may include a first sensor 112. Specifically, first space 30 of environment 10 may include first sensor 112 positioned therein and in (wireless) communication with and/or operably connected to controller 110 of control system 109. In the non-limiting example, first sensor 112 may be positioned on and/or coupled to ceiling 34 within first space 30. First sensor 112 may be configured as any suitable sensor capable of measuring an amount of disinfecting energy 108 provided to space 30 by first disinfecting light fixture 102 of disinfecting light system 100. For example, first sensor 112 of disinfecting light system 100 may include or be formed as a spectrometer, a photodiode, a watt meter, or any other suitable sensor that may be capable of measuring and/or detecting the amount of disinfecting energy 108 provided to first space 30 by first disinfecting light fixture 102.

The amount of disinfecting energy 108 provided to first space 30 by first disinfecting light fixture 102, as measured by first sensor 112, may be provided or transmitted to controller 110 to aid in controller's regulation of disinfecting energy 108 generated by first disinfecting light fixture 102 of disinfecting light system 100. As discussed herein, controller 110 may compare the measured amount of disinfecting energy 108 provided to first space 30 by first disinfecting light fixture 102 to a disinfecting energy threshold, and may adjust the amount of disinfecting energy 108 provided to space 30 by adjusting the output of first disinfecting light fixture 102. Although shown as being coupled to ceiling 34 within first space 30 of environment 10, it is understood that first sensor 112 may be positioned anywhere within first space 30 so long as first sensor 112 is capable of measuring the amount of disinfecting energy 108 provided to first space 30 by first disinfecting light fixture 102.

As shown in FIG. 1, environment 10 may also include a second sensor 118. Specifically, first space 30 of environment 10 may include second sensor 118 positioned therein and in (wireless) communication with and/or operably connected to controller 110 of control system 109. In the non-limiting example, second sensor 118 may be positioned on and/or coupled to wall 18 within first space 30. Second sensor 118 may be configured as any suitable sensor capable of sensing a bacterial load of space 30. More specifically, second sensor 118 may be any suitable sensor capable of sensing bacterial load, bioburden, and/or microbial load within space 30 of environment 10. For example, second sensor 118 of disinfecting light system 100 may include or be formed as an optical sensor, oxygen-depletion sensor, luminometer, or any other suitable sensor that may be capable of sensing a bacterial load within first space 30. In non-limiting examples, second sensor 118 may sense the bacterial load of first space 30 by measuring the bacterial load of the air within first space 30, and/or measuring the bacterial load on a surface of an object or item (e.g., window 12, wall 20, door 22, chair 24, and so on) positioned within first space 30.

In other non-limiting examples, the bacterial load of first space 30 may be based on a correlated measurement. The correlated measurement may be a calculated or determined bacterial load based on collected data that may be correlated to a bacterial load measurement. That is, data collected, measured, determined, and/or sensed by second sensor 118 may be provided to controller 110, which in turn may process and/or utilize the data from second sensor 118 to calculate or determined the bacterial load forming the correlated measurement. In non-limiting examples, the data collected by second sensor 118 may not be data including and/or pertaining directly to bacteria, microbial, and/or bioburden data, but rather may be data that can be utilized to calculate or determined the bacterial load, as discussed herein.

The bacterial load of first space 30 may change based on changes within first space 30. For example, the bacterial load of first space 30 may increase as a result of increased room occupancy by users, when new items or objects are introduced to first space 30 of environment 10 and/or over a period of time where first disinfecting light fixture 102 is not providing disinfecting energy 108 to first space 30. The bacterial load of space 30, sensed by second sensor 118, may be provided or transmitted to controller 110 to aid in controller's regulation of disinfecting energy 108 generated by first disinfecting light fixture 102 of disinfecting light system 100. As discussed herein, controller 110 may compare the sensed bacterial load of first space 30 to a bacterial load threshold, and may adjust the amount of disinfecting energy 108 provided to space 30 by adjusting the output of first disinfecting light fixture 102. That is, the bacterial load sensed by second sensor 118 within first space 30 may be directly affected and/or impacted by the amount of disinfecting energy 108 provided to space by first disinfecting light fixture 102. Although shown as being coupled to wall 18 within space 30 of environment 10, it is understood that second sensor 118 may be positioned anywhere within space 30 so long as second sensor 118 is capable of sensing the bacterial load of first space 30.

First space 30 of environment 10 may also include at least one additional, third sensor 120A, 120B, 120C positioned therein and in (wireless) communication with and/or operably connected to controller 110 of control system 109. In the non-limiting example, control system 109 may include a plurality of third sensors 120A, 120B, 120C positioned throughout first space 30 of environment 10. Each of the plurality of third sensors 120A, 120B, 120C may be configured as environmental characteristic sensors, and/or may be sensors configured to measure or detect environmental characteristics of first space 30 of environment 10. As discussed herein, a preferred amount of disinfecting energy for and/or to be provided to first space 30 may be associated with the environmental characteristics detected by third sensors 120A, 120B, 120C within first space 30. Additionally, controller 110 may compare the measured amount of disinfecting energy 108 within first space 30 (e.g., first sensor) with the preferred amount of disinfecting energy associated with detected environmental characteristics of first space 30, and may adjust the amount of disinfecting energy 108 provided to space 30 by adjusting the output of first disinfecting light fixture 102.

Also discussed herein, each of the environmental characteristics detected by third sensors 120A, 120B, 120C may include a preferred amount or level of illuminating light that may be associated with the detected environmental characteristic(s). That is, a preferred amount of illuminating light for and/or to be provided to first space 30 may be associated with the environmental characteristics detected by third sensors 120A, 120B, 120C within first space Additionally, controller 110 may compare a measured amount of illuminating light 106 provided to first space 30 (e.g., third sensor, disinfecting light fixture) with the preferred amount of illuminating light associated with detected environmental characteristics of first space 30, and may adjust the amount of illuminating light 106 provided to space 30 by adjusting the output of first disinfecting light fixture 102. In the non-limiting example shown in FIG. 1, and discussed herein, the plurality of third sensors 120A, 120B, 120C configured to detect environmental characteristics of first space 30 may all be the distinct types of sensors and/or may detect distinct environmental characteristics of first space 30. In another non-limiting example, the plurality of third sensors 120A, 120B, 120C may all be the same type of sensor and/or may detect the same environmental characteristics of first space 30.

Third sensor 120A may be positioned on and/or coupled to a wall 36 within first space 30. Additionally, third sensor 120A may be coupled to wall 36, above cabinet 28 included within first space 30. Third sensor 120A may be configured as any suitable sensor capable of measuring or detecting an occupancy level (e.g., environmental characteristic) for first space 30. The detected occupancy level for first space 30 may include whether or not first space 30 is being occupied and/or includes a user(s) positioned therein, the number of users that may occupy first space 30 and/or a (real-time) change in occupancy for first space 30. In non-limiting examples, third sensor 120A of control system 109 may include or be formed as an infrared sensor, an automated camera system (e.g., image processing with camera based sensors), radar sensor, Lidar sensor, audio sensor, (tomographic) motion sensor, microwave sensor, ultrasonic sensor, or any other suitable sensor that may be capable of detecting an occupancy level of first space 30.

The occupancy level of first space 30, as detected by third sensor 120A, may be provided or transmitted to controller 110 to aid in controller's regulation of disinfecting energy 108 generated by first disinfecting light fixture 102 of disinfecting light system 100. As discussed herein, controller 110 may receive the occupancy level of first space 30 from third sensor 120A, along with a preferred amount of disinfecting energy associated with the occupancy level of first space 30. Additionally, controller 110 may compare the measured amount of disinfecting energy 108 of first space 30 (e.g., first sensor 112) with the preferred amount of disinfecting energy associated with the occupancy level of first space 30 detected by third sensor 120A, and may adjust the amount of disinfecting energy 108 provided to space 30 by adjusting the output of first disinfecting light fixture 102. Furthermore, and similar to the preferred amount of disinfecting light, controller 110 may adjust the amount of illuminating light 106 provided to space 30 by adjusting the output of first disinfecting light fixture 102 based on the preferred amount of illuminating light that may be associated with the detected, occupancy level of first space 30. Although shown as being coupled to wall 36 within first space 30 of environment 10, it is understood that third sensor 120A may be positioned anywhere within first space 30 so long as third sensor 120A is capable of detecting the occupancy level of first space 30.

Third sensor 120B may be positioned on and/or coupled to floor 38 of environment 10. Specifically, third sensor 120B may be coupled to floor 38 with first space 30, substantially adjacent, aligned with, below and/or within proximity of window 12 included within first space 30 of environment 10. Additionally, as shown in FIG. 1, third sensor 120B may be positioned substantially below, aligned with, and/or within proximity of first disinfecting light fixture 102 of disinfecting light system 100. Third sensor 120B may be configured as any suitable sensor capable of detecting an amount of visible light (e.g., illuminating light 106, natural light) in first space 30. In non-limiting examples, third sensor 120B of control system 109 may include or be formed as a spectrometer, a photodiode, a watt meter, or any other suitable sensor that may be capable of sensing an amount of visible light (e.g., illuminating light 106, natural light) within first space 30.

In a non-limiting example, third sensor 120B may be configured as a daylight sensor that may sense an amount of natural light 20 included within first space 30. The amount of natural light of first space 30, as sensed by third sensor 120B, may be provided or transmitted to controller 110 to aid in controller's regulation of disinfecting energy 108 generated by first disinfecting light fixture 102 of disinfecting light system 100. As discussed herein, controller 110 may receive the amount of natural light 20 of first space 30 from third sensor 120B, along with a preferred amount of disinfecting energy associated with the detected amount of natural light 20 of first space 30. Additionally, controller 110 may compare the measured amount of disinfecting energy 108 of first space 30 (e.g., first sensor 112) with the preferred amount of disinfecting energy associated with the amount of natural light 20 of first space 30 detected by third sensor 120B, and may adjust the amount of disinfecting energy 108 provided to space by adjusting the output of first disinfecting light fixture 102.

Additionally, the amount of natural light 20 sensed by third sensor 120B may also include a known, calculated, predetermined, and/or measurable amount of natural disinfecting energy (e.g., spectral energy of approximately 405 nm), which may be provided to first space 30. In one non-limiting example, third sensor 120B of control system 109 may be configured to measure an amount of natural disinfecting energy 40 provided to first space 30 along with natural light 20. In another non-limiting example, the amount of natural disinfecting energy from natural light 20 may be calculated or determined based on a variety of factors including, but not limited to, the time of day, the date, the position of first space 30 and/or window 12 (e.g., facing east), and characteristics of window 12 (e.g., double-pane, blue light blocker, tinted, and so on). In a non-limiting example, controller 110 of control system 109 may receive the measured amount of natural disinfecting energy 40, or determine the amount of natural disinfecting energy 40, provided to first space 30 via natural light 20 sensed by third sensor 120B, and may adjust the amount of disinfecting energy 108 provided to space 30 by adjusting the output of first disinfecting light fixture 102.

In another non-limiting example, third sensor 120B may be configured as a visible light sensor that may sense the amount of illuminating light 106 provided to first space 30 by first disinfecting light fixture 102. In the non-limiting example, the amount of illuminating light 106 provided to first space 30 by first disinfecting light fixture 102, and sensed by third sensor 120B, may be provided or transmitted to controller 110 to aid in the controller's regulation of illuminating light 106 generated by first disinfecting light fixture 102. As discussed herein, controller 110 may receive the amount of illuminating light 106 of first space 30 from third sensor 120B, along with a preferred amount of illuminating light associated with first space 30. The preferred amount of illuminating light may be based on sensed or measured characteristics of first space 30 (e.g., occupancy level, amount of natural light 20, task(s), and so on), characteristics and/or properties of first space 30, and/or predetermined information (e.g., scheduled outputs) for first space 30. Additionally, controller 110 may compare the measured amount of illuminating light 106 of first space 30 with the preferred amount of illuminating light for first space 30, and may adjust the amount of illuminating light 106 provided to first space 30 by adjusting the output of first disinfecting light fixture 102.

In an additional non-limiting example, third sensor 120B may be configured as a visible light sensor that may sense a total amount of visible light (e.g., combination or sum of illuminating light 106 and natural light 20) within first space 30, as well as sense natural light 20 provided to first space 30, as discussed herein. In this non-limiting example, third sensor 120B may provide the total amount of visible light and natural light 20 provided to first space 30, and sensed by third sensor 120B, to controller 110. In the non-limiting example, controller 110 may analyze and/or compare the total amount of visible light and natural light 20 provided to first space 30 to determine the amount of illuminating light 106 provided to first space 30 by first disinfecting light fixture 102. Controller 110 may then compare the determined amount of illuminating light 106 of first space 30 with a preferred amount of illuminating light for first space 30, and may adjust the amount of illuminating light 106 provided to first space 30 by adjusting the output of first disinfecting light fixture 102. Although shown as being positioned on floor 38 of first space 30, it is understood that third sensor 120B may be positioned anywhere within first space 30 so long as third sensor 120B is capable of sensing the amount of natural light 20 for first space 30.

As shown in the non-limiting example of FIG. 1, third sensor 120C of control system 109 may be positioned within first space 30 of environment 10. Specifically, third sensor 120C may be coupled to door 22 within first space 30. Third sensor 120C may be configured as any suitable sensor capable of identifying at least one task being carried out in first space 30. That is, third sensor 120C may be a task-identifying sensor that may detect, sense, and/or identify task(s) being carried out and/or performed within first space 30 of environment 10. The identified task being carried out and/or performed within the first space 30 may require a predetermined or preferred amount of illuminating light 106 and/or disinfecting energy 108 to be provided to first space 30 by first disinfecting light fixture 102 when performing the task. In non-limiting examples, third sensor 120C of control system 109 may include or be formed as a camera sensor (e.g., image processing with camera based sensors) and/or a scanner sensor that may detect certain work pieces and/or users associated with a predetermined task are positioned or located within first space 30. Additionally in another non-limiting, third sensor 120C may be formed as a component-detection sensor, which may be configured to identify when an object, and/or item (e.g., microscope (not shown)) of first space 30 that is associated with and/or used specifically for a certain task is being utilized within first space 30.

Controller 110 may identify that a task(s) is being carried out in first space 30, via third sensor 120C, and may adjust the amount of disinfecting energy 108 provided to space 30 by adjusting the output of first disinfecting light fixture 102. That is, controller 110 may receive the task(s) being carried out in first space 30, as identified by third sensor 120C, along with a preferred amount of disinfecting energy associated with the identified task being carried out in first space 30. Additionally, controller 110 may compare the measured amount of disinfecting energy 108 of first space 30 (e.g., first sensor 112) with the preferred amount of disinfecting energy associated with the identified task(s) of first space 30, identified by third sensor 120C, and may adjust the amount of disinfecting energy 108 to space 30 by adjusting the output by first disinfecting light fixture 102.

Furthermore, and similar to the preferred amount of disinfecting light, controller 110 may adjust the amount of illuminating light 106 provided to space 30 by adjusting the output of first disinfecting light fixture 102 based on the preferred amount of illuminating light that may be associated with the detected, task(s) being carried out in first space 30. That is, a preferred amount of illuminating light for and/or to be provided to first space 30 may be associated with the task(s) to be performed in first space 30, and detected by third sensor 102C. Additionally, controller 110 may compare a measured amount of illuminating light 106 provided to first space 30 (e.g., third sensor 120B, disinfecting light fixture) with the preferred amount of illuminating light associated with the detected task(s) for first space 30, and may adjust the amount of illuminating light 106 provided to space 30 by adjusting the output of first disinfecting light fixture 102. Although shown as being coupled to door 24 within first space of environment 10, it is understood that third sensor 120C may be positioned anywhere within first space 30 so long as third sensor 120C is capable of that a task(s) is being carried out within first space 30.

The number of sensors 112, 118, 120A, 120B, 120C included within control system 109 for first space 30, as shown in the non-limiting example of FIG. 1, is understood to be illustrative. As such, although control system 109 of disinfecting light system 100 is shown to include five sensors 112, 118, 120A, 120B, 120C within first space 30, it is understood that control system 109 may include more or less sensors for providing data and/or information to controller 110 (see, FIGS. 8-13). Additionally, although first space 30 is shown to include five sensors 112, 118, 120A, 120B, 120C, it is understood that controller 110 may adjust the amount of illuminating light 106 and/or disinfecting energy 108 provided to space 30 by adjusting the output of first disinfecting light fixture 102 based on only a portion of the five sensors 112, 118, 120A, 120B, 120C. In one non-limiting example, control system 109 may include first sensor 112 and one or more third sensors 120A, 120B, 120C. In another non-limiting example, control system 109 may include first sensor 112 and second sensor 118. In an additional non-limiting example, control system 109 may include second sensor 118 and one or more third sensors 120A, 120B, 120C.

Furthermore, although discussed herein as being positioned and/or included within space(s) 32 of environment 10, it is understood that some of sensors 112, 118, 120A, 120B, 120C may be positioned outside of space(s) 30, 32, when applicable. Additionally where sensors 112, 118, 120A, 120B, 120C are positioned outside of space(s) 30, 32, control system 109 may utilize additional components to aid in the measuring, sensing, and/or detected of characteristics relating to space(s) 30, 32, as discussed herein. For example, and as discussed in detail herein with respect to FIG. 8, third sensor 120A configured to detect an occupancy level of space(s) 30, 32 of environment 10 may be configured as a video surveillance system that may monitor activity within space(s) 30, 32, and may be utilized to provide data to third sensor 120A regarding the occupancy level, which in turn may be provided to controller 110 of control system 109, as similarly discussed herein.

Additionally, although discussed herein as sensors 112, 118, 120A, 120B, 120C providing or transmitting data and/or information relating to disinfecting light system 100 and/or space(s) 32 to controller 110, it is understood that some of the data may be provided from distinct components within disinfecting light system 100. For example, and as discussed in detail herein with respect to FIG. 8, data and/or information relating to an amount of illuminating light 106 and/or disinfecting energy 108 provided to first space 30 by first disinfecting light fixture 102 may be provided to controller 110 by first disinfecting light fixture 102 of disinfecting light system 100.

In the non-limiting example shown in FIG. 1, control system 109 of disinfecting light system 100 may also include at least one access control component 126. As shown in FIG. 1, access control component 126 may be positioned within first space 30 of environment 10. Specifically, access control component 126 may be positioned on wall 42, adjacent door 22, within first space 30. Access control component 126 may be operably coupled to and/or in communication with controller 110 for providing data, information, and/or input to controller for controlling the operation of disinfecting light fixture(s) 102 and more specifically, regulating illuminating light 106 and/or disinfecting energy 108 provided to first space 30 of environment 10. For example, access control component 126 may provide an override selector or option that may be configured to temporarily permit switching controller 110 off and/or suspending the operational processes performed by controller 110 of control system 109. In this non-limiting example, a user(s) may utilize access control component 126 to manually adjust the operation of controller 110 for controlling illuminating light 106 and/or disinfecting energy 108 provided to first space 30 by first disinfecting light fixture 102, independent of the data provided to controller 110 by sensors 112, 118, 120A, 120B, 120C. As discussed herein, overriding the operation of controller 110 may result in first disinfecting light fixture 102 maintaining a continuous disinfecting energy 108 within first space 30, or alternatively, maintaining an average disinfection level or amount of disinfecting energy 108 in first space 30 at a minimum level. The continuous disinfecting energy 108 or average disinfection level of disinfecting energy 108 may be maintained despite changes in first space objects or items (e.g., moving chair 24), changes in first space 30 characteristics (e.g., changing wall 18 paint reflectivity, opening/closing curtains on window 12), and/or detected and/or sensed data (e.g., change in bacterial load sensed by second sensor 118, occupancy level detected by third sensor 120A).

In another non-limiting example, access control component 126 may provide a user(s) located in first space 30 the option to manually input a predetermined task to be carried out within first space 30. In this non-limiting example, third sensor 120C may not be included within first space 30, or alternatively, third sensor 120C may not be able to detect the task to be carried out in first space 30 due to circumstances surrounding the task; for example, a workpiece for the task is not yet within first space 30, or first space 30 needs to have a detected amount of disinfecting energy 108 before a workpiece is brought into first space 30 for the task. As such, when a user(s) manually enters a task using access control component 126, the operation of controller 110 for controlling illuminating light 106 and/or disinfecting energy 108 provided to first space 30 by disinfecting light system 102 may be adjusted independent of the data provided to controller 110 by third sensors 120C. That is, user(s) may manually adjust illuminating light 106 and/or disinfecting energy 108 using access control component 126, based on a detected or identified task(s) to be performed with first space 30, independent of the data obtained, sensed, measured, and/or detected by the sensors 112, 118, 120A, 120B, 120C of control system 109, as discussed herein.

In an additional non-limiting example, access control component 126 may include a security access system to allow users access to first space 30 of environment 10. In the non-limiting example, a code associated with a user(s), such as an input code or keycard, may be input, detected, and/or registered with access control component 126, and may provide information, data and/or input from access control component 126 to controller 110 relating to first space 30. For example, when a user inputs their code in access control component 126, access control component 126 may provide information or data relating to an occupancy level of first space 30 based on the user's accessing first space 30 to controller 110. In another example, user(s) may be associated with a specific task to be performed within first space 30. As discussed herein, the specific task associated with the user to be performed in the first space may require a predetermined amount of illuminating light 106 and/or disinfecting energy 108 to be provided to first space 30 by first disinfecting light fixture 102 when performing the task. As such, when user inputs their code in or provides an access key to access control component 126, access control component 126 may provide the user information and/or data to controller 110, which may include the specific task associated with the user, and controller 110 may adjust illuminating light 106 and/or disinfecting energy 108 accordingly, as discussed herein.

In a further non-limiting example, access control component 126 may include and/or be formed as an operational schedule system for first space 30 of environment 10. More specifically, access control component 126 may include and/or be formed as an operational schedule system and/or a system capable of providing a predetermined, operational schedule to controller 110 for controlling the operation of first disinfecting light fixture 102 and/or adjusting illuminating light 106 and/or disinfecting energy 108 provided to first space 30 by first disinfecting light fixture 102. The predetermined, operational schedule provided to controller 110 from access control component 126 may be defined or created by a user(s) and/or operator of disinfecting light system 100 (e.g., building owner or maintenance person for the building include the room forming environment 10).

Additionally, the predetermined operational schedule, which determines how controller 110 adjusts illuminating light 106 and/or disinfecting energy 108 to be provided to first space 30, may be based on a plurality of data, factors, information, and/or operational scenarios surrounding the operation of disinfecting light system 100. For example, the predetermined operational schedule provided to controller 110 may be defined and/or created based on schedule data which includes a time of day and/or a day in a week. That is, controller 110 may adjust illuminating light 106 and/or disinfecting energy 108 provided to first space 30 by first disinfecting light fixture 102 based on the time of day (e.g., day vs. night), and/or the day in the week (e.g., weekday vs. weekend). The schedule data, information, and/or operational scenarios for the predetermined operational scheduled may also include associated, scheduled amounts of disinfecting energy to be provided to first space 30. The scheduled amounts of disinfecting energy to be provided to first space 30 may include, for example, a minimum operational dosage or output of disinfecting energy 108 to be provided to first space 30, and/or an average amount of disinfecting energy 108 (e.g., daily joule dosage, 6 joules per day) to be maintained over a predetermined period of time. For example, during evening hours (e.g., 10:00 PM to 4:00 AM) or on weekends when user(s) are not located in first space 30, as established by the predetermined operational schedule provided by access control component 126, controller 110 may control first disinfecting light fixture 102 such that first disinfecting light fixture 102 does not emit, or alternatively emits a low dosage or lumen output (e.g., 10% brightness) of illuminating light 106. Additionally in the non-limiting example, controller 110 may control first disinfecting light fixture 102 such that output from first disinfecting light fixture 102 is made up and/or includes a minimal percentage of illuminating light 106 (e.g., disinfecting light fixture 102 output=approximately 10% illuminating light 106). The output of illuminating light 106 may be minimal when compared to a total or combined amount of output (e.g., illuminating light 106 and disinfecting energy 108) from first disinfecting light fixture 102. Furthermore in this non-limiting example, and based on the predetermined operational schedule provided by access control component 126, controller 110 may control first disinfecting light fixture 102 such that first disinfecting light fixture 102 emits a maximum operational dosage and/or output (e.g., 100% intensity) or a high operational intensity (e.g., between approximately 75% to approximately 90% intensity) disinfecting energy 108 (e.g., scheduled amount of disinfecting energy). In other non-limiting examples, controller 110 may control first disinfecting light fixture 102 such that first disinfecting light fixture 102 emits a smaller, predetermined operational intensity (e.g., between approximately 10% to approximately 40% intensity) of disinfecting energy 108. In either non-limiting example above, and regardless of the operational intensity of disinfecting energy 108, controller 110 may control first disinfecting light fixture 102 such that output from first disinfecting light fixture 102 is made up and/or includes the remaining percentage of disinfecting energy 108. That is, where controller 110 adjusts the output of illuminating light 106 to be minimal (e.g., disinfecting light fixture 102 output=approximately 10% illuminating light 106), controller 110 may control first disinfecting light fixture 102 such that output from first disinfecting light fixture 102 is made up and/or includes the remaining percentage of disinfecting energy 108 (e.g., disinfecting light fixture 102 output=approximately 90% disinfecting energy 108).

Additionally in this example, controller 110 may adjust illuminating light 106 and/or disinfecting energy 108 based on the predetermined operational schedule provided by access control component 126 to maintain appropriate illuminating light 106 when first space 30 is in use, and maintain a minimum dosage of disinfecting energy 108 with first space 30 (e.g., at night when first space 30 is not being used) (e.g., scheduled amount of disinfecting energy). Furthermore, by adjusting the amount of disinfecting energy 108 when first space 30 is not occupied, an average amount of disinfecting energy 108 (e.g., daily joule dosage, 6 joules per day) can be maintained over a predetermined period of time while also maintaining illuminating light 106 as needed for use of first space 30 (e.g., scheduled amount of disinfecting energy). Continuing the example above, controller 110 may control first disinfecting light fixture 102 during evening hours such that first disinfecting light fixture 102 emits a predetermined amount of disinfecting energy 108 at a specific intensity during the evening hours to maintain a minimum dosage of disinfecting energy 108 in first space 30. In the non-limiting example, controller 110 may control first disinfecting light fixture 102 to emit disinfecting energy 108 at a minimum of 10% operational dosage intensity during the evening hours. Additionally, or alternatively, controller 110 may control first disinfecting light fixture 102 during evening hours such that first disinfecting light fixture 102 emits a predetermined amount disinfecting energy 108 at a specific or determined intensity during the evening hours to maintain an amount of disinfecting energy 108 over the predetermined amount of time. For example, the amount of disinfecting energy 108 over the predetermined amount of time is 6 joules per day. Additionally in the example, it may be determined that during 18-usage hours for first space 30, first disinfecting light fixture 102 may emit disinfecting energy 108 at a 10% intensity to generate 3 joules of energy. As a result, and in order to maintain the amount of disinfecting energy 108 over the predetermined amount of time (e.g., 6 joules per day) for first space 30, controller 110 may control first disinfecting light fixture 102 to emit disinfecting energy 108 at a determined intensity over the next or remaining 6 hours to meet the amount of disinfecting energy 108 over the predetermined amount of time. That is, controller 110 may control first disinfecting light fixture 102 to adjust the disinfecting energy 108, and specifically the intensity of disinfecting energy 108 emitted to first space 30, over the remaining 6 hours to ensure first space 30 receives 6 joules of energy within the day (e.g., amount of disinfecting energy 108 over the predetermined amount of time). Since a 10% operational intensity of disinfecting energy 108 over 18 hours resulted in 3 joules of energy being provided to first space 30, controller 110 may adjust the intensity of disinfecting energy 108 to approximately 30% operational intensity during the remaining 6 hours of the day to ensure first space 30 receives 6 joules of energy within a day.

Although discussed in the example above as averaging the operational intensity of the disinfecting energy 108 to meet the amount of disinfecting energy 108 over the predetermined amount of time (e.g., 10% for 18 hours+30% for 6 hours=6 joules per day), controller 110 may also stagger the intensity to account for potential or possible interruptions to the first space 30 and/or first disinfecting light fixture 102. That is, in another non-limiting example, controller 110 may control or adjust the operation of first disinfecting light fixture 102 to meet the amount of disinfecting energy 108 over the predetermined amount of time before the predetermined amount of time has expired or past. Continuing the example above, the amount of disinfecting energy 108 over the predetermined amount of time is 6 joules per day, and it may be determined that during 18-usage hours for first space 30, first disinfecting light fixture 102 may emit disinfecting energy 108 at a 10% intensity to generate 3 joules of energy. Rather than providing the remaining disinfecting energy 108 at a determined intensity over the remaining 6 hours (e.g., 30% intensity over 6 hours) to meet the amount of disinfecting energy 108 over the predetermined amount of time, controller 110 may control or adjust the operation of first disinfecting light fixture 102 over a shorter period of time. For example, controller 110 may adjust the intensity of disinfecting energy 108 to approximately 60% operational intensity during 3 hours of the remaining 6 hours of the day to ensure first space 30 receives 6 joules of energy within a day. In this non-limiting example, controller 110 may adjust or control the operation of first disinfecting light fixture 102 such that first disinfecting light fixture 102 emits disinfecting energy 108 at approximately 60% operational intensity for 3 hours, and approximately 0% operational intensity (e.g., no emitted disinfecting energy 108) for the distinct 3 hours. Adjusting the operation of first disinfecting light fixture 102 in this manner may provide a fail-safe for meeting the amount of disinfecting energy 108 over the predetermined amount of time, and/or may compensate for unscheduled or unplanned interruptions to first space 30 which may require a change in the operation of first disinfecting light fixture 102 (e.g., janitor enters the room, unscheduled/emergency maintenance during evening hours). Additionally, and as discussed herein, controller 110 may learn, adapt, and/or adjust data relating to first space 30. As a result, and in the non-limiting example discussed herein, controller 110 may anticipate and/or determine a probability or likeliness that first space 30 may experience an unscheduled or unplanned interruption over time. As such, it may be beneficial for controller 110 to utilize the learned or anticipated information relating to the probability or likeliness that first space 30 may experience an unscheduled or unplanned interruption, and control the operation of first disinfecting light fixture 102 in the fail-safe manner discussed herein to meet the amount of disinfecting energy 108 over the predetermined amount of time.

In another example, the predetermined operational schedule provided to controller 110 may be defined and/or created based on schedule data that includes the cost of electricity for operating first disinfecting light fixture 102. As such, controller 110 may adjust illuminating light 106 and/or disinfecting energy 108 provided to first space 30 by first disinfecting light fixture 102 based on when electricity consumption for operating first disinfecting light fixture is at its highest (e.g., peak hours) and its lowest (e.g., off-peak hours). Controller 110 may control operation and/or adjust first disinfecting light fixture 102 to operate (e.g., provide disinfecting energy 108) at minimal power consumption when the electricity costs the most (e.g., peak hours), followed by increased operation (e.g., disinfecting energy 108) when electricity costs the least (e.g., off-peak hours), to maintain an average amount of disinfecting energy 108 (e.g., daily joule dosage) within free space 30. Specifically, first disinfecting light fixture 102 may consume, and/or require more energy to provide disinfecting energy 108 than illuminating light 106. As such, and especially during peak hours, it may be more costly to provide disinfecting energy 108 to first space 30 than illuminating light 106. As such, and based on the predetermined operational schedule including costs associated with electrical consumption periods (e.g., peak hours, off hours), control 110 may control operation and/or adjust first disinfecting light fixture 102 to provide the majority of disinfecting energy 108 during off-peak hours. Continuing the example above, evening hours (e.g., 10:00 PM to 4:00 AM) may be considered off-peak hours for electrical consumption. As a result, controller 110 may control first disinfecting light fixture 102 to provide the majority of disinfecting energy 108 during evening hours to not only meet and/or maintain a minimum dosage of disinfecting energy 108 in first space 30, but also to meet and/or maintain an average amount of disinfecting energy 108 over the predetermined amount of time. This in turn may regulate disinfecting energy 108 provided to space 30, while also reducing the cost for operating disinfecting light system 100, as discussed herein.

Although discussed herein as adjusting the operation of first disinfecting light fixture 102 based on data and/or information determined by each sensor 112, 118, 120A, 120B, 120C and/or access control component 126, it is understood that controller 110 of control system 109 may adjust the operation of first disinfecting light fixture 102 based on a variety or plurality of data and/or information. In the non-limiting example shown in FIG. 1, and as similarly discussed herein, controller 110 may receive and process the measured amount of disinfecting energy 108 from first sensor 112 and a corresponding disinfecting energy threshold, and the bacterial load for first space 30 sensed by second sensor 118 and a corresponding bacterial load threshold. Additionally, controller 110 may receive and process environmental characteristic(s) (e.g., occupancy level, visible light, task(s), and so on) detected by third sensors 120A, 120B, 120C and a corresponding preferred amount of disinfecting energy for each of the detected environmental characteristic(s). Furthermore, controller 110 may receive and process schedule data and scheduled amount of disinfecting energy associated with the schedule data from access control component 126. Once controller 110 receives the data and/or information from a plurality of sensors 112, 118, 120A, 120B, 120C and/or access control component 126, controller 110 may analyze, and/or prioritize all of the data and/or information prior to adjusting the operation of first disinfecting light fixture 102, as discussed herein. That is, controller 110 may prioritize the data and/or information based on the type of data and/or information received and/or the type of sensors 112, 118, 120A, 120B, 120C, and/or access control component 126 included within first space 30, and then may compare the prioritized data. For example, controller 110 may prioritize the sensed bacterial load and corresponding bacterial load threshold (e.g., second sensor 118) over or above the measured amount of disinfecting energy and disinfecting energy threshold (e.g., first sensor 112), environmental characteristic(s) and corresponding preferred amount of disinfecting energy (e.g., third sensors 120A, 120B, 120C), and/or schedule data and the scheduled amount of disinfecting energy (e.g., access control component 126). In the non-limiting example where controller 110 receives the plurality of data from sensors 112, 118, 120A, 120B, 120C, and/or access control component 126, and prioritizes the data relating to the bacterial load sensed by second sensor 118 and the corresponding bacterial load threshold, controller 110 may adjust the operation of, and more specifically the amount of disinfecting energy 108 emitted by, first disinfecting light fixture 102 based solely on the sensed bacterial load and the bacterial load threshold, as discussed herein.

Additionally, or alternatively, once controller 110 prioritizes the data and/or information from a plurality of sensors 112, 118, 120A, 120B, 120C and/or access control component 126, controller 110 may compare the data and/or information. In a non-limiting example, the prioritized bacterial load threshold, and specifically the predetermined, preferred, or required disinfecting energy associated with the bacterial load threshold (e.g., second sensor 118), may be compared to the disinfecting energy threshold (e.g., first sensor 112), the preferred amount of disinfecting energy associated with the environmental characteristic(s) (e.g., third sensor 120A, 120B, 120C), and/or the scheduled amount of disinfecting energy associated with the schedule data (e.g., access control component 126). In comparing the plurality of data and/or information, controller 110 may determine how to adjust the operation, and more specifically adjust disinfecting energy 108, of first disinfecting light fixture 102. For example, the predetermined, preferred, or required disinfecting energy associated with the prioritized bacterial load threshold may be greater than the disinfecting energy threshold, the preferred amount of disinfecting energy associated with the environmental characteristic(s), and/or the scheduled amount of disinfecting energy associated with the schedule data. In this non-limiting example, controller 110 may adjust disinfecting energy 108 provided to first space 30 by first disinfecting light fixture 102 to equal and/or meet the predetermined, preferred, or required disinfecting energy associated with the prioritized bacterial load threshold. By adjusting disinfecting energy 108 emitted by first disinfecting light fixture 102 to equal and/or meet the predetermined, preferred, or required disinfecting energy associated with the prioritized bacterial load threshold, which may be greater than the remaining disinfecting energies associated with the received data and/or information, it may ensure that the other disinfecting energy 108 requirements are also met.

In another non-limiting example, the predetermined, preferred, or required disinfecting energy associated with the prioritized bacterial load threshold may be less than the disinfecting energy threshold, the preferred amount of disinfecting energy associated with the environmental characteristic(s), and/or the scheduled amount of disinfecting energy associated with the schedule data. In this non-limiting example, controller 110 may adjust disinfecting energy 108 provided to first space 30 by first disinfecting light fixture 102 to equal and/or meet the predetermined, preferred, or required disinfecting energy associated with the prioritized bacterial load threshold regardless of the other, greater disinfecting energies associated with the received data and/or information. Alternatively, controller 110 may adjust disinfecting energy 108 provided to first space 30 by first disinfecting light fixture 102 to equal and/or meet the disinfecting energy threshold, the preferred amount of disinfecting energy associated with the environmental characteristic(s), and/or the scheduled amount of disinfecting energy associated with the schedule data, rather than the disinfecting energy associated with the prioritized bacterial load threshold. Controller 110 may do this, even though the disinfecting energy associated with the prioritized bacterial load threshold is prioritized over the other associated disinfecting energies. By adjusting disinfecting energy 108 emitted by first disinfecting light fixture 102 to equal and/or meet the disinfecting energy threshold, the preferred amount of disinfecting energy associated with the environmental characteristic(s), and/or the scheduled amount of disinfecting energy associated with the schedule data, it may ensure that both the disinfecting energy associated with the prioritized bacterial load threshold, as well as at least one additional, associated disinfecting energy is met.

Although discussed herein as being prioritized, and consequently adjusted, based on the bacterial load and associated disinfecting energy, it is understood that controller 110 may also consider additional information when prioritizing data and/or information for disinfecting light system 100. For example, in addition to prioritizing the data and/or information based on bacterial load and associated disinfecting energy, controller 110 may also consider energy consumption and/or cost associated with electrical consumption periods when prioritizing the data and/or information. In another non-limiting example, controller 110 may also consider illumination quality and/or lumen output by first disinfecting light fixture 102, in addition to bacterial load and associated disinfecting energy, when prioritizing the data and/or information received by controller 110 relating to disinfecting light system 100.

Furthermore, controller 110 configured to control and/or adjust the operation of first disinfecting light fixture 102 (e.g., adjust illuminating light 106, disinfecting energy 108) may also be configured to store past data and/or information relating to first space 30, sensors 112, 118, 120A, 120B, 120C, and/or access control component 126. Specifically, controller 110 may store past data, learn/adapt/compare past data, and adjust data relating to first space 30 based on the learned/adapted/compared past data. For example, and as discussed herein, controller 110 may utilize the learned or anticipated information relating to the probability or likeliness that first space 30 may experience an unscheduled or unplanned interruption, and may control the operation of first disinfecting light fixture 102 in the fail-safe manner discussed herein to meet the amount of disinfecting energy 108 over the predetermined amount of time. In another non-limiting example, controller 110 over time may identify or learn that a previously identified task by third sensor 120C may require more disinfecting energy 108 than the preferred amount of disinfecting energy originally associated with the identified task. Controller 110 may learn this over time by constantly determining that when the task is identified and the disinfecting energy 108 of first disinfecting light fixture 102 is adjusted to the preferred amount of disinfecting energy associated with the identified task, the sensed bacterial load is still above the bacterial load threshold. Alternatively, controller 110 may learn that the preferred amount of disinfecting energy originally associated with the identified task is inadequate as a result of the user(s) performing the identified task in first space 30 consistently adjusting (e.g., increasing) the amount of disinfecting energy 108 using access control component 126. In non-limiting examples, controller 110 may learn, as discussed herein, using various feedback loop possibilities including, but not limited to, proportional control algorithms, or a Proportional-Integral-Derivative (PID) feedback loop.

Although discussed herein with respect to first space 30, and the sensors 112, 118, 120A, 120B, 120C of control system 109 positioned within first space 30, it is understood that the components of disinfecting light system 100 may function and/or operate substantially similar within second space 32. That is, and as shown in the non-limiting example of FIG. 1, second space 32 may include second disinfecting light fixture 104 which may be configured to provide illuminating light 106 and/or disinfecting energy 108 to second space 32, and more specifically workstation 26 included within second space 32. Additionally, second disinfecting light fixture 104 may be operably coupled to controller 110 of control system 109. As similarly discussed herein with respect to first disinfecting light fixture 102 and first space 30, controller 110 may receive data from fourth sensor 122 and fifth sensor 124 included within second space 32 (e.g., positioned on workstation 26), and adjust illuminating light 106 and/or disinfecting energy 108 provided to second space 32 by second disinfecting light fixture 104. Fourth sensor 122 and fifth sensor 124 positioned within second space 32 may be substantially similar to first sensor 112 and second sensor 118, respectively, positioned within first space 30. That is, fourth sensor 122 may be any suitable sensor capable of measuring an amount of disinfecting energy 108 provided to second space 32 by second disinfecting light fixture 104 of disinfecting light system 100. Additionally, fifth sensor 124 may be any suitable sensor capable of sensing bacterial load, bioburden, and/or microbial load within second space 32 of environment 10. Redundant explanation of these components has been omitted for clarity.

In the non-limiting example shown in FIG. 1, second space 32 may not include any third sensors 120A, 120B, 120C configured as environmental characteristic sensors, and/or may be sensors configured to measure or detect environmental characteristics of second space 32 of environment 10. However, because second space 32 is included within first space 30, controller 110, configured to adjust illuminating light 106 and/or disinfecting energy 108 provided to second space 32 by second disinfecting light fixture 104, may utilize environmental characteristic data measured, obtained, sensed, and/or identified by third sensors 120A, 120B, 120C positioned within first space 30. That is, the information obtained by third sensors 120A, 120B, 120C and provided to controller 110 for adjusting illuminating light 106 and/or disinfecting energy 108 provided to first space 30 by first disinfecting light fixture 102 may also be utilized to by controller 110 to adjust illuminating light 106 and/or disinfecting energy 108 provided to second space 32 by second disinfecting light fixture 104. This may be because environmental characteristics that apply to first space 30 (e.g., occupancy level) may also affect and/or be the same for second space 32. In another non-limiting example (not shown), second space 32 may include at least one additional sixth sensor that is substantially similar to third sensors 120A, 120B, 120C of first space 30. That is, the sixth sensor(s) included within second space 32 may be configured as environmental characteristic sensors, and/or may be sensors configured to measure or detect environmental characteristics of second space 32 of environment 10.

Figure 2:
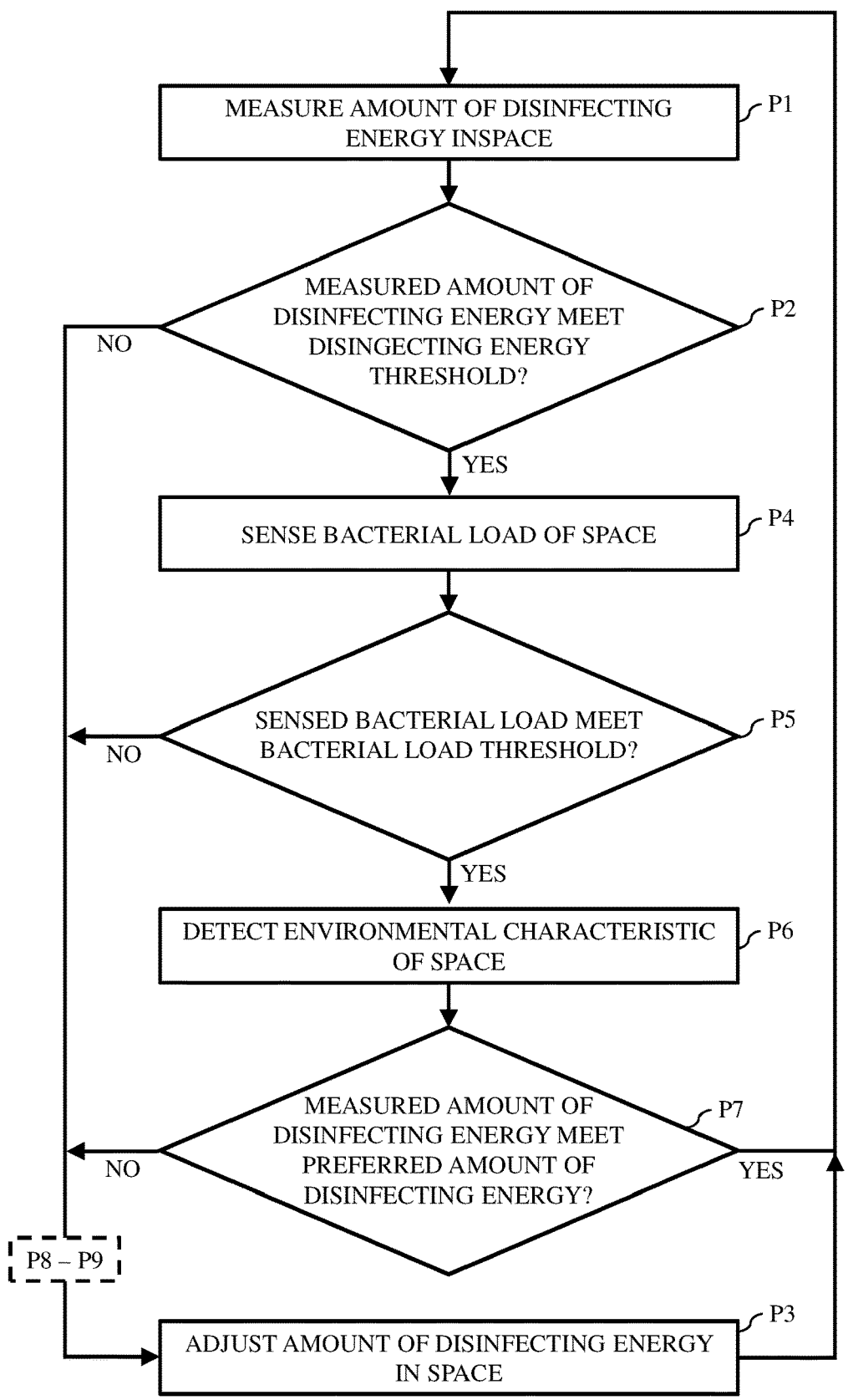
FIG. 2 shows a flow chart of example processes for regulating disinfecting energy generated by a disinfecting light system within a space, according to embodiments of the disclosure.

FIG. 2 shows a flow diagram illustrating non-limiting example processes of regulating disinfecting energy 108 generated by a disinfecting light system 100 within space(s) 30, 32 of environment 10. These processes can be performed, e.g., by at least one controller 110 of control system 109 for disinfecting light system 100 (see, FIG. 1), as described herein. In other cases, these processes can be performed according to a computer-implemented method of regulating disinfecting energy 108 generated by a disinfecting light system 100 within space(s) 30, 32 of environment 10. In still other embodiments, these processes can be performed by executing computer program code on a computing device(s), causing the computing device(s), and specifically controller 110, to regulate disinfecting energy 108 generated by a disinfecting light system 100 within space(s) 30, 32 of environment 10. The processes shown in the flow diagram of FIG. 2 are discussed in detail below.

In process P1, an amount of disinfecting energy in a space of an environment may be measured. Specifically, an amount of disinfecting energy provided to the space of the environment by a disinfecting light fixture of a disinfecting light system may be measured, sensed, detected and/or determined. The measured amount of energy provided to the space of the environment by the disinfecting light fixture of the disinfecting light system may be measured by at least one sensor positioned within the space receiving the disinfecting energy. In another non-limiting example, the measured amount of disinfecting energy provided to the space of the environment by the disinfecting light fixture of the disinfecting light system may be measured, sensed, provided, and/or determined by the disinfecting light fixture itself. That is, the disinfecting light fixture may sense, provide, and/or determine the amount of disinfecting energy it emits or provides to the space.

In process P2, the measured amount of disinfecting energy provided to the space of the environment may be compared to a predetermined disinfecting energy threshold to determine if the measured amount of disinfecting energy meets the disinfecting energy threshold. Specifically, it may be determined if the measured amount of disinfecting energy, provided to the space by the disinfecting light fixture of the disinfecting light system and measured or determined (e.g., sensor(s), disinfecting light fixture) within the space, meets the disinfecting energy threshold. The predetermined disinfecting energy threshold may be a predetermined or desired amount, level, minimum, and/or range of disinfecting energy to be provided to the space. That is, the predetermined disinfecting energy threshold may be based on maintaining the predetermined or desired amount, level, minimum, and/or range of disinfecting energy to be provided to the space. The predetermined or desired amount, level, minimum, and/or range of disinfecting energy to be provided to the space may be an instant or real-time desired amount of disinfecting energy, or alternatively, may be a desired amount of disinfecting energy provided over a predetermined period of time (e.g., daily dosage). In another non-limiting example, the predetermined disinfecting energy threshold may be configured to maintain a predetermined average disinfection amount, level and/or range of the disinfecting energy provided to space over a predetermined time.

In a non-limiting example, the measured amount of disinfecting energy meets the disinfecting energy threshold when it is equal to or within the range of the desired, disinfecting energy to be provided to the space. The controller of the control system for the disinfecting light system may determine if the measured amount of disinfecting energy meets the disinfecting energy threshold. If it is determined that the measured amount of disinfecting energy does not meet the disinfecting energy threshold (e.g., "NO" at process P2), the processes may proceed to process P3. Conversely, if it is determined that the measured amount of disinfecting energy does meet the disinfecting energy threshold (e.g., "YES" at process P2), the processes may proceed to process P4.

In response to determining the measured amount of disinfecting energy does not meet the disinfecting energy threshold (e.g., "NO" at process P2), the amount of disinfecting energy in the space may be adjusted in process P3. That is, in process P3, the amount of disinfecting energy provided to the space by the disinfecting light fixture of the disinfecting light system may be adjusted, changed, and/or altered. The amount of disinfecting energy provided to the space may be adjusted by altering the operation of the disinfecting light fixture to one of increase or decrease the amount of disinfecting energy generated by the disinfecting light fixture and provided to the space. In a non-limiting example, the controller of the control system for the disinfecting light system may be operably coupled to the disinfecting light fixture and may be configured to control the operation of disinfecting light fixture to adjust (e.g., increase, decrease) the amount of disinfecting energy generated by the disinfecting light fixture. The controller of the control system may adjust the amount of disinfecting energy generated by the disinfecting light fixture independent of the amount of illuminating light provided to the space by the disinfecting light fixture. That is, the amount of disinfecting energy generated by the disinfecting light fixture may be adjusted, while the amount of illuminating light provided to the space by the disinfecting light fixture remains substantially the same. The amount of disinfecting energy provided to the space may be adjusted by the controller of the control system to maintain a predetermined or desired amount, level, minimum, and/or range of disinfecting energy to be provided to the space over a predetermined period of time. Additionally, or alternatively, adjusting the amount of disinfecting energy provided to the space may include maintaining a predetermined average disinfection amount, level, and/or range of the disinfecting energy provided to space over a predetermined time. Furthermore, the amount of disinfecting energy generated by the disinfecting light fixture can be altered or adjusted by increasing or decreasing the brightness or dynamically changing the violet content of the illuminating light provided to the space by the disinfecting light fixture. That is, in another non-limiting example, the amount of disinfecting energy generated by the disinfecting light fixture may be adjusted by adjusting and/or changing the amount of illuminating light generated by the disinfecting light fixture.

In a non-limiting example where the measured amount of disinfecting energy is less than the disinfecting energy threshold, the controller may increase the amount of disinfecting energy provided to the space by the disinfecting light fixture until the measured amount of disinfecting energy meets the disinfecting energy threshold. Additionally in a non-limiting example where the measured amount of disinfecting energy is greater than the disinfecting energy threshold, the controller may decrease or maintain the amount of disinfecting energy provided to the space by the disinfecting light fixture until the measured amount of disinfecting energy meets the disinfecting energy threshold. Alternatively in the non-limiting example where the measured amount of disinfecting energy is greater than the disinfecting energy threshold, the controller may stop the disinfecting light fixture from generating and providing disinfecting energy to the space until the measured amount of disinfecting energy meets the disinfecting energy threshold. As discussed herein, the amount of disinfecting energy generated by the disinfecting light fixture may be adjusted and/or changed independent of the amount of illuminating light provided to the space by the disinfecting light fixture.

In response to determining the measured amount of disinfecting energy meets the disinfecting energy threshold (e.g., "YES" at process P2), a bacterial load of the space may be sensed in process P4. Specifically, a bacterial load of the space of the environment may be sensed, measured, detected, and/or determined. The sensed bacterial load of the space of the environment may be sensed and/or detected by at least one sensor positioned within the space. In another non-limiting example, the sensed bacterial load of the space of the environment may be determined and/or calculated using a correlated measurement.

In process P5, the sensed bacterial load of the space may be compared to a bacterial load threshold to determine if the sensed bacterial load meets the bacterial load threshold. Specifically, it may be determined if the sensed bacterial load for the space, as detected or sensed by the sensor(s) within the space, meets the predetermined bacterial load threshold. The predetermined, bacterial load threshold may be a predetermined or desired amount, level, maximum, and/or range for an acceptable bacterial load of the space. That is, the predetermined bacterial load threshold for the space may be based on maintaining the predetermined or desired amount, level, maximum, and/or range of bacterial load within the space. In another non-limiting example, the predetermined bacterial threshold may be based on maintaining a predetermined average bacterial load amount, level, and/or range of the space over a predetermined time.

In a non-limiting example, the sensed bacterial load meets the predetermined bacterial load threshold when it is equal to or within the range of the desired, bacterial load for the space. The controller of the control system for the disinfecting light system may determine if the sensed bacterial load meets the bacterial load threshold. If it is determined that the sensed bacterial load does not meet the bacterial load threshold (e.g., "NO" at process P5), the processes may proceed to process P3. Conversely, if it is determined that the sensed bacterial load does meet the bacterial load threshold (e.g., "YES" at process P5), the processes may proceed to process P6.

In response to determining the sensed bacterial load does not meet the bacterial load threshold (e.g., "NO" at process P5), the amount of disinfecting energy in the space may be adjusted in process P3. That is, in process P3, the amount of disinfecting energy provided to the space by the disinfecting light fixture of the disinfecting light system may be adjusted, changed, and/or altered. As similarly discussed herein, the controller of the control system for the disinfecting light system may be operably coupled to the disinfecting light fixture and may be configured to control the operation of disinfecting light fixture to adjust (e.g., increase, decrease) the amount of disinfecting energy generated by the disinfecting light fixture and provided to the space. As discussed herein, the disinfecting energy generated by the disinfecting light fixture may alter, adjust, and/or control the bacterial load, bioburden, and/or microbial load within the space receiving the disinfecting energy. In a non-limiting example where the sensed bacterial load is greater than the bacterial load threshold, the controller may increase the amount of disinfecting energy provided to the space by the disinfecting light fixture until the sensed bacterial load meets the bacterial load threshold. Additionally in a non-limiting example where the sensed bacterial load is less than the bacterial load threshold, the controller may decrease or maintain the amount of disinfecting energy provided to the space by the disinfecting light fixture until the sensed bacterial load meets the bacterial load threshold. Alternatively in the non-limiting example where the sensed bacterial load is less than the bacterial load threshold, the controller may stop the disinfecting light fixture from generating the disinfecting energy until the sensed bacterial load meets the bacterial load threshold. The amount of disinfecting energy generated by the disinfecting light fixture may be adjusted and/or changed independent of the amount of illuminating light provided to the space by the disinfecting light fixture.

In response to determining the sensed bacterial load meets the bacterial load threshold (e.g., "YES" at process P5), an environmental characteristic(s) of the space may be detected in process P6. Specifically in process P6, an environmental characteristic(s) related to and/or associated with the space including the disinfecting light system may be detected. The environmental characteristic(s) of the space may be sensed and/or detected by at least one sensor positioned within the space. In another non-limiting example, the environmental characteristic(s) of the space may be sensed and/or detected by additional components included within the environment and/or the control system including, but not limited to, an access control component. In an additional non-limiting example, the environmental characteristic(s) of the space may be determined and/or provided by a manual input provided by a user(s) of the space in the environment. The detected environmental characteristic may include and/or be based upon an occupancy level of the space (e.g., if the space is occupied, the number of users that may occupy the space, a change in user-occupancy for the space) being provided the disinfecting energy by the disinfecting light fixture. In another non-limiting example, the detected environmental characteristic may include and/or be based upon an amount of natural light in the space, and/or a predetermined amount of natural disinfecting energy associated with and/or included within or provided with the natural light. In an additional non-limiting example, the detected environmental characteristic may include and/or be based upon at least one task being carried out in the space.

In addition to detecting the environmental characteristic(s) in process P6, a preferred amount of disinfecting energy associated with the detected environmental characteristic(s) may be identified. That is, detecting the environmental characteristic(s) in process P6 may also include identifying a preferred amount of disinfecting energy associated with detected environmental characteristics that may be provided to the space by the disinfecting light fixture of the disinfecting light system. The preferred amount of disinfecting energy associated with the detected environmental characteristic(s) may be predefined and/or predetermined based on the environmental characteristic(s) and/or characteristics of the space provided the disinfecting energy. In non-limiting examples, the preferred amount of disinfecting energy associated with the detected environmental characteristic(s) may be stored on the controller of the control system, or may be provided to the controller from an external source (e.g., storage device), such that when the detected environmental characteristic(s) is provided to the controller of the control system, the preferred amount of disinfecting energy associated with detected environmental characteristics may also be provided to and/or recognized by the controller.

The preferred amount of disinfecting energy associated with detected environmental characteristics may be based on, related to, and/or associated with the space provided the disinfecting light. For example, the preferred amount of disinfecting energy associated with the detected occupancy level of the space may include various preferred amounts of disinfecting energy based upon distinct occupancy levels of the space. In another non-limiting example, the preferred amount of disinfecting energy associated with the detected natural light in the space and/or the amount of natural disinfecting energy associated with the natural light, may include various preferred amounts of disinfecting energy based upon the amount of natural light and/or natural disinfecting energy in the space. In an additional non-limiting example, the preferred amount of disinfecting energy associated with the detected task carried out in the space may include various preferred amounts of disinfecting energy based upon various tasks being carried out in the space.

In process P7, it may be determined if the measured amount of disinfecting energy provided to the space by the disinfecting light system meets the preferred amount of disinfecting energy associated with the detected, environmental characteristic(s). Specifically, it may be determined if the measured amount of disinfecting energy provided to the space by the disinfecting light system (e.g., process P1) meets the preferred amount of disinfecting energy associated with the detected, environmental characteristic(s) (e.g., process P6). In a non-limiting example, the measured amount of disinfecting energy provided to the space by the disinfecting light system meets the preferred amount of disinfecting energy associated with the detected, environmental characteristic(s) when it is equal to or within the range of the preferred amount of disinfecting energy associated with the detected, environmental characteristic. The controller of the control system for the disinfecting light system may determine if the measured amount of disinfecting energy provided to the space by the disinfecting light system meets the preferred amount of disinfecting energy associated with the detected, environmental characteristic(s). If it is determined that the measured amount of disinfecting energy provided to the space does not meet the preferred amount of disinfecting energy associated with the detected, environmental characteristic(s) (e.g., "NO" at process P7), the processes may proceed to process P3. Conversely, if it is determined that the measured amount of disinfecting energy provided to the space does meet the preferred amount of disinfecting energy associated with the detected, environmental characteristic(s) (e.g., "YES" at process P7), the processes repeat and/or may proceed back to process P1 and may begin again.

In response to determining the measured amount of disinfecting energy provided to the space does not meet the preferred amount of disinfecting energy associated with the detected, environmental characteristic(s) (e.g., "NO" at process P6), the amount of disinfecting energy in the space may be adjusted in process P3. That is, in process P3, the amount of disinfecting energy provided to the space by the disinfecting light fixture of the disinfecting light system may be adjusted, changed, and/or altered. The amount of disinfecting energy provided to the space may be adjusted by altering the operation of the disinfecting light fixture to one of increase or decrease the amount of disinfecting energy generated by the disinfecting light fixture and provided to the space. In a non-limiting example, the controller of the control system for the disinfecting light system may be operably coupled to the disinfecting light fixture and may be configured to control the operation of disinfecting light fixture to adjust (e.g., increase, decrease) the amount of disinfecting energy generated by the disinfecting light fixture. In a non-limiting example where the measured amount of disinfecting energy is less than the preferred amount of disinfecting energy associated with the detected, environmental characteristic(s) (e.g., occupancy level, natural light, natural disinfecting energy, task(s)), the controller may increase the amount of disinfecting energy provided to the space by the disinfecting light fixture until the measured amount of disinfecting energy meets the preferred amount of disinfecting energy. Additionally in a non-limiting example where the measured amount of disinfecting energy is greater than the preferred amount of disinfecting energy associated with the detected, environmental characteristic(s) (e.g., occupancy level, natural light, natural disinfecting energy, task(s)), the controller may decrease or maintain the amount of disinfecting energy provided to the space by the disinfecting light fixture until the measured amount of disinfecting energy meets the preferred amount of disinfecting energy. Alternatively in the non-limiting example where the measured amount of disinfecting energy is greater than the preferred amount of disinfecting energy associated with the detected, environmental characteristic(s), the controller may stop the disinfecting light fixture from generating and providing disinfecting energy to the space until the measured amount of disinfecting energy meets the preferred amount of disinfecting energy. The amount of disinfecting energy generated by the disinfecting light fixture may be adjusted and/or changed independent of the amount of illuminating light provided to the space by the disinfecting light fixture.

Although shown in succession, it is understood that some of the processes illustrated in FIG. 2 for regulating the disinfecting energy generated by the disinfecting light system may be performed concurrently. For example, processes P1 and P4 may be performed concurrently, and subsequent processes P2 and P5 may also be performed concurrently after performing processes P1 and P4. Additionally, it is understood that the order in which at least some of the processes of FIG. 2 for regulating the disinfecting energy are performed is illustrative. As such, some of the processes may be performed in a distinct order than that shown in the non-limiting example of FIG. 2. For example, processes P4 and P5 may be performed prior to performing processes P1 and P2. Additionally, or alternatively, processes P6 and P7 may be performed prior to performing processes P4 and P5.

Additionally, the processes for regulating the disinfecting energy generated by the disinfecting light system may be performed independent of the operation and/or adjustment of the illuminating light generated by the disinfecting light system. That is, regulating the disinfecting energy by adjusting the amount of disinfecting energy provided to the space by the disinfecting light fixture may be performed independent of adjusting the amount of the illuminating light. The controller of the control system may adjust the amount of the illuminating light provided to space by the disinfecting light fixture based on the preferred amount of illuminating light that may be associated with the detected, environmental characteristics of the space and/or manually provided to the control system.

Figure 3:
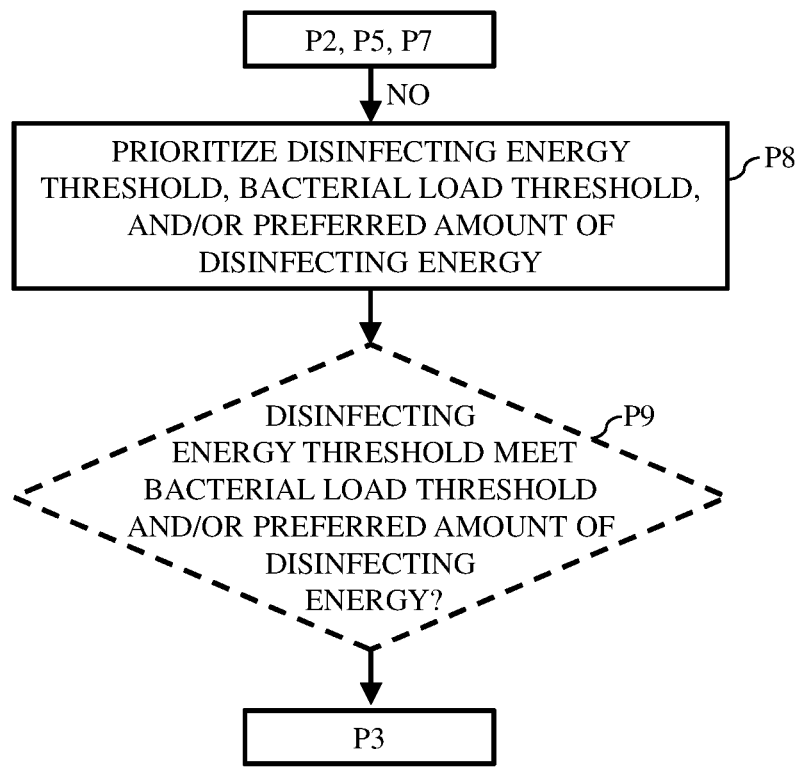
FIG. 3 shows a flow chart of example additional processes for regulating disinfecting energy generated by a disinfecting light system within a space as shown in FIG. 2, according to embodiments of the disclosure.

FIG. 3 shows a flow diagram illustrating additional non-limiting example processes of regulating disinfecting energy 108 generated by a disinfecting light system 100 within space(s) 30, 32 of environment 10. Specifically, FIG. 3 shows a flow diagram illustrating processes P8 and P9, which may be performed with process P1-P7 discussed herein with respect to FIG. 2. These processes can be performed, e.g., by at least one controller 110 of control system 109 for disinfecting light system 100 (see, FIG. 1), as described herein. In other cases, these processes can be performed according to a computer-implemented method of regulating disinfecting energy 108 generated by a disinfecting light system 100 within space(s) 30, 32 of environment 10. In still other embodiments, these processes can be performed by executing computer program code on a computing device(s), causing the computing device(s), and specifically controller 110, to regulate disinfecting energy 108 generated by a disinfecting light system 100 within space(s) 30, 32 of environment 10. The processes shown in the flow diagram of FIG. 3 are discussed in detail below.

In response to the controller receiving and/or obtaining a variety or plurality of data and/or information from various sensors and/or components of the disinfecting light system, additionally processes may be performed before adjusting the amount of disinfecting energy provided to the space by the disinfecting light fixture. Specifically, and continuing from the non-limiting examples of processes P1-P7, the controller may receive and process the measured amount of the disinfecting energy from the first sensor, and the corresponding disinfecting energy threshold (e.g., processes P1 and P2), and the bacterial load for the space sensed by the second sensor and a corresponding bacterial load threshold (e.g., processes P4 and P5). Additionally, the controller may receive and process environmental characteristic(s) (e.g., occupancy level, visible light, task(s), and so on) detected by third sensor(s) and a corresponding preferred amount of disinfecting energy for each of the detected environmental characteristic(s). In this non-limiting example, and as shown in FIG. 3, process P8 may be performed before adjusting the amount of disinfecting energy provided to the space in process P3.

In process P8, the variety or plurality of data and/or information relating to the space may be prioritized. That is, the variety or plurality of data and/or information from various sensors and/or components of the disinfecting light system relating to the space may be prioritized, ordered, weighted, arranged, and/or ranked in process P8. In a non-limiting example, the controller may prioritize the data and/or information based on the type of data and/or information received and/or the type of sensors, and/or the component(s) included within the space 30, and/or by the importance of the data and/or information with respect to the disinfecting light system. For example, the controller may prioritize the sensed bacterial load and corresponding bacterial load threshold (e.g., processes P4 and P5) over, higher than, and/or above the measured amount of disinfecting energy and disinfecting energy threshold (e.g., processes P1 and P2), and/or the environmental characteristic(s) and corresponding preferred amount of disinfecting energy (e.g., processes P6 and P7). In a non-limiting example, once the controller prioritizes the data relating to the bacterial load and the corresponding bacterial load threshold above the other data and/or information relating to the space, the controller may adjust the amount of disinfecting energy as discussed herein with respect to process P3.

In process P9 (shown in phantom as optional), the prioritized variety or plurality of data and/or information relating to the space may be compared. That is, the prioritized variety or plurality of data and/or information from various sensors and/or components of the disinfecting light system relating to the space may be compared in one another in process P9 to determine if the prioritized data and/or information meets the other data and/or information. For example, the prioritized bacterial load threshold, and specifically the predetermined, preferred, or required disinfecting energy associated with the bacterial load threshold prioritized in process P8, may be compared to the disinfecting energy threshold and/or, the preferred amount of disinfecting energy associated with the environmental characteristic(s). In comparing the plurality of data and/or information, it may be determined how to adjust the disinfecting energy provided to the space in process P3. In a non-limiting example, the disinfecting energy associated with the prioritized bacterial load threshold may be greater than the disinfecting energy threshold, and/or the preferred amount of disinfecting energy associated with the environmental characteristic(s). In this non-limiting example, the disinfecting energy provided to the space by the disinfecting light fixture may be adjusted to equal and/or meet the disinfecting energy associated with the prioritized bacterial load threshold.

In another non-limiting example, the disinfecting energy associated with the prioritized bacterial load threshold may be less than the disinfecting energy threshold, and/or the preferred amount of disinfecting energy associated with the environmental characteristic(s). In this non-limiting example, the disinfecting energy provided to the space by the disinfecting light fixture may be adjusted to equal and/or meet the disinfecting energy associated with the prioritized bacterial load threshold regardless of the other, greater disinfecting energies associated with the received data and/or information. Alternatively in this non-limiting example, the disinfecting energy provided to the space by the disinfecting light fixture may be adjusted to equal and/or meet the disinfecting energy threshold, and/or the preferred amount of disinfecting energy associated with the environmental characteristic(s), rather than the disinfecting energy associated with the prioritized bacterial load threshold. The amount of disinfecting energy may be adjusted in this manner, even though the disinfecting energy associated with the prioritized bacterial load threshold is prioritized over the disinfecting energy threshold, and/or the preferred amount of disinfecting energy associated with the environmental characteristic(s). By adjusting the disinfecting energy emitted by the disinfecting light fixture to equal and/or meet the disinfecting energy threshold, and/or the preferred amount of disinfecting energy associated with the environmental characteristic(s), it may ensure that both the disinfecting energy associated with the prioritized bacterial load threshold, as well as at least one additional, associated disinfecting energy is met.

Figure 4:
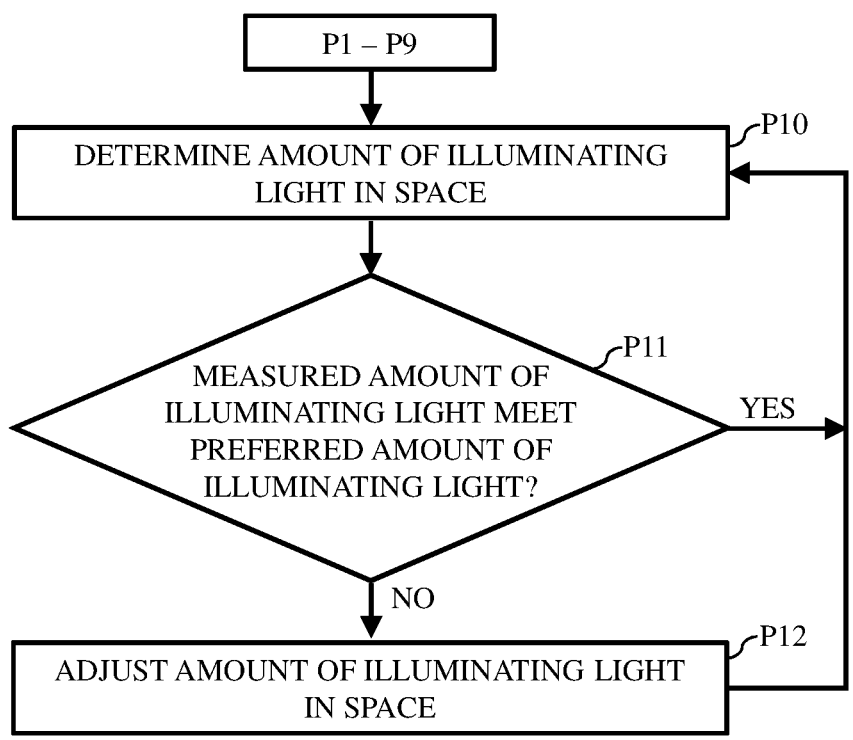
FIG. 4 shows a flow chart of example processes for regulating illuminating light generated by a disinfecting light system within a space, according to embodiments of the disclosure.

FIG. 4 shows a flow diagram illustrating non-limiting example processes of regulating illuminating light 106 generated by a disinfecting light system 100 within space(s) 30, 32 of environment 10 (see, FIG. 1). These processes can be performed, e.g., by at least one controller 110 of control system 109 for disinfecting light system 100 (see, FIG. 1), as described herein. In other cases, these processes can be performed according to a computer-implemented method of regulating illuminating light 106 generated by a disinfecting light system 100 within space(s) 30, 32 of environment 10. In still other embodiments, these processes can be performed by executing computer program code on a computing device(s), causing the computing device(s), and specifically controller 110, to regulate illuminating light 106 generated by a disinfecting light system 100 within space(s) 30, 32 of environment 10.

In process P10, an amount of illuminating light in a space of an environment may be determined. Specifically, an amount of illuminating light provided to the space of the environment by a disinfecting light fixture of a disinfecting light system (and/or natural light) may be measured, sensed, detected, and/or determined. The measured amount of illuminating light provided to the space of the environment by the disinfecting light fixture of the disinfecting light system may be measured by at least one sensor positioned within the space receiving the illuminating light. In another non-limiting example, the measured amount of illuminating light provided to the space of the environment by the disinfecting light fixture of the disinfecting light system may be measured, sensed, provided, and/or determined by the disinfecting light fixture itself. That is, the disinfecting light fixture may sense, provide, and/or determine the amount of illuminating light it emits or provides to the space. Additionally, and where applicable, determining the amount of illuminating light in the space of the environment may include determining how much of a total visible light provided to the space is illuminating light provided by the disinfecting light fixture, and how of the total visible light is natural light provided to the space.

In addition to determining the amount of illuminating light in process P10, a preferred amount of illuminating light may be identified. That is, determining the amount of illuminating light provided to the space in process P10 may also include identifying a preferred amount of illuminating light. The preferred illuminating light may be based on sensed or measured characteristics of the space (e.g., occupancy level, amount of natural light/natural disinfecting light, task(s), and so on), characteristics and/or properties of the space, predetermined information (e.g., scheduled outputs) for space, and/or information or input manually provided by a user of the disinfecting light system. For example, detecting the environmental characteristic(s) in process P6 may also include identifying a preferred amount of illuminating light associated with detected environmental characteristics that may be provided to the space by the disinfecting light fixture of the disinfecting light system. The preferred amount of illuminating light associated with the detected environmental characteristic(s) may be predefined and/or predetermined based on the environmental characteristic(s) and/or characteristics of the space provided the illuminating light. In non-limiting examples, the preferred amount of illuminating light associated with the detected environmental characteristic(s) may be stored on the controller of the control system, or may be provided to the controller from an external source (e.g., storage device), such that when the detected environmental characteristic(s) is provided to the controller of the control system, the preferred amount of illuminating light associated with detected environmental characteristics may also be provided to and/or recognized by the controller.

The preferred amount of illuminating light associated with detected environmental characteristics may be based on, related to, and/or associated with the space provided the illuminating light. For example, the preferred amount of illuminating light associated with the detected natural light, natural disinfecting energy, illuminating light, and/or total visible light in the space, may include various preferred amounts of illuminating light based upon the amount of natural light, natural disinfecting energy, and current illuminating light being provided to the space. In an additional non-limiting example, the preferred amount of illuminating light associated with the detected task carried out in the space may include various preferred amounts of illuminating light based upon various tasks being carried out in the space.

In another non-limiting example where the preferred amount of illuminating light is based on a predetermined operational schedule, various preferred amounts of illuminating light may be provided based on a variety of information pertaining to the predetermined operational schedule. That is, various preferred amounts of illuminating light may be provided, and may be based on and/or associated with predetermined times of the day (e.g., evening hours), days of the week (e.g., weekends), and/or electrical consumption periods (e.g., peak hours, off-peak hours).

In process P11, it may be determined if the determined amount of illuminating light provided to the space by the disinfecting light system meets the preferred amount of illuminating light. Specifically, it may be determined if the determined amount of illuminating light provided to the space by the disinfecting light system (e.g., process P10) meets the preferred amount of illuminating light associated with, for example, the detected, environmental characteristic(s) and/or the predetermined operational schedule (e.g., process P6). In a non-limiting example, the determined amount of illuminating light provided to the space by the disinfecting light system meets the preferred amount of illuminating light when the determined amount of illuminating light is equal to or within the range of the preferred amount of illuminating light. The controller of the control system for the disinfecting light system may determine if the determined amount of illuminating light provided to the space by the disinfecting light system meets the preferred amount of illuminating light (e.g., predetermined or desired amount, level, minimum, and/or range of illuminating light to be provided to the space (real-time/predetermined period of time), average illuminating light amount, level and/or range provided to space over predetermined time). If it is determined that the determined amount of illuminating light provided to the space does not meet the preferred amount of illuminating light (e.g., "NO" at process P11), the processes may proceed to process P12. Conversely, if it is determined that the determined amount of illuminating light provided to the space does meet the preferred amount of illuminating light (e.g., "YES" at process P11), the processes may repeat and/or may proceed back to process P10 and may begin again.

In response to determining the determined amount of illuminating light provided to the space does not meet the preferred amount of illuminating light (e.g., "NO" at process P11), the amount of illuminating light in the space may be adjusted in process P12. That is, in process P12, the amount of illuminating light provided to the space by the disinfecting light fixture of the disinfecting light system may be adjusted, changed, and/or altered. The amount of illuminating light provided to the space may be adjusted by altering the operation of the disinfecting light fixture to one of increase or decrease the amount of illuminating light generated by the disinfecting light fixture and provided to the space. In a non-limiting example, the controller of the control system for the disinfecting light system may be operably coupled to the disinfecting light fixture and may be configured to control the operation of disinfecting light fixture to adjust (e.g., increase, decrease) the amount of illuminating light generated by the disinfecting light fixture. In a non-limiting example where the determined amount of illuminating light is less than the preferred amount of illuminating light, the controller may increase the amount of illuminating light provided to the space by the disinfecting light fixture until the determined amount of illuminating light meets the preferred amount of illuminating light. Additionally in a non-limiting example where the measured amount of illuminating light is greater than the preferred amount of illuminating light, the controller may decrease or maintain the amount of illuminating light provided to the space by the disinfecting light fixture until the measured amount of illuminating light meets the preferred amount of illuminating light. The amount of illuminating light generated by the disinfecting light fixture may be adjusted and/or changed independent of the amount of disinfecting energy provided to the space by the disinfecting light fixture.

As shown in the non-limiting example of FIG. 4, the processes of regulating the illuminating light emitted by the disinfecting light fixture may be performed in succession with and/or after processes P1-P9 for regulating the disinfecting energy emitted by the disinfecting light fixture. Although shown in succession, it is understood that some of the processes illustrated in FIG. 4 for regulating the illuminating light generated by the disinfecting light system may be performed concurrently with the processes for regulating the disinfecting energy. For example, processes P10-P12 may be performed concurrently with processes P1-P9 discussed herein with respect to FIGS. 2 and 3. Alternatively, the processes for regulating the illuminating light generated by the disinfecting light fixtures of the disinfecting light system (e.g., processes P10-P12) may be performed in a separate and/or distinct flow process or procedure than the processes for regulating the disinfecting energy (e.g., processes P1-P9).

Figure 5:
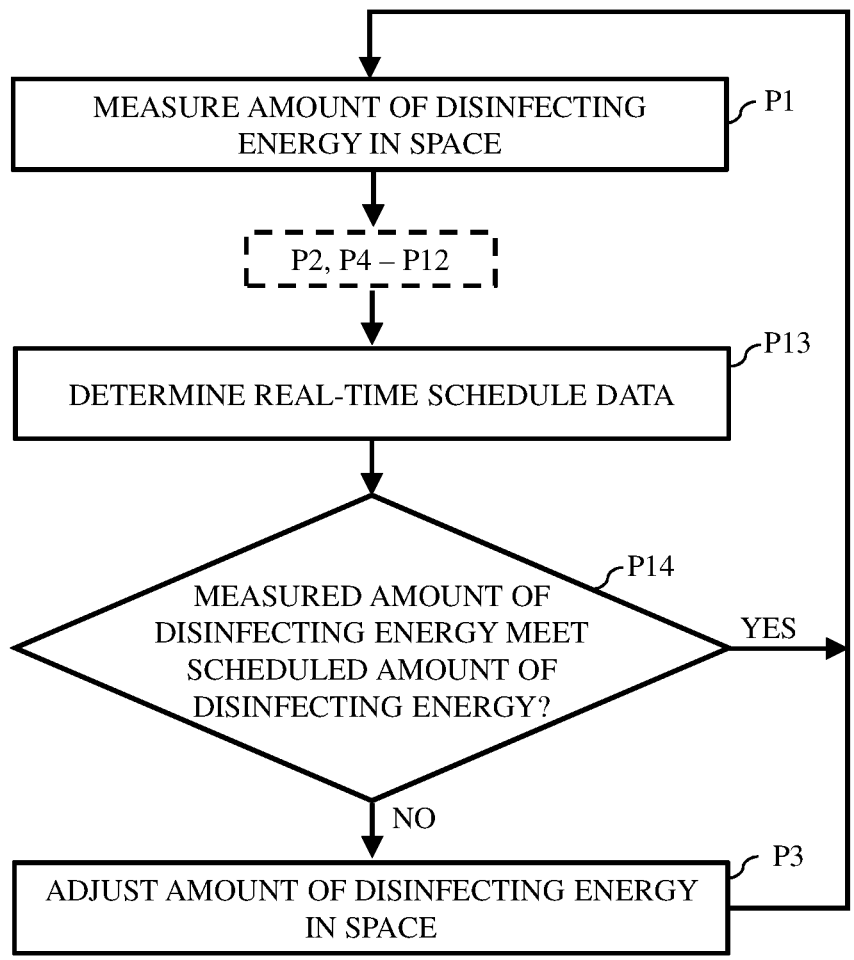
FIG. 5 shows a flow chart of example processes for regulating disinfecting energy generated by a disinfecting light system within a space, according to additional embodiments of the disclosure.

FIG. 5 shows a flow diagram illustrating additional, non-limiting example processes of regulating disinfecting energy 108 generated by a disinfecting light system 100 within space(s) 30, 32 of environment 10 (see, FIG. 1). These processes can be performed, e.g., by at least one controller 110 of control system 109 for disinfecting light system 100 (see, FIG. 1), as described herein. In other cases, these processes can be performed according to a computer-implemented method of regulating disinfecting energy 108 generated by a disinfecting light system 100 within space(s) 30, 32 of environment 10. In still other embodiments, these processes can be performed by executing computer program code on a computing device(s), causing the computing device(s), and specifically controller 110, to regulate disinfecting energy 108 generated by a disinfecting light system 100 within space(s) 30, 32 of environment 10.

Subsequent to measuring the amount of disinfecting energy provided to and/or within the space in process P1, and possibly performing processes P2 and P4-P12), real-time schedule data may be determined in process P13. That is, in process P13 the real-time schedule data may be determined, detected, and/or sensed. The real-time schedule data may relate to data and/or information associated with or pertaining to an operational schedule. That is, the determined real-time schedule data may be based on, associated with, and/or may include a determined time of the day (e.g., 10:00 PM), a determined day of the week (e.g., Saturday), and/or a determined electrical consumption period (e.g., peak hours, off-peak hours). The real-time schedule data may be determined, detected, and/or sensed by a component included within the environment and/or a component in communication with the control system of the disinfecting light system. In a non-limiting example, the real-time schedule data may be determined by an access control component positioned within the environment and in communication with the controller of the control system. In another non-limiting example, the real-time schedule data may be determined by an additional component and/or system utilized by and/or within the environment including, but not limited to, a surveillance system, a security system, an information technology (IT) system, and/or a building management system (BMS)/building automation system (BAS) controlling additional components or systems (e.g., heat, ventilation, and air conditioning (HVAC) systems) of the environment. In an additional non-limiting example, the real-time schedule data may be determined and/or provided by a manual input provided by a user(s) of the space in the environment.

In addition to determining the real-time schedule data in process P13, a scheduled amount of disinfecting energy associated with the real-time schedule data may be identified. That is, determining the real-time schedule data in process P13 may also include identifying a scheduled amount of disinfecting energy, associated with the determined real-time schedule data, which may be provided to the space by the disinfecting light fixture of the disinfecting light system. The scheduled amount of disinfecting energy associated with the determined real-time schedule data may be predefined and/or predetermined based on the predetermined operational schedule (e.g., time of day, day of week, electrical consumption periods, and the like). In a non-limiting example, where the determined real-time schedule data relates to a determined time of day, the scheduled amount of disinfecting energy associated with the real-time schedule data may include various scheduled amounts of disinfecting energy based upon distinct times of the day. In another non-limiting example, where the determined real-time schedule data relates to a determined day of the week, the scheduled amount of disinfecting energy associated with the real-time schedule data may include various scheduled amounts of disinfecting energy based upon each day of the week. In an additional non-limiting example, where the determined real-time schedule data relates to an electrical consumption period, the scheduled amount of disinfecting energy associated with the real-time schedule data may include a first scheduled amount of disinfecting energy corresponding to peak hours, and a second scheduled amount of disinfecting energy corresponding to off-peak hours. Additionally, it is understood that the scheduled amount of disinfecting energy associated with the real-time schedule data may include and/or be based on two (or more) determined data points (e.g., time of day, as well as, day of the week). The scheduled amount of disinfecting energy associated with the determined real-time schedule data may be stored on the controller of the control system, or may be provided to the controller from an external source (e.g., storage device). As such, when the determined real-time schedule data is provided to the controller of the control system, the scheduled amount of disinfecting energy associated with the real-time schedule data may also be provided to and/or recognized by the controller.

In process P14, it may be determined if the measured amount of disinfecting energy provided to the space by the disinfecting light system meets the scheduled amount of disinfecting energy associated with the determined real-time schedule data. Specifically, it may be determined if the measured amount of disinfecting energy provided to the space by the disinfecting light system (e.g., process P1) meets the scheduled amount of disinfecting energy associated with the determined real-time schedule data (e.g., process P13). In a non-limiting example, the measured amount of disinfecting energy provided to the space by the disinfecting light system meets the scheduled amount of disinfecting energy associated with the determined real-time schedule data when it is equal to or within the range of the scheduled amount of disinfecting energy associated with the determined real-time schedule data. The controller of the control system for the disinfecting light system may determine if the measured amount of disinfecting energy provided to the space by the disinfecting light system meets the scheduled amount of disinfecting energy associated with the determined real-time schedule data. If it is determined that the measured amount of disinfecting energy provided to the space does not meet the scheduled amount of disinfecting energy associated with the determined real-time schedule data (e.g., "NO" at process P14), the processes may proceed to process P3. Conversely, if it is determined that the measured amount of disinfecting energy provided to the space does meet the scheduled amount of disinfecting energy associated with the determined real-time schedule data (e.g., "YES" at process P14), the processes repeat and/or may proceed back to process P1 and may begin again.

In response to determining the measured amount of disinfecting energy does not meet the scheduled amount of disinfecting energy associated with the determined real-time schedule data (e.g., "NO" at process P14), the amount of disinfecting energy in the space may be adjusted in process P3. That is, in process P3, the amount of disinfecting energy provided to the space by the disinfecting light fixture of the disinfecting light system may be adjusted, changed, and/or altered. The amount of disinfecting energy in the space may be adjusted in process P3 shown in FIG. 5 in a similar manner and/or fashion as discussed herein with respect to process P3 of FIG. 2. Redundant explanation of this process has been omitted for brevity.

As shown in the non-limiting example of FIG. 5, the additional, non-limiting processes of regulating the disinfecting energy emitted by the disinfecting light fixture may be performed in succession with and/or after processes P1-P9. Although shown in succession, it is understood that some of the processes illustrated in FIG. 5 for regulating the disinfecting energy generated by the disinfecting light system may be performed concurrently with the processes P2 and P4-P7. That is for example, after performing process P1, processes P2 and P13 may be performed concurrently and/or simultaneously. Additionally as shown in FIG. 5, processes P2 and P4-P7 are shown in phantom as optional. In the non-limiting example discussed herein, processes P13 and P14 may be performed subsequent to and/or concurrently with processes P2 and P4-P7 to regulate the disinfecting energy emitted by the disinfecting light fixture of the disinfecting light system. In another non-limiting example, processes P2 and P4-P7 may be omitted, and the disinfecting energy emitted by the disinfecting light fixture may be regulated by only performing processes P1, P13, P14, and P3, in that order.

Additionally, although shown in three distinct flow charts, the processes P1-P14 shown and discussed herein with respect to FIGS. 2-5 may be performed to regulate the operation of the disinfecting light fixture of the disinfecting light system, as discussed herein. That is, the various processes discussed herein (e.g., processes P1-P14) may be performed as single continuous/successive processes, or alternatively simultaneous processes, for regulating the operation of the disinfecting light fixture of the disinfecting light system, as discussed herein.

Figure 6:
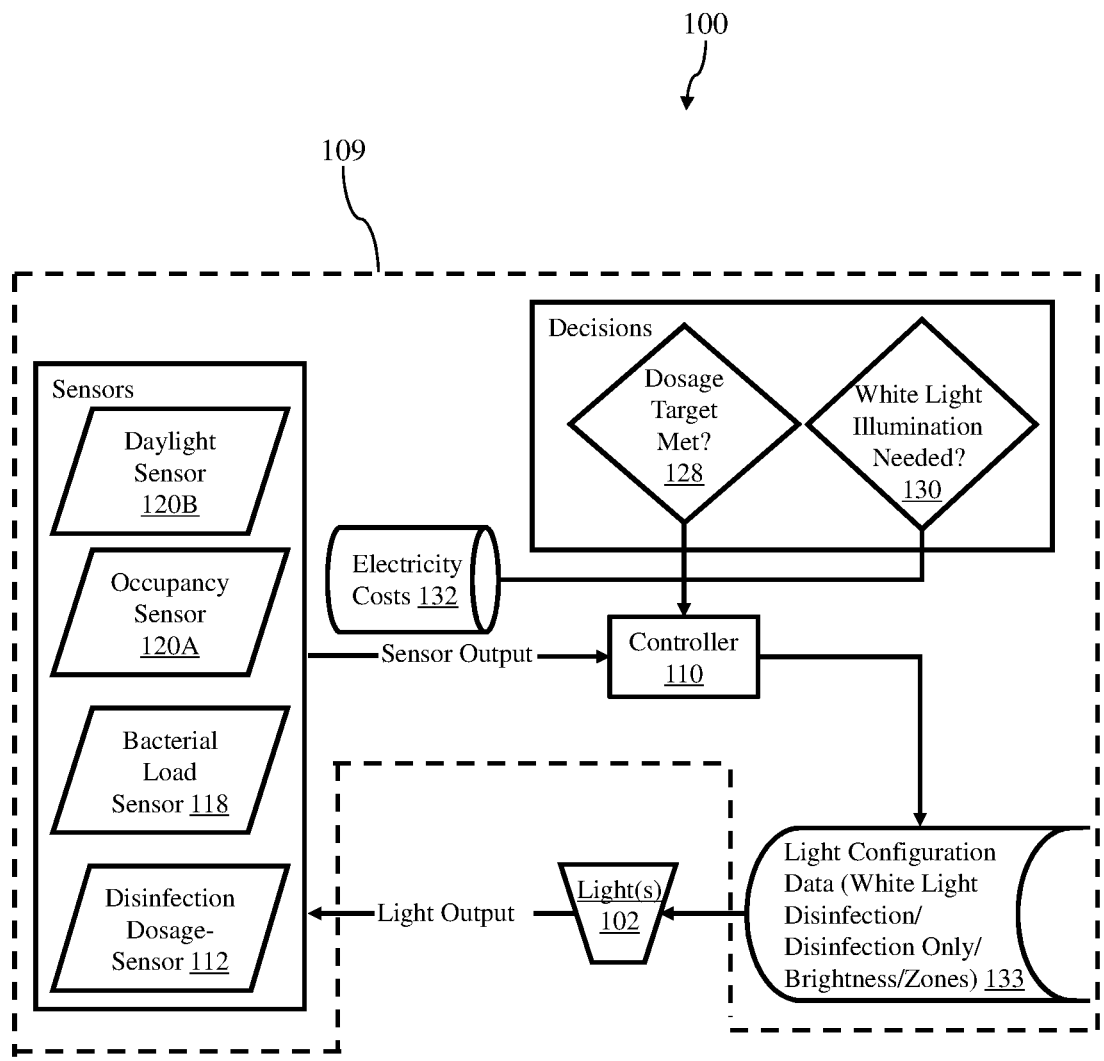
FIG. 6 shows a schematic view of a disinfecting light system including a control system, according to embodiments of the disclosure.

Additionally in other non-limiting examples, the controller of the control system for the disinfecting light system may receive and process a variety of data and/or information from various sources (e.g., sensors, storage devices, and the like) before regulating the disinfecting energy. That is, the controller may receive and process a variety of distinct data and/or information, from various sources, before adjusting the amount of disinfecting energy generated by the disinfecting light fixture. Turning to FIG. 6, a non-limiting schematic view of disinfecting light system 100 including control system 109 is shown. Specifically, FIG. 6 shows a schematic view of disinfecting light system 100 including control system 109, and a flow process of data and/or information through the various components of disinfecting light system 100 and/or control system 109. It is understood that similarly numbered and/or named components may function in a substantially similar fashion. Redundant explanation of these components has been omitted for clarity.

In the non-limiting example shown in FIG. 6, a plurality of sensors 112, 118, 120A, 120B of control system 109 may provide sensor output and/or data to controller 110 for aiding in the control of the operation of disinfecting light fixture 102 of disinfecting light system 100. In the non-limiting example, and as discussed herein with respect to FIG. 1, first sensor 112 may provide data and/or information relating to a measured amount of disinfecting energy 108 provided to a space, for example first space 30, to controller 110. Additionally, second sensor 118 may provide data and/or information relating to a sensed bacterial load of first space 30, third sensor 120A may provide data and/or information relating to a detected occupancy level of first space 30, and third sensor 120B may provide data and/or information relating to an amount of natural light 20 and/or amount of natural disinfecting energy 40 (see, FIG. 1) provided to first space 30.

Additionally, controller 110 may receive additional information and/or data from external sources and/or components, such as external storage devices, to aid in the control aiding in the control of the operation of disinfecting light fixture 102 of disinfecting light system 100. For example, and as shown in FIG. 6, a disinfecting energy target component 128 may provide data and/or information which aids controller 110 in determining if disinfecting energy 108 provided to first space 30 by first disinfecting light fixture 102 needs to be adjusted. That is, disinfecting energy target component 128 may provide data and/or information to determine if the amount of disinfecting energy 108 provided to first space 30, and measured by first sensor 112, is equal to or within the range of a predetermined or desired amount, level, minimum, and/or range of disinfecting energy 108 to be provided to first space 30, as discussed herein. In one non-limiting example, disinfecting energy target component 128 may include data or information relating to the predetermined disinfecting energy threshold, similarly discussed herein with respect to processes P1 and P2 of FIG. 2. Additionally in another non-limiting example, disinfecting energy target component 128 may include data or information relating to the preferred amount of disinfecting energy associated with detected environmental characteristics detected in first space 30 (e.g., occupancy level, amount of natural light, amount of natural disinfecting energy, task(s)), similarly discussed herein with respect to processes P6 and P7 of FIG. 2. Additionally, disinfecting energy target component 128 may also be configured to prompt controller 110 to determine if a dosage target for disinfecting energy 108 is met. That is, disinfecting energy target component 128 may also be configured to prompt controller 110 to determine if the amount of disinfecting energy 108 provided to first space 30, and measured by first sensor 112, is equal to or within the range of a predetermined or desired amount, level, minimum, and/or range of disinfecting energy 108 to be provided to first space 30.

Also shown in the non-limiting example of FIG. 6, an illuminating light target component 130 may provide data and/or information which aids controller 110 in determining if illuminating light 106 provided to first space 30 by first disinfecting light fixture 102 needs to be adjusted. In one non-limiting example, illuminating light target component 130 may include data or information relating to a predetermined illuminating light threshold, which may be based on the range of a predetermined or desired amount, level, minimum, and/or range of illuminating light 106 to be provided to first space 30. Additionally in another non-limiting example, illuminating light target component 130 may include data or information relating to the preferred amount of illuminating light associated with detected environmental characteristics detected in first space 30 (e.g., occupancy level, amount of natural light, natural disinfecting energy, task(s)), similarly discussed herein with respect to third sensors 120A, 120B, 120C of FIG. 1. As such, illuminating light target component 130 may provide data and/or information to controller 110 to determine if the amount of illuminating light 106 provided to first space is equal to or within the range of the predetermined amount or range of illuminating light 106, or alternatively the preferred amount of illuminating light, to be provided to first space as discussed herein. Additionally, illuminating light target component 130 may also be configured to prompt controller 110 to determine if white light illumination (e.g., illuminating light 106) is needed within first space 30. That is, illuminating light target component 130 may also be configured to prompt controller 110 to determine if the amount of illuminating light 106 provided to first space 30 is equal to or within the range of the predetermined amount or range of illuminating light, or preferred amount of illuminating light associated with detected environmental characteristics, to be provided to first space 30.

Illuminating light target component 130 may also be in communication with and/or may receive data from an additional source or component before providing data and/or prompting controller 110, as discussed herein. For example, and as shown in FIG. 6, an electrical cost storage device 132 may be operably coupled to and/or in communication with illuminating light target component 130. Electrical cost storage device 132 may include data and/or information relating to the cost of electricity for operating first disinfecting light fixture 102 of disinfecting light system 100 (e.g., peak hours, off-peak hours). As such, when prompting controller 110 to determine if white light illumination (e.g., illuminating light 106) is needed within first space 30, illuminating light target component 130 may also provide and/or consider information relating the cost of electricity for operating first disinfecting light fixture 102 provided by electrical cost storage device 132. Although shown as being operably coupled to and/or in communication with illuminating light target component 130, it is understood that electrical cost storage device 132 may also be operably coupled to and/or in communication with disinfecting energy target component 128. In this non-limiting example, when prompting controller 110 to determine if a dosage target for disinfecting energy 108 is met, disinfecting energy target component 128 may also provide and/or consider information relating the cost of electricity for operating first disinfecting light fixture 102 provided by electrical cost storage device 132.

Additionally in the non-limiting example shown in FIG. 6, after controller 110 determines that the amount of illuminating light 106 and/or disinfecting energy 108 provided to space 30 may require adjustment, controller 110 may provide input (e.g., a signal) to a light configuration data component 133, which may aid controller 110. That is, light configuration data component 133 may include data and/or information relating to the operation and/or function of first disinfecting light fixture 102 of disinfecting light system 100. As such, when controller 110 determines that the amount of illuminating light 106 and/or disinfecting energy 108 provided to space 30 requires adjustment, controller 110 may utilize light configuration data component 133, including data and/or information relating to the operation and/or function of first disinfecting light fixture 102, to control the operation of first disinfecting light fixture 102. Controller 110 may utilize light configuration data component 133 to ensure that the amount of illuminating light 106 and/or disinfecting energy 108 is adjusted, such that the amount of illuminating light 106 and/or disinfecting energy 108 is equal to or within the range of the desired (e.g., predetermined or preferred) amount of illuminating light 106 and/or disinfecting energy 108, as discussed herein.

Figure 7:
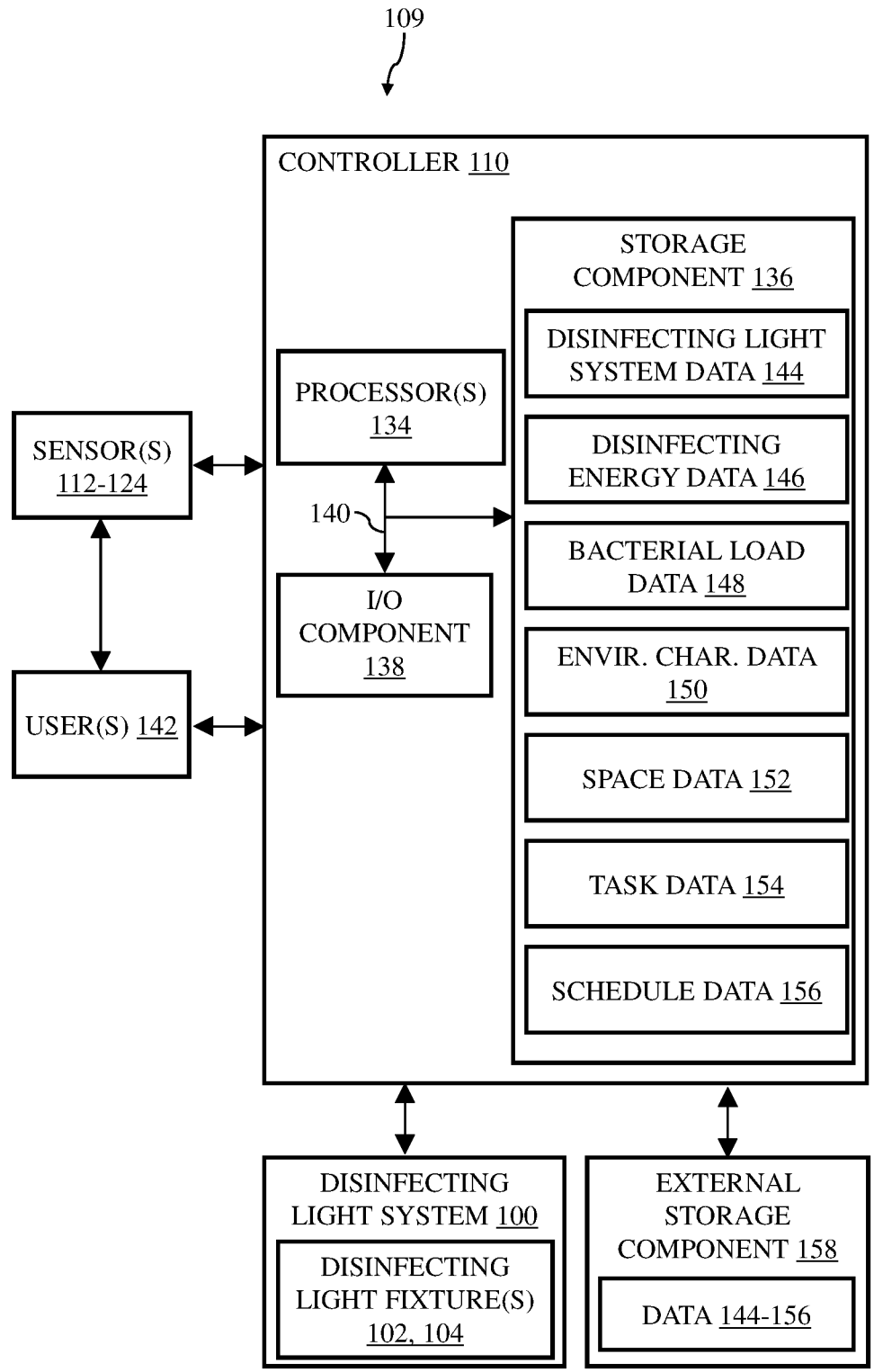
FIG. 7 shows a schematic view of a control system including a controller that regulates disinfecting energy generated by a disinfecting light system, according to embodiments of the disclosure.

FIG. 7 depicts a schematic view of control system 109, and the various components included within control system 109. In the non-limiting example shown in FIG. 7, control system 109 may include at least one controller 110 that may be configured to aid in regulating disinfecting energy 108 generated by disinfecting light system 100 within space(s) 30, 32 by performing the processes P1-P9 discussed herein with respect to FIGS. 2 and 3. Controller(s) 110 shown in FIG. 7 may be substantially similar to controller 110 discussed herein with respect to FIGS. 1 and/or 4. It is understood that similarly numbered and/or named components may function in a substantially similar fashion. Redundant explanation of these components has been omitted for clarity.

It is understood that controller(s) 110 may be implemented as a computer program product stored on a computer readable storage medium. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Python, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Control system 109 may include any type of controller(s) 110, which may include, for example, at least one processor 134, storage component 136, input/output (I/O) component(s) 138 (including users electronic devices discussed herein), and a communications pathway 140. In general, processor(s) 134 execute program code which is at least partially fixed in storage component 136. While executing program code, processor(s) 134 can process data, which can result in reading and/or writing transformed data from/to storage component 136 and/or I/O component(s) 138 for further processing. The pathway 140 provides a communications link between each of the components in controller(s) 110. I/O component 138 can comprise one or more human I/O devices, which enables user(s) 142 to interact with controller(s) 110. Controller(s) 110 may also be implemented in a distributed manner such that different components reside in different physical locations.

Storage component 136 may also include modules, data and/or electronic information relating to various other aspects of control system 109. Specifically, operational modules, information, and/or data relating to disinfecting light system data 144, disinfecting energy data 146, bacterial load data 148, environmental characteristic data 150, space data 152, task data 154, and schedule data 156. The operational modules and/or data may include the required information and/or may allow control system 109, and specifically controller 110, to perform the processes discussed herein for regulating disinfecting energy 108 generated by disinfecting light system 100 within space(s) 30, 32. Additionally, sensors 112, 118, 120A, 120B, 120C, 122, 124 may in communication with control system 109, and more specifically controller 110 of control system 109, to transmit measured, sensed, and/or detected data (e.g., sensed bacterial load, measure amount of disinfecting light in space(s) 30, 32, and the like) to controller 110. Furthermore, controller 110 may utilize the transmitted data from sensors 112, 118, 120A, 120B, 120C, 122, 124, and the operational modules, information, and/or data stored on storage component 136 (e.g., disinfecting light system data 144, disinfecting energy data 146, bacterial load data 148, and so on) to regulate disinfecting energy 108 generated by disinfecting light system 100 within space(s) 30, 32, as discussed herein.

Control system 109, and specifically controller 110 of control system 109, may also be in communication with an external storage component 158. External storage component 158 may be configured to store various modules, data and/or electronic information relating to various other aspects of control system 109, similar to storage component 136 of controller(s) 110. Additionally, external storage component 158 may be configured to share (e.g., send and receive) data and/or electronic information with controller(s) 110 of control system 109. In the non-limiting example shown in FIG. 7, external storage component 158 may include any or all of the operational modules and/or data shown to be stored on storage component 136 (e.g., data 144-156). In a non-limiting example, external storage component 158 may be a cloud-based storage component or system.

Furthermore, it is understood that controller(s) 110 of control system 109 or relevant components thereof (such as an API component, agents, etc.) may also be automatically or semi-automatically deployed into a computer system by sending the components to a central server or a group of central servers. The components are then downloaded into a target computer that will execute the components. The components are then either detached to a directory or loaded into a directory that executes a program that detaches the components into a directory. Another alternative is to send the components directly to a directory on a client computer hard drive. When there are proxy servers, the process will select the proxy server code, determine on which computers to place the proxy servers' code, transmit the proxy server code, and then install the proxy server code on the proxy computer. The components will be transmitted to the proxy server and then it will be stored on the proxy server.

Figure 8:
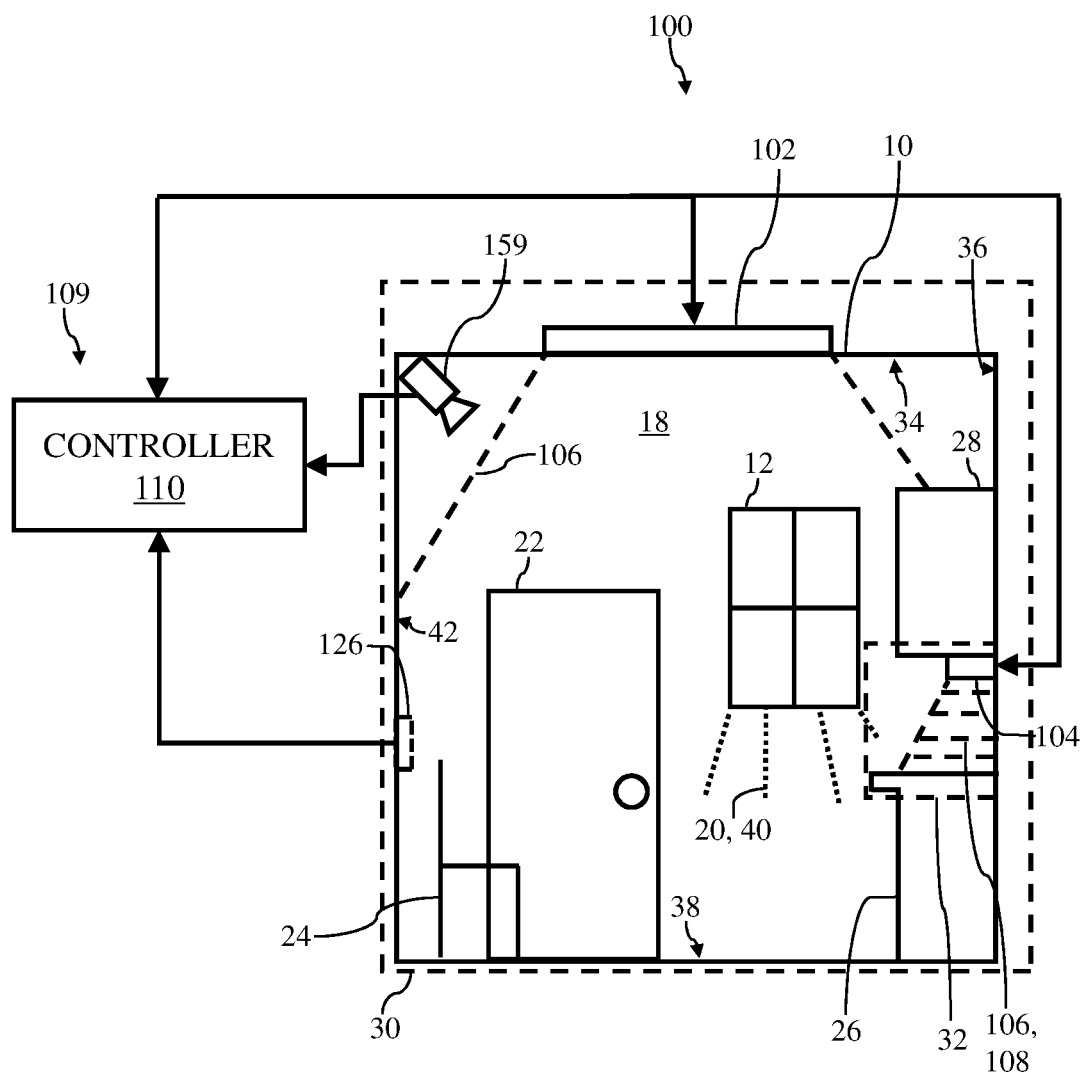
FIG. 8 shows a schematic view of an illustrative environment including a disinfecting light system and a control system, according to additional embodiments of the disclosure.

FIG. 8 shows another non-limiting example of environment 10 including disinfecting light system 100. As shown in the non-limiting example of FIG. 8, environment 10 may include multiple spaces 30, 32, and disinfecting light system 100 may include control system 109, as similarly discussed herein with respect to FIG. 1. Control system 109, and more specifically controller 110, may be configured to regulate the operation of disinfecting light fixtures 102, 104, as discussed herein. It is understood that similarly numbered and/or named components may function in a substantially similar fashion. Redundant explanation of these components has been omitted for clarity.

However, distinct from the non-limiting example discussed herein with respect to FIG. 1, control system 109 shown in FIG. 8 may not include a single sensor (e.g., sensors 112, 118, 120A, 120B, 120C). That is, control system 109 of disinfecting light system 100 shown in FIG. 8 may include controller 110, but may not include a sensor(s) positioned within environment 10 and/or spaces(s) 30, 32. Rather in this non-limiting example, data, information, and/or characteristics relating to environment 10 may be detected and/or determined by other components of environment 10 and subsequently provided to controller 110 for regulating the operation of disinfecting light fixtures 102, 104. For example, disinfecting light fixtures 102, 104 of disinfecting light system 100 may be configured to provide data and/or information relating to an amount of illuminating light 106 and/or disinfecting energy 108 to controller 110 in place of first sensor 112 and/or third sensor 120A. That is, in place of sensors 112, 120A, disinfecting light fixtures 102, 104, in communication with controller 110 of control system 109, may be configured to determined and/or detect an amount of illuminating light 106 and/or disinfecting energy 108 being provided within environment 10 by disinfecting light fixtures 102, 104, and may transmits that information to controller 110 to aid in regulating the operation of disinfecting light fixtures 102, 104, as discussed herein. In this non-limiting example, controller 110 may adjust illuminating light 106 and/or disinfecting energy 108 provided to first spaces 30, 32 based on, at least in part, the data and/or information provided to controller 110 directly from first disinfecting light fixtures 102, 104.

Additionally as shown in the non-limiting example of FIG. 8, environment 10 may also include a camera 159 positioned therein. For example, camera 159 may be positioned on, and/or adjacent to ceiling 34 of environment 10. In a non-limiting example shown in FIG. 8, camera 159 may be operably coupled to and/or in communication with controller 110 of control system 109 for disinfecting light system 100, and may provide visual data and/or information (e.g., real-time video data) for environment 10, and more specifically spaces 30, 32 of environment 10. In another non-limiting example, camera 159 may be part of a video surveillance system for environment 10, and may be configured to provide visual data and/or information (e.g., real-time video recording) for environment 10, and more specifically spaces 32 of environment 10 to the video surveillance system, which in turn may provide the data to controller 110. For example, camera 159 (and video surveillance system) may obtain data relating to environmental characteristic(s) of environment 10 and/or space 30, 32. Specifically, camera 159 may be utilized to obtain data and/or information relating to an occupancy level of spaces 30, 32 and/or task(s) being performed within space(s) 30, 32, and may provide the data and/or information to controller 110 to aid in the regulation of disinfecting light fixtures 102, 104 of disinfecting light system 100, as discussed herein. In this non-limiting example, camera 159 (and video surveillance system) may replace sensors 120B, 120C previously included in the non-limiting example discussed herein with respect to FIG. 1.

Furthermore, and as shown in the non-limiting example of FIG. 8, environment 10, and more specifically first space 30, may or may not include access control component 126. That is, access control component 126 is shown in phantom as optional. Access control component 126 may aid controller 110 in the regulation of disinfecting light fixtures 102, 104 of disinfecting light system 100 by providing operational schedule information and/or allowing a user of environment 10 to manually input information for regulating and/or adjusting the operation of disinfecting light fixtures 102, 104.

Figure 9:
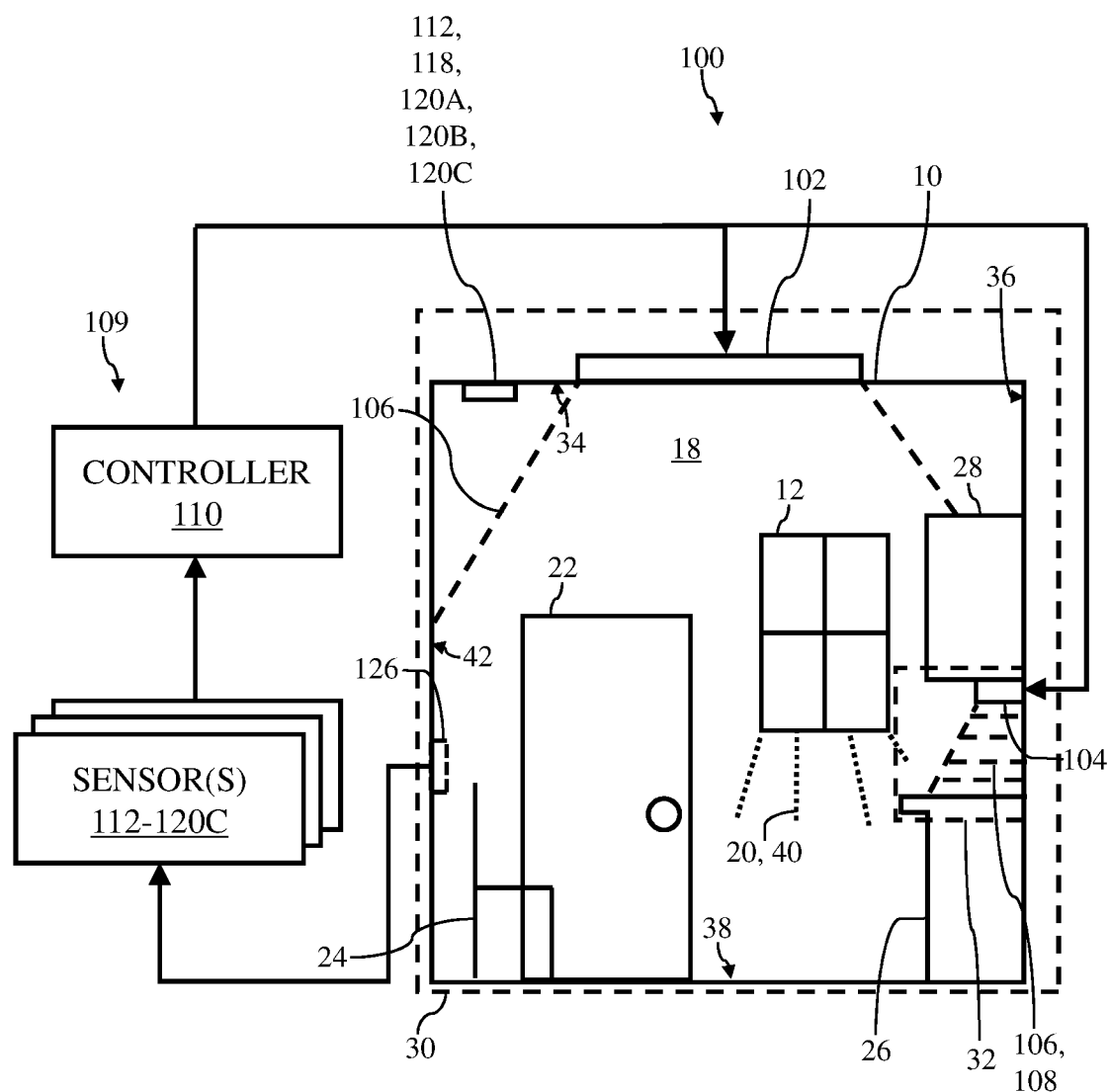
FIG. 9 shows a schematic view of an illustrative environment including a disinfecting light system, a control system and a single sensor, according to embodiments of the disclosure.

FIG. 9 shows an additional non-limiting example of environment 10 including and/or illuminated by disinfecting light system 100. As shown in the non-limiting example of FIG. 9, environment 10 may include multiple spaces 30, 32, and disinfecting light system 100 may include control system 109, as similarly discussed herein with respect to FIG. 1. However distinct from the non-limiting example discussed herein with respect to FIG. 1, control system 109 shown in FIG. 9 may only include a single sensor 112, 118, 120A, 120B, 120C. That is, control system 109 may include a single sensor 112, 118, 120A, 120B, 120C configured to obtain data, information, and/or characteristics relating to environment 10 (e.g., disinfecting energy, bacterial load, environmental characteristics, and so on), and subsequently provide the data, information, and/or characteristics to controller 110 for regulating the operation of disinfecting light fixtures 102, 104. In the non-limiting example shown in FIG. 9, the single sensor 112, 118, 120A, 120B, 120C of control system 109 for disinfecting light system 100 may be positioned on, and/or coupled to ceiling 34. The data, information, and/or characteristics obtained by the single sensor 112, 118, 120A, 120B, 120C of control system 109 may be dependent on the type or configuration of sensor 112, 118, 120A, 120B, 120C included within environment 10. For example, when the single sensor of control system 109 is configured or formed as first sensor 112, the single sensor of control system 109 may measure an amount of disinfecting energy provided to environment 10, and more specifically spaces 30, 32, as previously discussed herein. The single sensor 112, 118, 120A, 120B, 120C of control system 109 may aid controller 110 in regulating the operation of disinfecting light fixtures 102, 104 as similarly discussed with respect to FIGS. 1-5. Redundant explanation of the regulating processes has been omitted for brevity.

Figure 10:
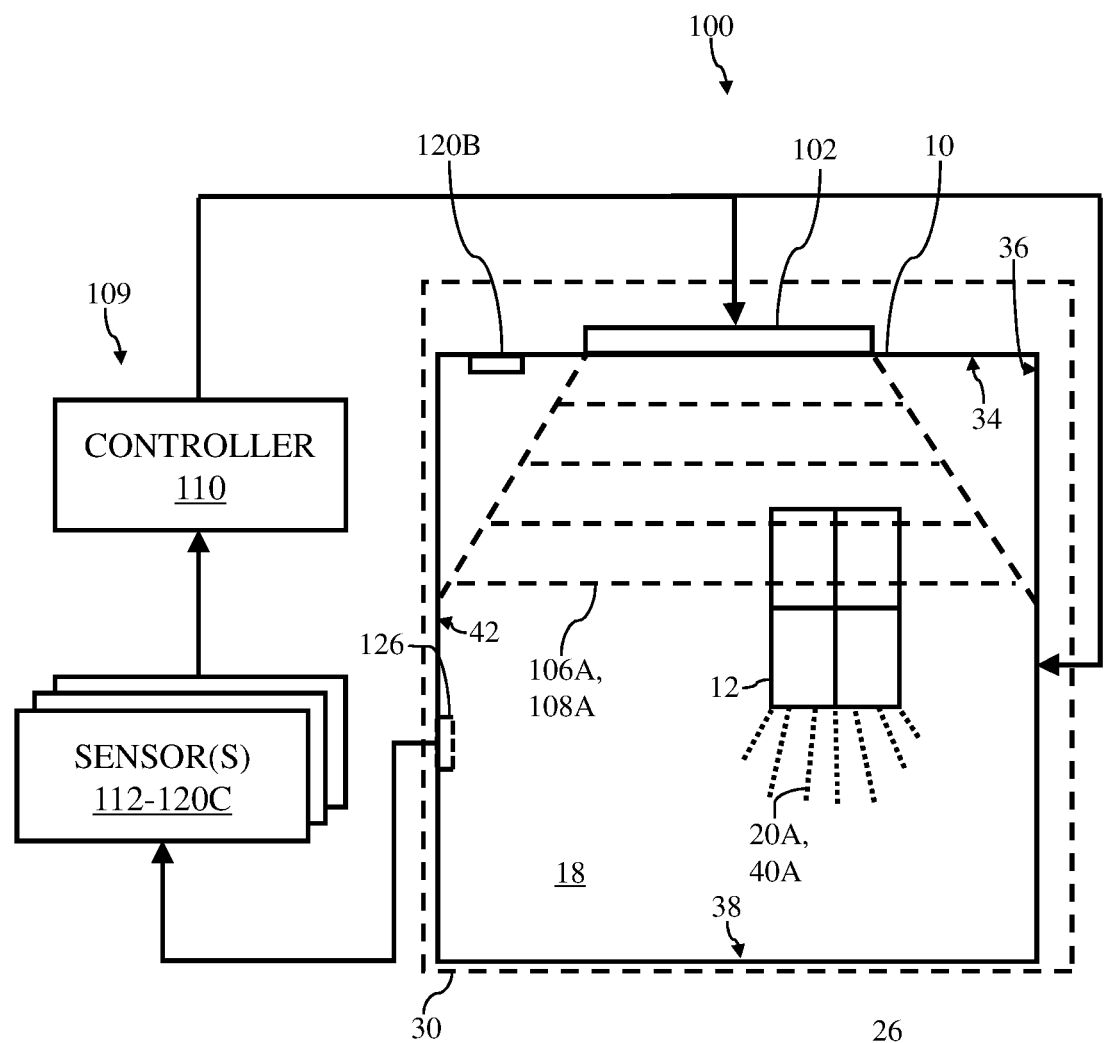
FIGS. 10 and 11 show schematic views of an illustrative environment including a disinfecting light system providing distinct amounts of disinfecting energy and/or illuminating light, according to embodiments of the disclosure.
Figure 11:
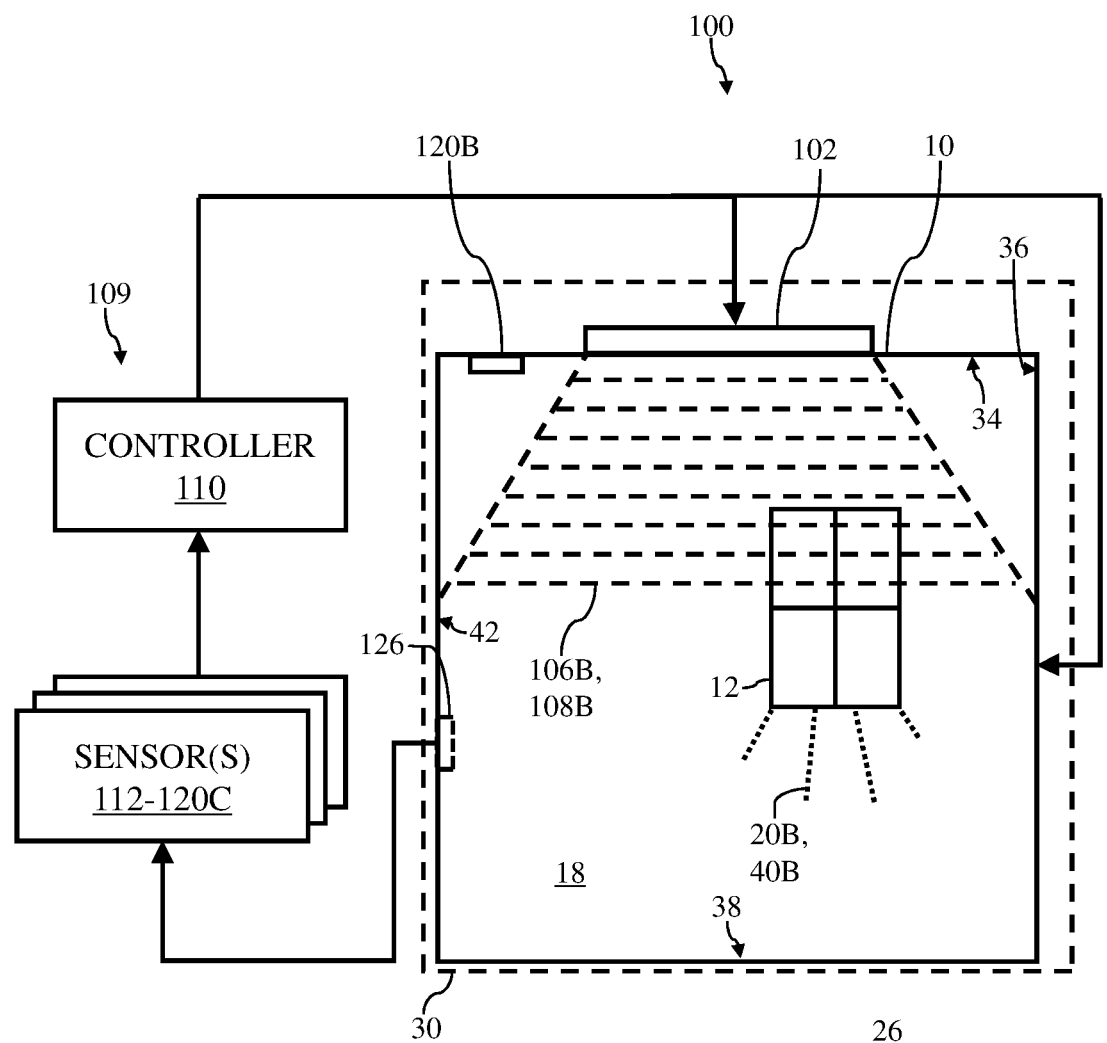

FIGS. 10 and 11 show additional non-limiting examples of environment 10 including and/or illuminated by disinfecting light system 100. Environment 10 including and/or illuminated by disinfecting light system 100, as shown in FIGS. 10 and 11, may show substantially the same space 30/environment 10 under distinct conditions (e.g., amount of natural light 20, natural disinfecting energy 40, disinfecting energy 108), as discussed herein. In the non-limiting example, environment 10 of FIGS. 10 and 11 may only include a single space (e.g., first space 30), a single disinfecting light fixture 102, and may have items removed (e.g., door 22, chair 24, workstation 26, and so on). These items are removed from environment 10 and/or first space 30 for the sake of clarity of the figures. However, it is understood that these items may be included within environment 10 as previously discussed herein.

Controller 110 may regulate and/or adjust the operation of disinfecting light fixture 102 based on data relating to environment 10 and/or first space 30. That is, controller 110 may regulate and/or adjust the operation of disinfecting light fixture 102 (e.g., emitted illuminating light 106 and/or disinfecting energy 108) based on obtained data, information, and/or characteristics relating to environment 10 (e.g., disinfecting energy, bacterial load, environmental characteristics, and so on). For example, and as shown in FIGS. 10 and 11, controller 110 may regulate and/or adjust the operation of disinfecting light fixture 102 based on obtained, sensed, measured, and/or determined data relating to natural light 20A, 20B and/or natural disinfecting energy 40A, 40B provided to first space 30 via window 12. As shown in FIGS. 10 and 11, and similarly discussed herein with respect to FIG. 1, the single sensor of control system 109 may be formed as third sensor 120B, which may be configured to detect, determine, and/or measure an amount of natural light 20A, 20B, and natural disinfecting energy 40A, 40B. In additional non-limiting examples, single sensor 120B of control system 109 may be configured to detect, determine, and/or measure an amount of disinfecting energy 108 emitted by disinfecting light fixture 102, or alternatively, disinfecting light fixture 102 itself may be configured to provide the amount of disinfecting energy 108 to controller 110.

As shown in the non-limiting examples of FIGS. 10 and 11, the intensity for natural light 20A, and natural disinfecting energy 40A, 40B may vary. That is, a first intensity of natural light 20A and a first intensity of natural disinfecting energy 40A, as shown in FIG. 10, may vary and/or be distinct from a second intensity of natural light 20B and a second intensity of natural disinfecting energy 40B shown in FIG. 11. In the non-limiting example shown in FIGS. 10 and 11, the first intensity for natural light 20A may be greater than the second intensity for natural light 20B, and the first intensity for natural disinfecting energy 40A may be greater than the second intensity for natural disinfecting energy 40B. The change in intensity in the natural light 20A, 20B and natural disinfecting energy 40A, 40B may be a result of, for example, a change in the time of day (e.g., 12:00 PM (FIG. 10) to 5:00 PM (FIG. 11)), a change in weather (e.g., cloud coverage), or the (partial) covering of the window with a blind (not shown).

As a result of the change in intensity of natural light 20A, 20B and natural disinfecting energy 40B in first space 30 of environment 10, controller 110 may regulate and/or adjust the operation of disinfecting light fixture 102. That is, and as discussed herein with respect to FIGS. 1-5, because of the change in intensity of natural light 20A, 20B and natural disinfecting energy 40A, 40B in first space 30 controller 110 may adjust the operational dosage intensity of illuminating light 106A, 106B and disinfecting energy 108A, 108B provided to first space by disinfecting light fixture 102. In the non-limiting examples shown in FIGS. 10 and 11, disinfecting light fixture 102 may emit illuminating light 106A, 106B and disinfecting energy 108A, 108B at two different operational dosage intensities. Specifically in FIG. 10, disinfecting light fixture 102 of disinfecting light system 100 may emit illuminating light 106A at a first operational dosage intensity for illuminating light, and may emit disinfecting energy 108A at a first operational dosage intensity for disinfecting energy. Conversely as shown in FIG. 11, and with comparison to FIG. 10, disinfecting light fixture 102 of disinfecting light system 100 may emit illuminating light 106B at a second operational dosage intensity for illuminating light, and may emit disinfecting energy 108B at a second operational dosage intensity for disinfecting energy. The first operational dosage intensity for illuminating light (e.g., illuminating light 106A) may be distinct from the second operational dosage intensity for illuminating light (e.g., illuminating light 106B). Similarly, the first operational dosage intensity for disinfecting energy (e.g., disinfecting energy 108A) may be distinct from the second operational dosage intensity for disinfecting energy (e.g., disinfecting energy 108B).

In the non-limiting example shown in FIGS. 10 and 11, the first operational dosage intensity for illuminating light (e.g., illuminating light 106A) may be less than the second operational dosage intensity for illuminating light (e.g., illuminating light 106B), and the first operational dosage intensity for disinfecting energy (e.g., disinfecting energy 108A) may be less than the second operational dosage intensity for disinfecting energy (e.g., disinfecting energy 108B). The difference in operational dosage intensities for illuminating light 106A, 106B and disinfecting energy 108A, 108B may be dependent on the change in intensity of natural light 20B and natural disinfecting energy 40A, 40B, as discussed herein. For example, when the intensity of natural light 20A, 20B and natural disinfecting energy 40A, 40B decreases, the operational dosage intensity for illuminating light 106A, 106B, and the operational dosage intensity for disinfecting energy 108A, 108B may increase. Specifically, when controller 110 determines that the intensity of natural light 20A, 20B and natural disinfecting energy 40A, decreases, based on data or information determined by sensor 120B, controller 110 may increase the operational dosage intensity for illuminating light 106A, 106B, and disinfecting energy 108A, 108B, respectively, by regulating and/or adjusting the operation of disinfecting light fixture 102.

Figure 12:
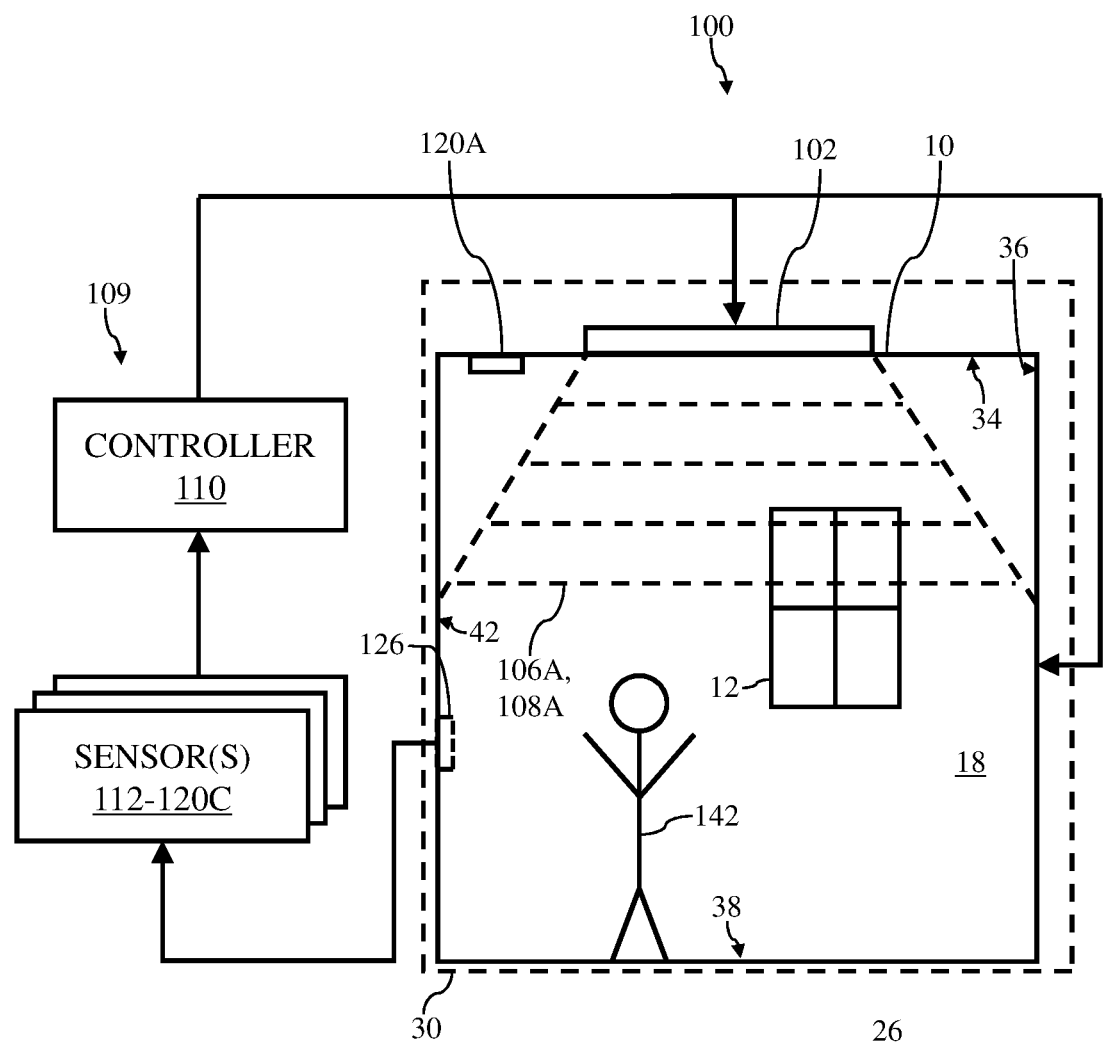
FIGS. 12 and 13 show schematic views of an illustrative environment including a disinfecting light system providing distinct amounts of disinfecting energy and/or illuminating light, according to additional embodiments of the disclosure.
Figure 13:
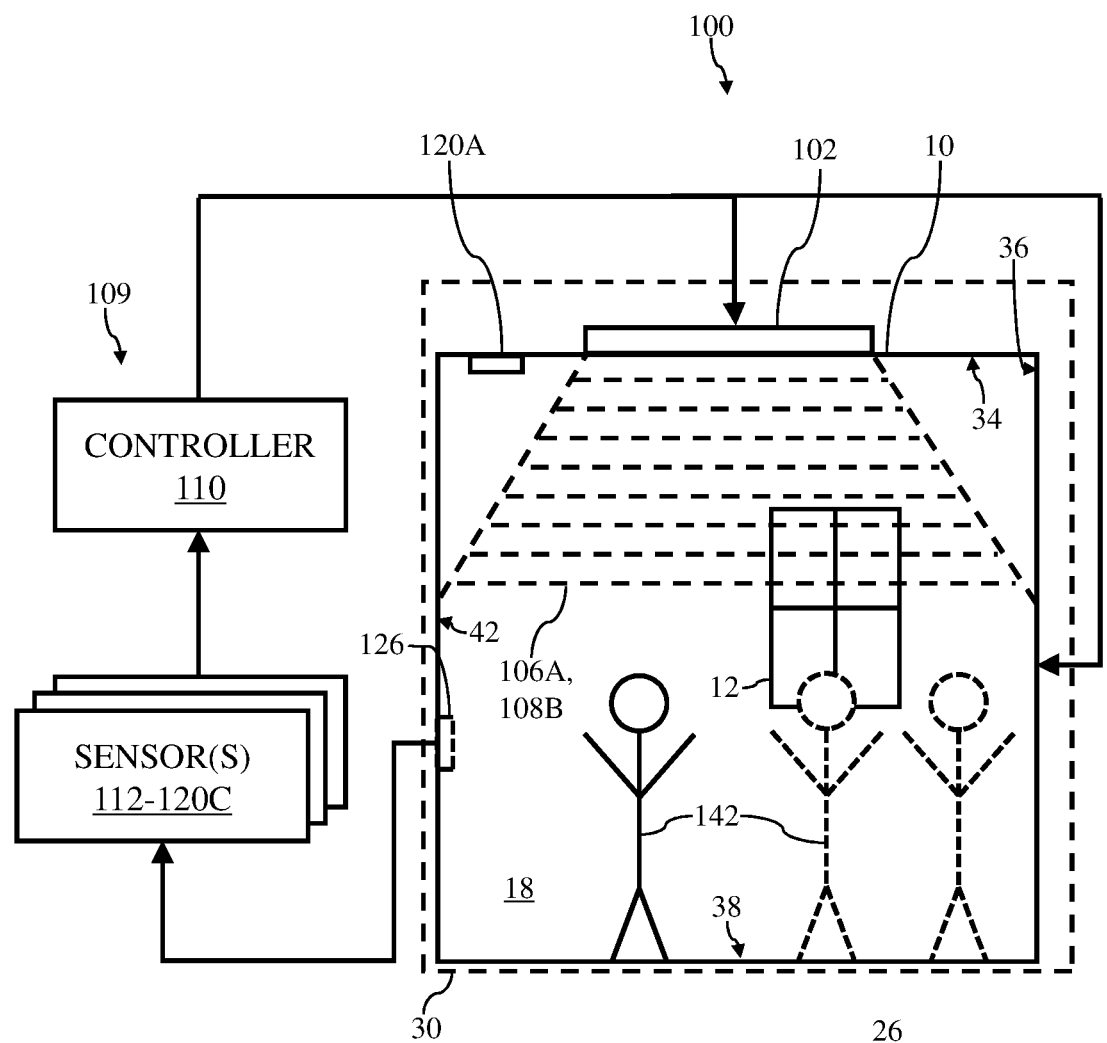

FIGS. 12 and 13 show further non-limiting examples of environment 10 including disinfecting light system 100. Similar to the non-limiting examples shown in FIGS. 12 and 13, environment 10 shown in FIGS. 12 and 13 may show substantially the same space 10 under distinct conditions (e.g., amount of natural light 20, natural disinfecting energy 40, disinfecting energy 108), as discussed herein. Additionally, the non-limiting examples shown in FIGS. 12 and 12 may include substantially similar features and/or components as the non-limiting examples shown in FIGS. 10 and 11. It is understood that similarly numbered and/or named components may function in a substantially similar fashion. Redundant explanation of these components has been omitted for clarity.

In the non-limiting examples shown in FIGS. 12 and 13, controller 110 may regulate and/or adjust the operation of disinfecting light fixture 102 based on obtained, sensed, measured, and/or determined data relating to an occupancy level of first space 30. Additionally in the non-limiting example shown in FIGS. 12 and 13, and similarly discussed herein with respect to FIG. 1, the single sensor of control system 109 may be formed as third sensor 120A, which may be configured to detect, determine, and/or measure an occupancy level of first space 30, and provide the data relating to the occupancy level of first space 30 to controller 110. When comparing FIGS. 12 and 13, occupancy level of first space 30 may change. That is, third sensor 120A may determine that the occupancy level for first space 30 initially includes one user 142, as shown in FIG. 12, and may subsequently determine that the occupancy level for first space 30 includes a plurality of users 142 at a later time, as shown in FIG. 13. In addition to receiving data or information relating to the change in the occupancy level of first space controller 110 may also be provided with a preferred amount of disinfecting energy associated with each of the detected occupancy levels of first space 30 (e.g., single user 142 in FIG. 12, plurality of users 142 in FIG. 13).

As a result of the change in the occupancy level of first space 30 of environment 10, controller 110 may regulate and/or adjust the operation of disinfecting light fixture 102. That is, and as discussed herein with respect to FIGS. 1-5, because of the change in occupancy level for first space 30, controller 110 may adjust the operational dosage intensity of illuminating light 106A, 106B and/or disinfecting energy 108A, 108B provided to first space 30 by disinfecting light fixture 102. In the non-limiting examples shown in FIGS. 12 and 13, and distinct from the non-limiting example discussed herein with respect to FIGS. 10 and 11, disinfecting light fixture 102 may emit illuminating light 106A at a single operational dosage intensity. That is, regardless of the detected change in occupancy level for first space 30, as detected by third sensor 120A, controller 110 may not adjust the operation of disinfecting light fixture 102, and disinfecting light fixture 102 may emit illuminating light 106A at a constant operational dosage intensity.

However as shown in the non-limiting examples of FIGS. 12 and 13, and similar to FIGS. 10 and 11, disinfecting light fixture 102 may emit disinfecting energy 108A, 108B at two different operational dosage intensities. Specifically in FIG. 12, disinfecting light fixture 102 of disinfecting light system 100 may emit disinfecting energy 108A at a first operational dosage intensity for disinfecting energy. Conversely as shown in FIG. 13, and with comparison to FIG. 12, disinfecting light fixture 102 of disinfecting light system 100 may emit disinfecting energy 108B at a second operational dosage intensity for disinfecting energy. The first operational dosage intensity for disinfecting energy (e.g., disinfecting energy 108A) may be distinct from the second operational dosage intensity for disinfecting energy (e.g., disinfecting energy 108B). For example, the first operational dosage intensity for disinfecting energy (e.g., disinfecting energy 108A) may be less than the second operational dosage intensity for disinfecting energy (e.g., disinfecting energy 108B). The difference in operational dosage intensities for disinfecting energy 108A, 108B may be dependent on the change in occupancy level for first space 30, as discussed herein. For example, when the number of users 142 located within first space 30 increases (e.g., change in occupancy levels), the operational dosage intensity for disinfecting energy 108A, 108B may also increase. Specifically, when controller 110 determines that the number of users 142 located within first space 30 increases, based on the occupancy level detected by sensor 120A, controller 110 may increase the operational dosage intensity for disinfecting energy 108A, 108B, by regulating and/or adjusting the operation of disinfecting light fixture 102. In this non-limiting example, the operational dosage for disinfecting energy 108A, 108B may be adjusted, changed, and/or varied (e.g., increased) independent of the operation and/or operational dosage of illuminating light 106A provided to first space 30.

Figure 14:
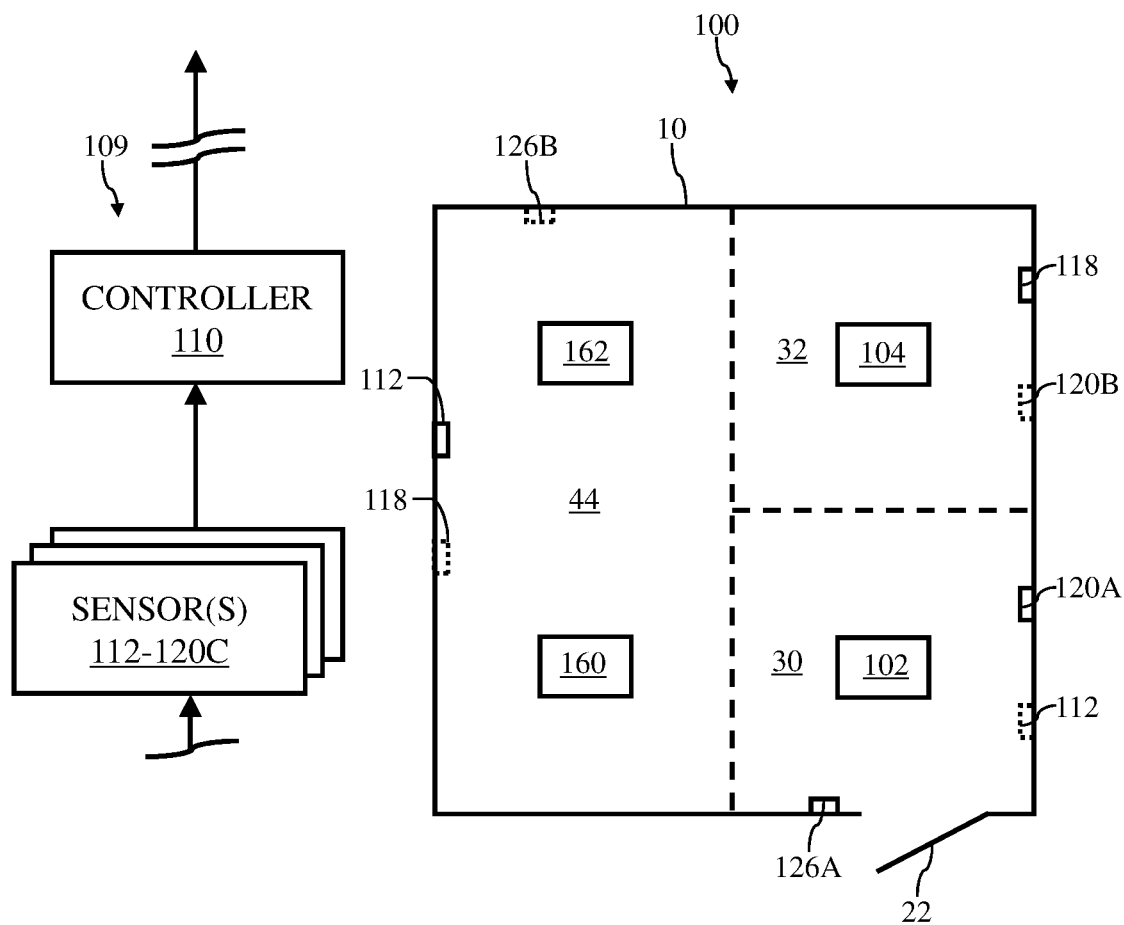
FIG. 14 shows a schematic view of an illustrative environment made up of a plurality of spaces in a single room of the environment, according to embodiments of the disclosure. The environment also includes a light system, a control system and a plurality of sensors.
Figure 15:
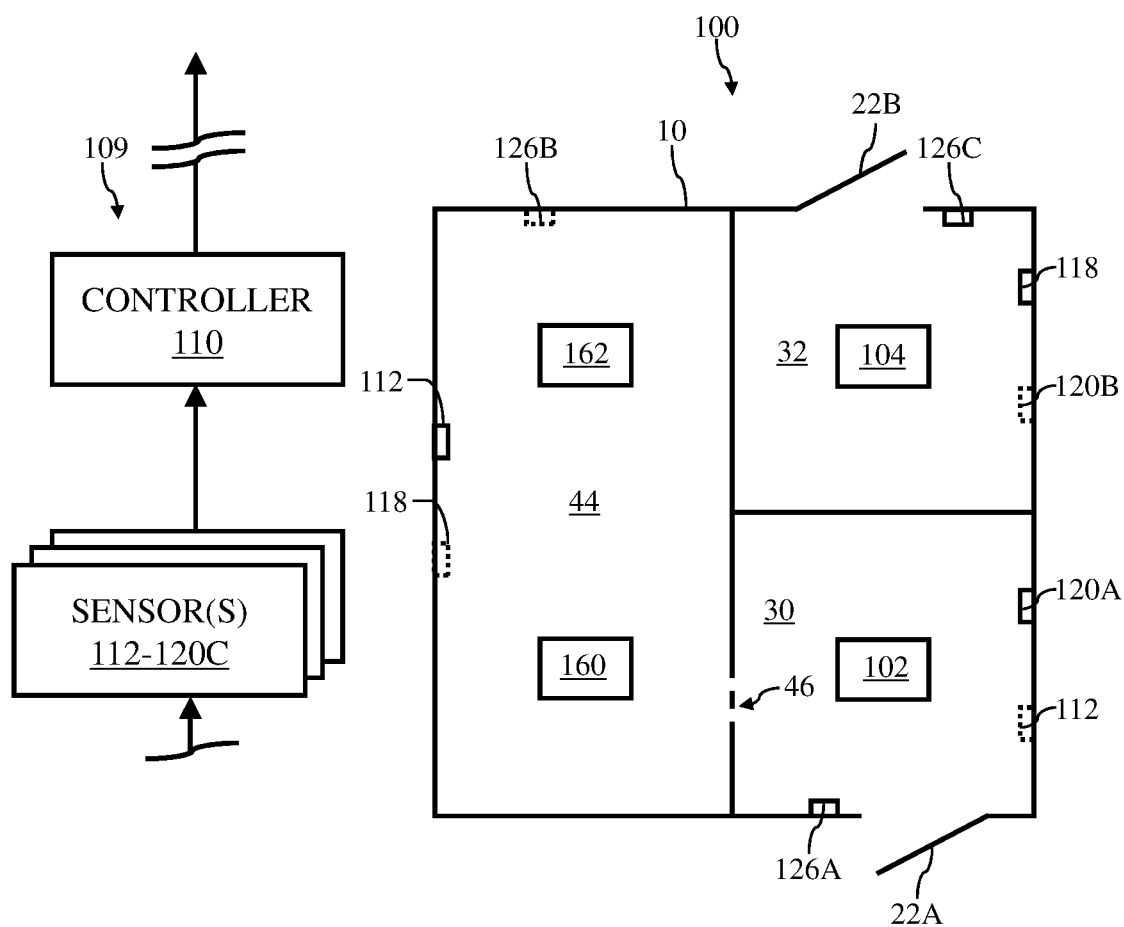
FIG. 15 shows a schematic view of an illustrative environment made up of a plurality of spaces in two distinct rooms of the environment, according to embodiments of the disclosure. The environment also includes a light system, a control system and a plurality of sensors.

FIGS. 14 and 15 show additional, non-limiting examples of environment 10 including a plurality of spaces defined therein. Specifically in the non-limiting examples of FIGS. 14 and 15, environment 10 may include three distinct spaces 30, 32, 44. Each space 30, 32, 44 may include and/or may be defined by disinfecting light fixture(s) 102, 104, 160, 162 of disinfecting light system 100. For example, first space 30 may include, be defined by, and/or may be provided with illuminating light 106 and/or disinfecting energy 108 from first disinfecting light fixture 102. Additionally, second space 32 may include, be defined by, and/or may be provided with illuminating light 106 and/or disinfecting energy 108 from second disinfecting light fixture 104. Furthermore, third space 44 may include, be defined by, and/or may be provided with illuminating light 106 and/or disinfecting energy 108 from third disinfecting light fixture 160 and fourth disinfecting light fixture 162, respectively. Additionally as shown in the non-limiting examples of FIGS. 14 and 15, each of the distinct spaces 30, 32, 44 may include at least one sensor 112, 118, 120A, 120B, 120C (not all shown) of control system 109 for disinfecting light system 100. Each of the distinct spaces 30, 32, 44 may be provided illuminating light 106 and/or disinfecting energy 108 from the corresponding disinfecting light fixture 102, 104, 160, 162, and controller 110 of control system 109 may regulate and/or adjust the operation of each disinfecting light fixture 102, 104, 160, 162.

In FIG. 14, environment 10 may include a single room, similar to the example discussed herein with respect to FIG. 1. As such, each space 30, 32, 44 may be a portion of the single room forming environment 10. In the example shown in FIG. 14, environment 10 may also include at least one access control component 126A, 126B. Specifically, environment 10 may include access control component 126A positioned within first space 30, adjacent door 22. In one example, access control component 126A may be configured to aid controller 110 in regulating and/or adjusting the operation of each disinfecting light fixture 102, 104, 160, 162 included within spaces 30, 32, 44 of environment 10. Additionally, environment 10 may include a second access control component 126B. For example, a second, distinct access control component 126B (shown in phantom) may be positioned within third space 44. In one example, environment 10 may include a second, distinct access control component 126B in third space 44 because of its size and/or the increased number of disinfecting light fixtures (e.g., third disinfecting light fixture 160, fourth disinfecting light fixture 162) that may provide illuminating light 106 and/or disinfecting energy 108 to third space 44. In this example, access control component 126A may be configured to aid controller 110 in regulating and/or adjusting the operation of each disinfecting light fixture 102, 104 included within spaces 30, 32, and second access control component 126B may be configured to aid controller 110 in regulating and/or adjusting the operation of each disinfecting light fixture 160, 162 included within space 44.

Distinct from the example shown in FIG. 14, environment 10 shown in FIG. 15 may include a plurality of distinct rooms. That is, and as shown in FIG. 15, second space 32 may be completely separate from first space 30 and third space 44, respectively. Additionally, third space 44 may be substantially separated from first space 30 by the walls dividing first space 30, second space 32, and third space 44, respectively. However, third space 44 may be accessible from first space 30 via an opening and/or breezeway 46. Because of the separation and/or divide between the spaces 30, 32, 44 of environment 10 (e.g., distinct rooms), environment 10 may include a plurality of access control component 126A, 126B, 126C. That is, a first access control component 126A may be positioned within first space 30, adjacent door 22A, and a second access control component 126B (shown in phantom) may be positioned within third space 44. Additionally, and because second space 32 is completely separate from and/or inaccessible from first space 30 and/or third space 44, a third access control component 126C may be positioned within second space 32, adjacent door 22B.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

We claim:

1. A disinfecting LED lighting system comprising:
at least one light fixture disposed in a ceiling in an environment and configured to output a first light and a second light, wherein the first light and the second light are emitted from independent sources and operate independently; and wherein:
the first light and the second light both emit a portion of a spectral range as a disinfecting energy within a disinfecting wavelength range of 380 to 420 nanometers,
the first light emits a first output wherein at least 20% of the spectral range is within the disinfecting wavelength range; and
the second light emits a second output wherein at least 70% of the spectral range is within the disinfecting wavelength range; and
at least one sensor in communication with the at least one light fixture and configured to detect a characteristic of the environment, wherein the characteristic of the environment is an amount of disinfecting energy, and wherein the at least one sensor is configured to detect an amount of natural light disinfecting energy and detect an amount of disinfecting energy of the first light and the second light within the disinfecting wavelength range of 380 to 420 nanometers; and
a controller in communication with the at least one sensor and the at least one light fixture and configured to cause an event.

2. The disinfecting LED lighting system of claim 1, wherein the event comprises:
using the characteristic of the environment detected by the sensor to determine if the first light or the second light will be operated; and
operating only the first light or only the second light.

3. The disinfecting LED lighting system of claim 1, wherein the event comprises:
detecting the first output of the first light or the second output of the second light, the output correlating to an amount of disinfecting energy;
comparing the disinfecting energy of the first output of the first light or the disinfecting energy of the second output of the second light to a required target dosage of disinfecting energy; and
adjusting the output of the first light or the output of the second light to meet the required target dosage of disinfecting energy.

4. The disinfecting LED lighting system of claim 3, wherein the controller is further configured to adjust the output of the first light or the output of the second light without varying an output ratio of disinfecting energy.

5. The disinfecting LED lighting system of claim 1, wherein the characteristic of the environment is an occupancy of the environment, and wherein the controller is configured to operate the first light when the occupancy is detected in the environment; and wherein the controller is configured to operate the second light when the occupancy is not detected in the environment.

6. The disinfecting LED lighting system of claim 5, wherein at least one sensor is configured to detect a number of users that occupy the environment.

7. The disinfecting LED lighting system of claim 1, further comprising a plurality of light fixtures disposed within the environment and in communication with each other.

8. The disinfecting LED lighting system of claim 7, wherein the controller is in communication with a computing system configured to control operation of the plurality of light fixtures and other operations of the environment.

9. The disinfecting LED lighting system of claim 1, wherein the first light comprises an illuminating white light.

10. The disinfecting LED lighting system of claim 1, wherein the controller is configured to control the output of the first light and the output of the second light based on a predetermined schedule.

11. The disinfecting LED lighting system of claim 1, wherein the controller is in wireless communication with the at least one light fixture and the at least one sensor.

12. The disinfecting LED lighting system of claim 1, comprising a second sensor in communication with the at least one light fixture and configured to detect a second characteristic of the environment, wherein the second characteristic is an amount of disinfecting energy provided to the environment.

13. The disinfecting LED lighting system of claim 1, further comprising an access control component in communication with the controller and the at least one light fixture, wherein the access control component is configured to control the first light and the second light of the at least one light fixture.

14. The disinfecting LED lighting system of claim 1, wherein the controller is configured to maintain an average amount of disinfecting energy provided to the environment or a dosage of disinfecting energy over a period of time.

15. The disinfecting LED lighting system of claim 1, wherein the output of the first light and the output of the second light may be adjusted by adjusting a brightness or by dynamically changing an amount of light within the disinfecting wavelength range of 380 to 420 nm.

16. The disinfecting LED lighting system of claim 1, wherein the characteristic of the environment is associated with a preferred level of illuminating light provided by the first output of the first light and a predetermined threshold of disinfecting energy provided by the first output of the first light or the second output of the second light, wherein, the predetermined threshold of disinfecting energy and the preferred level of illuminating light is stored on the controller or is provided to the controller from an external source.

17. The disinfecting LED lighting system of claim 1, wherein the controller is disposed within the at least one lighting fixture.

18. A method of LED lighting disinfection comprising:
outputting, via a first light disposed within a first light fixture in an environment, a first output comprising at least 20% of emitted wavelengths within a disinfecting wavelength range of 380 to 420 nanometers (nm);
outputting, via a second light disposed within a first light fixture in an environment, a second output comprising at least 70% of the emitted wavelengths within the disinfecting wavelength range of 380 to 420 nm, wherein the second light is an independent source from the first light;
detecting, via a sensor in communication with the first light fixture, a characteristic of the environment, wherein the characteristic of the environment is an amount of disinfecting energy, and wherein the sensor is configured to detect an amount of natural light disinfecting energy and detect an amount of disinfecting energy of the first light and the second light within the disinfecting wavelength range of 380 to 420 nanometers; and causing an event, via a first controller in communication with the sensor and the first light fixture.

19. The method of claim 18, further comprising:

using the characteristic of the environment detected by the sensor to determine if the first light or the second light will be operated; and operating only the first light or only the second light.

20. The method of claim 18, further comprising:

detecting the first output or the second output, the first output and the second output correlating to the amount of disinfecting energy;

comparing the disinfecting energy of the first output or the second output to a required target dosage of disinfecting energy; and adjusting the first output or the second output to meet the required target dosage of disinfecting energy.

\* \* \* \* \*